(12) United States Patent
Do et al.

(10) Patent No.: US 11,097,015 B2
(45) Date of Patent: Aug. 24, 2021

(54) DISULFIDE BOND STABILIZED POLYPEPTIDE COMPOSITIONS AND METHODS OF USE

(71) Applicant: Amicus Therapeutics, Inc., Cranbury, NJ (US)

(72) Inventors: Hung Do, New Hope, PA (US); Ce Feng Liu, Brooklyn, NY (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 0 days.

(21) Appl. No.: 16/598,960

(22) Filed: Oct. 10, 2019

(65) Prior Publication Data

US 2020/0147241 A1    May 14, 2020

Related U.S. Application Data

(60) Provisional application No. 62/744,069, filed on Oct. 10, 2018.

(51) Int. Cl.
| | | |
|---|---|---|
| *C12N 15/79* | (2006.01) | |
| *C07H 21/04* | (2006.01) | |
| *A61K 48/00* | (2006.01) | |
| *A61P 43/00* | (2006.01) | |
| *A61K 38/46* | (2006.01) | |
| *A61K 38/47* | (2006.01) | |
| *C12N 15/86* | (2006.01) | |

(52) U.S. Cl.
CPC ........ *A61K 48/0058* (2013.01); *A61K 38/465* (2013.01); *A61K 38/47* (2013.01); *A61K 48/0033* (2013.01); *A61P 43/00* (2018.01); *C12N 15/86* (2013.01); *C07H 21/04* (2013.01); *C12N 15/79* (2013.01); *C12N 2750/14143* (2013.01); *C12N 2800/00* (2013.01); *C12Y 301/02022* (2013.01); *C12Y 302/01022* (2013.01)

(58) Field of Classification Search
CPC .................... C12N 15/79; C12N 15/86; C12N 2750/14143; C12N 2800/00; C07H 21/04
USPC .............. 435/320.1; 536/23.5, 24.1
See application file for complete search history.

(56) References Cited

U.S. PATENT DOCUMENTS

| | | | |
|---|---|---|---|
| 6,326,193 B1 | 12/2001 | Liu et al. | |
| 7,355,018 B2 | 4/2008 | Glass | |
| 7,396,811 B2 | 7/2008 | LeBowitz et al. | |
| 7,560,424 B2 | 7/2009 | LeBowitz et al. | |
| 7,629,309 B2 | 12/2009 | LeBowitz et al. | |
| 7,785,856 B2 | 8/2010 | LeBowitz et al. | |
| 7,858,576 B2 | 12/2010 | LeBowitz et al. | |
| 8,207,114 B2 | 6/2012 | LeBowitz et al. | |
| 8,492,337 B2 | 7/2013 | LeBowitz et al. | |
| 8,492,338 B2 | 7/2013 | LeBowitz et al. | |
| 9,206,235 B2 | 12/2015 | Martini et al. | |
| 9,279,007 B2 | 3/2016 | Do | |
| 9,469,683 B2 | 10/2016 | LeBowitz et al. | |
| 9,493,753 B2 | 11/2016 | Ishihara | |
| 9,545,450 B2 | 1/2017 | Do | |
| 9,814,762 B2 | 11/2017 | LeBowitz et al. | |
| 2001/0007755 A1 | 12/2001 | Borel et al. | |
| 2003/0072761 A1 | 4/2003 | LeBowitz | |
| 2006/0121018 A1 | 6/2006 | LeBowitz | |
| 2008/0241118 A1 | 10/2008 | LeBowitz | |
| 2009/0117091 A1 | 5/2009 | LeBowitz et al. | |
| 2009/0202511 A1 | 8/2009 | Galindo et al. | |
| 2009/0203575 A1 | 8/2009 | LeBowitz et al. | |
| 2010/0104589 A1 | 4/2010 | Govindan et al. | |
| 2014/0045216 A1 | 2/2014 | Do | |
| 2014/0302001 A1 | 10/2014 | Do | |
| 2017/0319710 A1 | 11/2017 | Do | |
| 2018/0125949 A1 | 5/2018 | LeBowitz et al. | |
| 2019/0343968 A1 | 11/2019 | Do et al. | |

FOREIGN PATENT DOCUMENTS

| | | | |
|---|---|---|---|
| CN | 102066422 A | 5/2011 | |
| EP | 1436316 B1 | 1/2008 | |
| EP | 1974752 B1 | 9/2012 | |
| EP | 3115372 A1 | 1/2017 | |
| EP | 3187508 A1 | 7/2017 | |
| EP | 2925776 B1 | 5/2018 | |
| JP | 2002-530426 A | 9/2002 | |
| JP | 2007-528212 A | 10/2007 | |
| JP | 2009-533364 A | 9/2009 | |
| WO | 2000/031113 A1 | 6/2000 | |
| WO | 2001/029058 A1 | 4/2001 | |
| WO | 2001/096584 A2 | 12/2001 | |
| WO | 2003/032727 A1 | 4/2003 | |

(Continued)

OTHER PUBLICATIONS

Bryan et al., 2013, http://www.elsevierblogs.com/currentcomments/?p=962, Implications of protein fold switching, p. 1-4.*
Maqbool et al., 2015 (Biochemical Society Transactions, vol. 43, No. 5, p. 1011-1017.*
Cruz et al., 2017, Methods in Molecular Biology, vol. 1654, p. 55-75.*
Calhoun, David, 2017, US 20170051267 A1.*
Blits, Bas, 2016, US 20160243260 A1.*
De Frees et al., 2004, GeneSeq Accession No. ADN49739, computer printout, pp. 5-7.*
Nathwani et al., Apr. 26, 2018, US 20180110878 A1.*

(Continued)

*Primary Examiner* — Shin Lin Chen
(74) *Attorney, Agent, or Firm* — Hyun Joon Chung; Margareta K. Sorenson

(57) ABSTRACT

Provided herein are polypeptides comprising one or more non-native cysteine residues that form a disulfide bridge between non-native cysteines within the protein or between non-native cysteines of two monomers of the protein. Such modified human polypeptides are useful in treatment of genetic diseases via enzyme replacement therapy and/or gene therapy.

20 Claims, 12 Drawing Sheets

Specification includes a Sequence Listing.

(56) References Cited

FOREIGN PATENT DOCUMENTS

| WO | 2004/064750 A2 | 8/2004 |
|----|----------------|--------|
| WO | 2004/098648 A1 | 11/2004 |
| WO | 2005/047302 A1 | 5/2005 |
| WO | 2007/115724 A2 | 10/2007 |
| WO | 2009/137721 A2 | 11/2009 |
| WO | 2014/085621 A1 | 6/2014 |
| WO | 2014/143734 A2 | 9/2014 |
| WO | 2015/060722 A1 | 4/2015 |
| WO | 2015/085238 A1 | 6/2015 |

OTHER PUBLICATIONS

A Phase 2, Open-Label, Multicenter, Ascending-Dose, 12-Week Study to Evaluate the Study, Tolerability, Pharmacokinetics, and Pharmacodynamics of AT1001 in Patients with Fabry Disease; ClinicalTrials.gov, U.S. National Institute of Health, 2005, 3 pages.
"A Phase 2, Open-Label, Multiple Dose Level, 12-Week Study to Evaluate the Safety, Tolerability, and Pharmacodynamics of AT1001 in Female Patients with Fabry Disease", ClinicalTrials Identifier—NCT00304512, ClinicalTrials.gov, U.S. National Institute of Health, 2006, 4 pages.
"A Phase 2; Open-Label, Single Dose Level, 12-Week Study to Evaluate the Safety, Tolerability, and Pharmacodynamics of AT1001 in Patients with Fabry Disease", ClinicalTrials Identifier—NCT00283959; ClinicalTrials.gov, U.S. National Institute of Health, 2006, 3 pages.
"A Phase 2, Open-Label, Single Dose Level, 24-Week Study to Evaluate the Safety, Tolerability, and Pharmacodynamics of AT1001 in Patients with Fabry Disease", ClinicalTrials Identifier—NCT00283933, ClinicalTrials.gov, U.S. National Institute of Health, 2006, 3 pages.
Advisory Action received for U.S. Appl. No. 15/347,006, dated Jan. 28, 2019, 8 pages.
Alfonso et al., "Miglustat (NB-DNJ) Works as a Chaperone for Mutated Acid β-Glucosidase in Cells Transfected with Several Gaucher Disease Mutations", Blood Cells, Molecules and Diseases, vol. 35, No. 2, 2005, pp. 268-276.
"Amicus Therapeutics Announces Positive Phase 3 Data from Fabry Monotherapy Study 012", Amicus Therapeutics, Inc., Aug. 20, 2014, 3 pages.
"Amicus Therapeutics Announces Presentations and Posters at 12th Annual WORLDSymposium™ 2016", Amicus Therapeutics, Inc, Feb. 10, 2016, 3 pages.
Andersson et al., "Individualization of Long-Term Enzyme Replacement Therapy for Gaucher Disease", Genetics IN Medicine, vol. 7. No. 2, Feb. 2005, pp. 105-110.
Applicant Initiated Interview Summary received for U.S. Appl. No. 15/347,006, dated Oct. 4, 2019, 3 pages.
Benjamin et al., "The Pharmacological Chaperone 1-deoxygalactonojirimycin Increases α-Galactosidase A Levels in Fabry Patient Cell Lines", The Journal of Inherited Metabolic Disease, vol. 32, 2009, pp. 424-440.
Benjamin et al., "The Validation of Pharmacogenetics for the Identification of Fabry Patients to be Treated with Migalastat", Genetics in Medicine, vol. 19, No. 4, Apr. 2017, pp. 430-438.
Benjamin et al., "The Validation of Pharmacogenetics in the Identification of Target Fabry Patients for Treatment with Migalastat", Amicus Therapeutics, Apr. 2017, 1 page.
Bichet et al., "Persistence of Positive Renal and Cardiac Effects of Migalastat in Fabry Patients with Amenable Mutations Following 30 Months of Treatment in the ATTRACT Study", Amicus Therapeutics, Mar. 2016, 1 page.
Bishop et al., "Affinity Purification of α-Galactosidase A from Human Spleen, Placenta and Plasma with Elimination of Pyrogen Contamination", Journal of Biological Chemistry, vol. 256, No. 3, Feb. 10, 1981, pp. 1307-1316.

Bishop et al., "Human α-Galactosidase A: Nucleotide Sequence of a cDNA Clone Encoding the Mature Enzyme", Proceedings of the National Academy of Sciences USA, vol. 83, Jul. 1986, pp. 4859-4863.
Bishop et al., "Molecular Cloning and Nucleotide Sequencing of A cDNA Encoding Human A-Galactosidase A.", Molecular Genetics, 1 page.
Brady et al., "Enzymatic Defect in Fabry's Disease—Ceramidetrihexosidase Deficiency", The New England Journal of Medicine, vol. 276, No. 21, May 25, 1967, pp. 1163-1167.
Branum et al., "Effect of Two Anticoagulants on Leukocyte Yield and Function, and on Lysosomal Enzyme Activity", Clinical Chemistry, vol. 34, No. 1, 1988, pp. 110-113.
Brooks, Doug A., "Getting into the Fold", Nature Chemical Biology, vol. 3, No. 2, Feb. 2007, pp. 84-85.
Brown et al., "A Single-Vector Approach to Hypercholesterolemia Gene Therapy with AAV-Cas13d", Molecular Therapy, vol. 27, No. 4S1, Apr. 2019, pp. 243-244.
Brown et al., "Strategies for Correcting the AF508 CFTR Protein-Folding Defect", Journal of Bioenergetics and Biomembranes, vol. 29, No. 5, 1997, pp. 491-502.
Butters, Terry D., "Pharmacotherapeutics Strategies Using Small Molecules for the Treatment of Glycolipid Lysosomal Storage Disorders", Expert Opinion on Pharmacotherapy, vol. 8, No. 4, Feb. 19, 2007, pp. 427-435.
Calhoun et al., "Fabry Disease: Isolation of a cDNA Clone Encoding Human α-Galactosidase A", Proceedings of the National Academy of Sciences USA, vol. 82, Nov. 1985, pp. 7364-7368.
"CFP UniProtKB—A0A059PIU2 (A0A059PIU2_AEQVI)", last viewed on Jul. 10, 2015, Jul. 10, 2015, 4 pages.
Ciplys et al., "Generation of Human ER Chaperone BiP in Yeast *Saccharomyces cerevisiae*", Microbial Cell Factories, vol. 13, No. 22, 2014, 9 pages.
Davies et al., "Fabry Disease: Fourteen α-Galactosidase A Mutations in Unrelated Families from the United Kingdom and Other European Countries", European Journal of Human Genetics, vol. 4, No. 4, 1996, pp. 219-224.
Decision to Grant received for European Patent Application No. 11843849.8, dated Jun. 7, 2018, 8 pages.
Decision to Grant received for European Patent Application No. 12793015.4, dated Oct. 26, 2017, 2 pages.
Decision to Grant received for European Patent Application No. 18181451.8, dated Jul. 9, 2020, 2 pages.
Deng et al., "Aspirin and Salicylate Bind to Immunoglobulin Heavy Chain Binding Protein (BiP) and Inhibit Its ATPase Activity in Human Fibroblasts", The FASEB Journal, vol. 15, No. 13, 2001, pp. 2463-2470.
Desnick et al., "α-Galactosidase A Deficiency: Fabry Disease", The Metabolic and Molecular Bases of Inherited Disease, McGraw-Hill, 8th Edition, vol. 3, Chapter 150, 2001, 44 pages.
Devos et al., "Practical Limits of Function Prediction", Proteins: Structure, Function and Genetics, vol. 41, 2000, pp. 98-107.
Dobrovolny et al., "Relationship Between X-Inactivation and Clinical Involvement in Fabry Heterozygotes, Eleven Novel Mutations in the α-Galactosldase A gene in the Czech and Slovak Population", Journal of Molecular Medicine, vol. 83, 2005, pp. 647-654.
Doerfler et al., "Targeted Approaches to Induce Immune Tolerance for Pompe Disease Therapy", Molecular Therapy—Methods Clinical Development, vol. 3, No. 15053, 2016, 11 pages.
Dombkowski et al., "Protein Disulfide Engineering", FEBS Letters, vol. 588, No. 2, 2014, pp. 206-212.
Eng et al., "Fabry Disease: Thirty-Five Mutations in the α-Galactosidase A Gene in Patients with Classic and Variant Phenotypes", Molecular Medicine, vol. 3, No. 3, Mar. 1997, pp. 174-182.
Eng et al., "Nature and Frequency of Mutations in the α-Galactosidase A Gene That Cause Fabry Disease", American Journal of Human Genetics, vol. 53, 1993, pp. 1186-1197.
Extended European Search Report received for European Patent Application No. 11843849.8, dated Nov. 26, 2014, 6 pages.
Extended European Search Report received for European Patent Application No. 12793015.4, dated Jul. 24, 2015, 11 pages.
Extended European Search Report received for European Patent Application No. 18181451.8, dated Feb. 25, 2019, 4 pages.

(56) References Cited

OTHER PUBLICATIONS

EU Clinical Trials Register, "A Phase 2, Open-Label, Multiple Dose Level, 12-Week Study to Evaluate the Safety, Tolerability, and Pharmacodynamics of AT1001 in Female Patients with Fabry Disease", Available online at: https://www.clinicaltrialsregister.eu/ctr-search/trial/2006-000181-36/GB, Retrieved on: Apr. 11, 2017, 4 pages.

EU Clinical Trials Register, "A Phase 2, Open-Label, Single Dose Level, 24-Week Study to Evaluate the Safety, Tolerability, and Pharmacodynamics of AT1001 in Patients with Fabry Disease", Available online at: https://www.clinicaltrialsregister.eu/ctr-search/trial/2005-004384-33/GB, Retrieved on: Apr. 11, 2017, 2005, 4 pages.

Fan, Jian-Qiang, "A Contradictory Treatment for Lysosomal Storage Disorders: Inhibitors Enhance Mutant Enzyme Activity", Trends in Pharmacological Sciences Elsevier, Haywarth, vol. 24, No. 7, Jul. 2003, pp. 355-360.

Fan et al., "Accelerated Transport and Maturation of Lysosomal α-Galactosidase A in Fabry Lymphoblasts by an Enzyme Inhibitor", Nature Medicine, vol. 5, No. 1, Jan. 1999, pp. 112-115.

Fan et al., "Cell-Based Screening of Active-Site Specific Chaperone for the Treatment of Fabry Disease", Methods in Enzymology, vol. 363, 2003, pp. 412-420.

Feldt-Rasmussen et al., "Response of Patients with Fabry Disease with the Amenable GLA Mutation p.N215S to Treatment with Migalastat", Presented at the 13th International Congress on Inborn Errors of Metabolism (ICIEM) 2017, Sep. 5-8, 2017, 1 page.

Fernandez et al., "Distinct Molecular Events during Secretory Granule Biogenesis Revealed by Sensitivities to Brefeldin A", Molecular Biology of the Cell, vol. 8, Nov. 1997, pp. 2171-2185.

Ferreira et al., "The Alpha-Galactosidase A p.Arg118Cys Variant Does Not Cause a Fabry Disease Phenotype: Data from Individual Patients and Family Studies", Molecular Genetics and Metabolism, vol. 114, No. 2, Feb. 2015, pp. 248-258.

Ferreira et al., "Tuning Gene Expression with Synthetic Upstream Open Reading Frames", Proceedings of the National Academy of Sciences, U.S.A., vol. 110, No. 28, 2013, pp. 11284-11289.

Final Office Action received for U.S. Appl. No. 13/988,946, dated Jul. 17, 2015, 21 pages.

Final Office Action received for U.S. Appl. No. 15/347,006, dated Sep. 17, 2018, 5 pages.

First Notification to make Rectification received for Chinese Patent Application No. 201280037051.0, dated Jul. 4, 2014, 1 page (English Translation only).

Form 8-K, "Current Report Pursuant to Section 13 or 15(d) of the Securities Exchange Act of 1934", Amicus Therapeutics, Inc., Mar. 3, 2016, 10 pages.

Freiden et al., "Interconversion of Three Differentially Modified and Assembled Forms of BiP", The EMBO Journal, vol. 11, No. 1, 1992, pp. 63-70.

Frustaci et al., "Improvement in Cardiac Function in the Cardiac Variant of Fabry's Disease with Galactose-Infusion Therapy", New England Journal of Medicine, The Massachusetts Medical Society, Waltham, vol. 345, No. 1, Jul. 5, 2001, pp. 25-32.

Fuller et al., "Urinary Lipid Profiling for the Identification of Fabry Hemizygotes and Heterozygotes", Clinical Chemistry, vol. 51, No. 4, 2005, 7 pages.

"Galafold Product Information: Galafold 123 Mg Hard Capsules", 2016, 45 pages.

"Galafold Summary of Product Characteristics: Galafold 123 Mg Hard Capsules", 2018, 49 pages.

"Galafold™ (Migalastat) Capsules, for Oral Use", Aug. 2018, 24 pages.

Gao et al., "Interchain Disulfide Bonds Promote Protein Cross-Linking During Protein Folding", Journal of Biochemistry, vol. 129, No. 1, 2001, pp. 179-183.

Sands et al., "Gene Therapy for Lysosomal Storage Diseases", Molecular Therapy: The Journal of the American Society of Gene Therapy, Cell Press, vol. 13, No. 5, May 1, 2006, pp. 839-849.

Germain et al., "Efficacy of the Pharmacologic Chaperone Migalastat in a Subset of Male Patients with the Classic Phenotype of Fabry Disease and Migalastat-amenable Variants: Data from the Phase 3 Randomized, Multicenter, Double-Blind Clinical Trial and Extension Study", Genetics in Medicine, vol. 21, No. 9, Sep. 2019, pp. 1987-1997.

Germain et al., "Lysosomal Disorders: Sphingolipidoses; Subjects Treated with Migalastat Continue to Demonstrate Stable Renal Function and Reduced Left Ventricular Mass Index over 3 Years in a Long-Term Extension Study of Fabry Disease", Journal of Inherited Metabolic Diseases, 2015, 2 pages.

Germain et al., "Safety and Pharmacodynamic Effects of a Pharmacological Chaperone on α-galactosidase a Activity and Globotriaosylceramide Clearance in Fabry Disease: Report From Two Phase 2 Clinical Studies", Orphanet Journal of Rare Diseases, vol. 7, 2012, 11 pages.

Germain et al., "Treatment of Fabry's Disease with the Pharmacologic Chaperone Migalastat", The New England Journal of Medicine, vol. 375, Aug. 11, 2016, pp. 545-555.

Giugliani et al., "A Phase 2 Study of Migalastat Hydrochloride in Females with Fabry Disease: Selection of Population, Safety and Pharmacodynamic Effects", Molecular Genetics and Metabolism, vol. 109, 2013, pp. 86-92.

Guerard et al., "Lucerastat, an Iminosugar for Substrate Reduction Therapy: Pharmacokinetics, Tolerability, and Safety in Subjects with Mild, Moderate, and Severe Renal Function Impairment"; The Journal of Clinical Pharmacology, The American College of Clinical Pharmacology, vol. 57, No. 11, 2017, pp. 1425-1431.

Guerard et al., "Lucerastat, an Iminosugar for Substrate Reduction Therapy: Tolerability, Pharmacodynamics, and Pharmacokinetics in Patients with Fabry Disease on Enzyme Replacement", Clinical Pharmacology & Therapeutics, vol. 103, No. 4, Apr. 2018, pp. 703-711.

Guerard et al., "Lucerastat, an Iminosugar With Potential as Substrate Reduction Therapy for Glycolipid Storage Disorders: Safety, Tolerability, and Pharmacokinetics in Healthy Subjects", Orphanet Journal of Rare Diseases, vol. 12, No. 1, 2017, 10 pages.

Guo et al., "Protein Tolerance to Random Amino Acid Change", Proceedings of the National Academy of Sciences, vol. 101, No. 25, 2004, pp. 9205-9210.

Heldermon et al., "Disease Correction by Combined Neonatal Intracranial AAV and Systemic Lentiviral Gene Therapy in Sanfilippo Syndrome Type B Mice", Gene Therapy, vol. 20, No. 9, 2013, pp. 913-921.

Hill et al., "Functional Analysis of Conserved Histidines in ADP-Glucose Pyrophosphorylase from *Escherichia coli*", Biochemical and Biophysical Research Communications; vol. 244, 1998, pp. 573-577.

Hochstrasser, Mark, "Ubiquitin-Dependent Protein Degradation", Annual Review of Genetics, vol. 30, 1996, pp. 405-439.

Hocquemiller et al.; "Adeno-Associated Virus-Based Gene Therapy for CNS Diseases", Human Gene Therapy, vol. 27, No. 7, 2016, pp. 478-496.

Huang et al., "Lentivector Iterations and Pre-Clinical Scale-Up/Toxicity Testing: Targeting Mobilized CD34 + Cells for Correction of Fabry Disease", Molecular Therapy—Methods & Clinical Development, vol. 5, Jun. 2017, pp. 241-258.

Hughes et al., "Long-term Efficacy and Safety of Migalastat Compared to Enzyme Replacement Therapy in Fabry Disease: Phase 3 Study Result", Molecular Genetics and Metabolism, 2015, 2 pages.

Hughes et al., "Oral Pharmacological Chaperone Migalastat Compared with Enzyme Replacement Therapy in Fabry Disease: 18-Month Results from the Randomised Phase III ATTRACT Study", Journal of Medical Genetics, vol. 54, No. 4, 2017, pp. 288-296.

Hughes et al., "Phenotype of Fabry Disease in Patients with Mutations Amenable to Migalastat", Molecular Genetics and Metabolism, Feb. 2016, 1 page.

Hughes et al., "Response of Patients with Fabry Disease with the Amenable GLA Mutation p.N215S to Treatment with Migalastat (ATTRACT Study)", Presented at the 13th Annual WORLDSymposium™, 2017, 1 page.

"Human alpha-galactosidase A mutant G360C", XP002797397, Database accession No. BD022099, Apr. 6, 2017, 1 page.

(56) References Cited

OTHER PUBLICATIONS

"Human alpha-galactosidase A mutant I359C", XP002797396, Database accession No. BD022098, Apr. 6, 2017, 1 page.
Intention to Grant received for European Patent Application No. 11843849.8, dated Jan. 29, 2018, 8 pages.
Intention to Grant received for European Patent Application No. 11843849.8, dated Jun. 19, 2017, 6 pages.
Intention to Grant received for European Patent Application No. 11843849.8, dated May 17, 2018, 6 pages.
Intention to Grant received for European Patent Application No. 12793015.4, dated Apr. 24, 2017, 7 pages.
Intention to Grant received for European Patent Application No. 12793015.4, dated Oct. 16, 2017, 6 pages.
Intention to Grant received for European Patent Application No. 18181451.8, dated Feb. 25, 2020, 6 pages.
International Preliminary Report on Patentability received for PCT Patent Application No. PCT/US2012/039705, dated Apr. 3, 2014, 10 pages.
International Preliminary Report on Patentability received for PCT Patent Application No. PCT/US2011/061862, dated Jan. 10, 2013, 8 pages.
International Search Report and Written Opinion received for PCT Patent Application No. PCT/US2011/061862, dated May 30, 2012, 10 pages.
International Search Report and Written Opinion received for PCT Patent Application No. PCT/US2012/039705, dated Dec. 7. 2012, 14 pages.
International Search Report and Written Opinion received for PCT Patent Application No. PCT/US2019/030076, dated Oct. 11, 2019, 25 pages.
International Search Report and Written Opinion received for PCT Patent Application No. PCT/US2019/055679, dated Jun. 23, 2020, 18 pages.
Invitation to Pay Additional Fees received for PCT Patent Application No. PCT/US2019/030076, dated Aug. 19, 2019, 20 pages.
Invitation to Pay Addition Fees and Partial International Search Report received for PCT Patent Application No. PCT/US2019/055679, dated Feb. 21, 2020, 17 pages.
Ishii et al., "Aggregation of the Inactive Form of Human α-Galactosidase in the Endoplasmic Reticulum", Biochemical and Biophysical Research Communications, vol. 220, 1996, pp. 812-815.
Ishii et al., "Mutant α-Galactosidase a Enzymes Identified in Fabry Disease Patients with Residual Enzyme Activity: Biochemical Characterization and Restoration of Normal Intracellular Processing by 1-Deoxygalactonojirimycin", Journal of Biochemistry, vol. 406, No. 2, Sep. 1, 2007, pp. 285-295.
Ishii et al., "Transgenic Mouse Expressing Human Mutant α-galactosidase A in an Endogenous Enzyme Deficient Background: a Biochemical Animal Model for Studying Active-site Specific Chaperone Therapy for Fabry Disease", Biochimica et Biophysica Acta, vol. 1690, No. 3, Nov. 5, 2004, pp. 250-257.
Johnson et al., "An Open-Label Study to Determine the Pharmacokinetics and Safety of Migalastat HCl in Subjects with Impaired Renal Function and Healthy Subjects with Normal Renal Function", Clinical Pharmacology in Drug Development, 2015, pp. 256-261.
Johnson et al., "Comparison of Integrated White Blood Cell α-Galactosidase a Activity Exposure Between Every-Other-Day Orally Administered Migalastat and Biweekly Infusions of Agalsidase Beta or Agalsidase Alfa", Presented at World Symposium for Lysosomal Disorders Annual Meeting, Mar. 2016, 1 page.
Johnson et al., "Pharmacokinetic Simulation of a 150-Mg Every Other Day Dose Regimen for the Pharmacological Chaperone Migalastat HCl in Fabry Disease", Presented at American College of Clinical Pharmacy (ACCP) Annual Meeting, 2017, 1 page.
June et al., "Engineering Lymphocyte Subsets: Tools, Trials and Tribulations", Nature Reviews Immunology, vol. 9, No. 10, 2009, pp. 704-716.
Khanna et al., "Co-Administration of the Pharmacological Chaperone AT2221 with a Proprietary Recombinant Human Acid ??-Glucosidase Leads to Greater Plasma Exposure and Substrate Reduction Compared to Alglucosidase Alfa", World LDS 2016, 2016, 1 page.
Kilian et al., "Identification and Characterization of a New Conserved Motif Within the Presequence of Proteins Targeted into Complex Diatom Plastids", The Plant Journal, vol. 41, 2005, pp. 175-183.
Kisselev, Lev, "Polypeptide Release Factors in Prokaryotes and Eukaryotes: Same Function, Different Structure", Structure, vol. 10, No. 1, 2002, pp. 8-9.
Kizhner et al., "Characterization of a Chemically Modified Plant Cell Culture Expressed Human α-Galactosidase-a Enzyme for Treatment of Fabry Disease", Molecular Genetics and Metabolism, vol. 114, 2015, pp. 259-267.
Kornreich et al., "Nucleotide Sequence of the Human α-galactosidase A Gene", Nucleic Acids Research, vol. 17, No. 8, 1989, pp. 3301-3302.
Kusiak et al., "Purification and Properties of the Two Major Isozymes of α-Galactosidase from Human Placenta", The Journal of Biological Chemistry, vol. 253, No. 1, 1978, pp. 184-190.
Lazar et al., "Transforming Growth Factor α: Mutation of Aspartic Acid 47 and Leucine 48 Results in Different Biological Activities", Molecular and Cellular Biology, vol. 8, No. 3, 1988, pp. 1247-1252.
Lei et al., "Enzyme Enhancement Activity of N-octyl-β-valienamine on β-glucosidase Mutants Associated with Gaucher Disease", Biochimica et Biophysica Acta, Molecular Basis of Disease, vol. 1772, No. 5, Apr. 18, 2007, pp. 587-596.
Lock et al., "Rapid, Simple, and Versatile Manufacturing of Recombinant Adeno-Associated Viral Vectors at Scale", Human Gene Therapy, vol. 21, No. 10, 2010, pp. 1259-1271.
Lourenco et al., "Long-term Migalastat Treatment Stabilizes Renal Functions in Patents with Fabry Disease: Results from a Phase 3 Clinical Study (AT1001-041)", Presented at the 13th International Congress on Inborn Errors of Metabolism (ICIEM) 2017, 1 page.
Lu et al., "Anti-Citrullinated Protein Antibodies Bind Surface-Expressed Citrullinated Grp78 on Monocyte/macrophages and Stimulate Tumor Necrosis Factor α Production", Arthritis and Rheumatology, vol. 62, No. 5, 2010, pp. 1213-1223.
Lukas et al., "Functional and Clinical Consequences of Novel α-Galactosidase A Mutations in Fabry Disease", Human Mutation, 2015, pp. 43-51.
Lukas et al., "Functional Characterisation of Alpha-Galactosidase A Mutations as a Basis for a New Classification System in Fabry Disease", PLOS Genetics, vol. 9, No. 8, Aug. 2013, 10 pages.
Martoglio et al., "Signal Sequences: More than Just Greasy Peptides", Trends in Cell Biology, vol. 8, No. 10, 1998, pp. 410-415.
"Material Safety Data Sheet 1-Deoxygalactonojirimycin (Hydrochloride) (Migalastat)", Cayman Chemical, 2019, 5 pages.
Matsuzawa et al., "Fabry Disease: Correlation Between Structural Changes in α-galactosidase, and Clinical and Biochemical Phenotypes", Human Genetics, vol. 117, May 28, 2005, pp. 317-328.
Mayes et al., "Differential Assay for Lysosomal Alpha-galactosidases in Human Tissues and Its Application to Fabry's Disease", Clinica Chimica Acta, vol. 112, 1981, pp. 247-251.
Milone et al., "Chimeric Receptors Containing CD137 Signal Transduction Domains Mediate Enhanced Survival of T Cells and Increased Antileukemic Efficacy in vivo", Molecular Therapy, vol. 17, 2009, pp. 1453-1464.
Mizukoshi et al., "Normal Values of Left Ventricular Mass Index Assessed by Transthoracic Three-Dimensional Echocardiography", Journal of the American Society of Echocardiography, vol. 29, No. 1, Jan. 2016, pp. 51-61.
Najafian et al., "Six months of Migalastat Treatment Reduces Podocyte Globotriaosylceramide Content in Adult Male Patients with Fabry Disease", Amicus Therapeutics, Inc., 1 page.
Nakao et al., "An Atypical Variant of Fabry's Disease in Men with Left Ventricular Hypertrophy", The New England Journal of Medicine, vol. 333, No. 5, Aug. 3, 1995, pp. 288-293.
Narita et al., "Efficacy and Safety of Migalastat in a Japanese Population: a Subgroup Analysis of the ATTRACT Study", Clinical and Experimental Nephrology, vol. 24, 2020, pp. 157-166.

(56) References Cited

OTHER PUBLICATIONS

Nicholls et al., "Renal Outcomes with Up to 9 Years of Migalastat in Patients with Fabry Disease: Results from an Open-Label Extension Study", 2018, 1 page.
Non-Final Office Action received for U.S. Appl. No. 13/988,946, dated Jan. 8, 2015, 16 pages.
Non-Final Office action received for U.S. Appl. No. 14/122,858, dated Mar. 18, 2016, 21 pages.
Non-Final Office Action received for U.S. Appl. No. 15/347,006, dated Jul. 5, 2019, 7 pages.
Non-Final Office Action received for U.S. Appl. No. 15/347,006, dated Mar. 16, 2018, 10 pages.
Non-Final Office Action received for U.S. Appl. No. 16/399,979, dated Apr. 16, 2020, 16 pages.
Notice of Allowance received for Canadian Patent Application No. 2,836,318, dated Apr. 19, 2018, 1 page.
Notice of Allowance received for Chinese Patent Application No. 201180065369.5, dated Apr. 1, 2016, 4 pages (2 pages of English Translation and 2 pages of Official copy).
Notice of Allowance received for Chinese Patent Application No. 201280037051.0, dated Feb. 22, 2018, 4 pages (2 pages of English Translation and 2 pages of Official copy).
Notice of Allowance received for Japanese Patent Application No. 2014-513625, dated Jan. 30, 2018, 5 pages (2 pages of English Translation and 3 pages of Official copy).
Notice of Allowance received for Korean Patent Application No. 10-2013-7016110, dated Feb. 25, 2019, 5 pages (Official copy only). (See Communication under 37 CFR § 1.98(a) (3)).
Notice of Allowance received for Korean Patent Application No. 10-2013-7034111, dated Nov. 27, 2018, 1 page (Official copy only). (See Communication under 37 CFR § 1.98(a) (3)).
Notice of Allowance received for U.S. Appl. No. 13/988,946, dated Oct. 28, 2015, 12 pages.
Notice of Allowance received for U.S. Appl. No. 15/347,006, dated Mar. 10, 2020, 10 pages.
Notice of Allowance received for U.S. Appl. No. 14/122,858, dated Sep. 26, 2016, 9 pages.
Office Action received for Canadian Patent Application No. 2,836,318, dated May 10, 2017, 4 pages.
Office Action received for Canadian Patent Application No. 2,818,689, dated Nov. 22, 2018, 5 pages.
Office Action received for Canadian Patent Application No. 2,818,689, dated Oct. 18, 2017, 6 pages.
Office Action received for Chinese Patent Application No. 201280037051.0, dated Dec. 2, 2015, 22 pages (12 pages of English Translation and 10 pages of Official Copy).
Office Action received for Chinese Patent Application No. 201180065369.5, dated Jan. 27, 2015, 18 pages (11 pages of English Translation and 7 pages of official copy).
Office Action received for Chinese Patent Application No. 201280037051.0, dated Mar. 27, 2017, 10 pages (5 pages of English Translation and 5 pages of Official Copy).
Office Action received for Chinese Patent Application No. 201180065369.5, dated Sep. 29, 2015, 10 pages (5 pages of English Translation and 5 pages of Official Copy).
Office Action received for Chinese Patent Application No. 201280037051.0, dated Aug. 16, 2016, 19 pages (10 pages of English Translation and 9 pages of Official copy).
Office Action received for Chinese Patent Application No. 201280037051.0, dated Oct. 9, 2017, 8 pages (4 pages of English Translation and 4 pages of Official copy).
Office Action received for European Patent Application No. 11843849.8, dated Aug. 18, 2015, 3 pages.
Office Action received for European Patent Application No. 11843849.8, dated Jul. 5, 2016, 3 pages.
Office Action received for European Patent Application No. 11843849.8, dated Nov. 8, 2017, 3 pages.
Office Action received for European Patent Application No. 12793015.4, dated Aug. 11, 2015, 1 pages.
Office Action received for Japanese Patent Application No. 2014-513625, dated Apr. 26, 2016, 9 pages (4 pages of English Translation and 5 pages of Official Copy).
Office Action received for Japanese Patent Application No. 2014-513625, dated Mar. 7, 2017, 5 pages (2 pages of English Translation and 3 pages of official copy).
Office Action received for Japanese Patent Application No. 2017-133655, dated Feb. 19, 2019, 7 pages (3 pages of English Translation and 4 pages of Official Copy).
Office Action received for Japanese Patent Application No. 2017-133655, dated Jun. 19, 2018, 4 pages (2 pages of English Translation and 2 pages of Official Copy).
Office Action received for Japanese Patent Application No. 2013-541026, dated Apr. 5, 2016, 5 pages (2 pages of English Translation and 3 pages of Official copy).
Office Action received for Japanese Patent Application No. 2013-541026, dated Sep. 1, 2015, 8 pages (4 pages of English Translation and 4 pages of Official copy).
Office Action received for Japanese Patent Application No. 2014-513625, dated Oct. 3, 2017, 5 pages (2 pages of English Translation and 2 pages of Official copy).
Office Action received for Japanese Patent Application No. 2017-133655, dated Oct. 8, 2019, 6 pages (3 pages of English Translation and 3 pages of Official copy).
Office Action received for Korean Patent Application No. 10-2013-7034111, dated Dec. 8, 2017, 10 pages (4 pages of English Translation and 6 pages of Official copy).
Office Action received for Korean Patent Application No. 10-2013-7034111, dated May 30, 2018, 5 pages (2 pages of English Translation and 3 pages of Official Copy).
Office Action received for Korean Patent Application No. 10-2013-7016110, dated Aug. 14, 2018, 6 pages (2 pages of English Translation and 4 pages of Official copy).
Office Action received for Korean Patent Application No. 10-2013-7016110, dated Feb. 19, 2018, 4 pages (1 page of English Translation and 3 pages of Official copy).
Office Action received for Korean Patent Application No. 10-2019-7005833, dated Mar. 28, 2019, 4 pages (Official copy only). (See Communication under 37 CFR § 1.98(a) (3)).
Office Action received for Korean Patent Application No. 10-2019-7005833, dated Nov. 26, 2019, 5 pages (Official copy only). (See Communication under 37 CFR § 1.98(a) (3)).
Office Action received for Korean Patent Application No. 10-2019-7015057, dated Apr. 9, 2020, 3 pages (Official copy only). (See Communication under 37 CFR § 1.98(a) (3)).
Office Action received for Korean Patent Application No. 10-2019-7015057, dated Aug. 5, 2019, 3 pages (Official copy only). (See Communication under 37 CFR § 1.98(a) (3)).
Office Action received for Korean Patent Application No. 10-2019-7015057, dated Feb. 4, 2020, 3 pages (Official copy only). (See Communication under 37 CFR § 1.98(a) (3)).
Okumiya et al., "Galactose Stabilizes Various Missense Mutants of α-Galactosidase in Fabry Disease", Biochemical and Biophysical Research Communications, vol. 214, No. 3, 1995, pp. 1219-1224.
Pacienza et al., "Lentivector Transduction Improves Outcomes Over Transplantation of Human HSCs Alone in NOD/SCID/Fabry Mice", Molecular Therapy, vol. 20, No. 7, Jul. 2012, pp. 1454-1461.
Park et al., "Long-term Correction of Globotriaosylceramide Storage in Fabry Mice by Recombinant Adenoassociated Virus-mediated Gene Transfer", Proceedings of the National Academy of Sciences USA, vol. 100, No. 6, Mar. 18, 2003, pp. 3450-3454.
Partial Supplementary European Search Report received for European Patent Application No. 12793015.4, dated Apr. 8, 2015, 6 pages.
Pastores et al., "Current and Emerging Therapies for the Lysosomal Storage Disorders", Expert Opinion on Emerging Drugs, vol. 10, No. 4, Oct. 31, 2005, pp. 890-902.
Punt et al., "Analysis of the Role of the Gene bipA, Encoding the Major Endoplasmic Reticulum Chaperone Protein in the Secretion of Homologous and Heterologous Proteins in Black Aspergilli", Applied Microbiology and Biotechnology, vol. 50, 1998, pp. 447-454.

(56) References Cited

OTHER PUBLICATIONS

Puzzo et al., "Rescue of Pompe Disease in Mice by AAV-Mediated Liver Delivery of Secretable Acid α-Glucosidase", Science Translational Medicine, vol. 9, No. 418:pii:eaam6375, 2017, 13 pages.
Puzzo et al., "Supplementary Materials for: Rescue of Pompe Disease in Mice by AAV-Mediated Liver Delivery of Secretable Acid α-Glucosidase", Science Translational Medicine, vol. 9, No. 418:pii:eaam6375, 2017, 26 pages.
Qiagen Supplementary Protocol, "Fast-forward Protocol for Transient Transfection of 293 Cells in 96-well Plates Using Effectene® Transfection Reagent", 2006, 2 pages.
Qiagen Supplementary Protocol, "Transient Transfection of 293 Cells in 96-well Plates Using Polyfect® Transfection Reagent", 2001, 2 pages.
Qiagen Supplementary Protocol, "Transient Transfection of COS-7 Cells in 96-well Plates Using Polyfect® Transfection Reagent", 2001, 2 pages.
Qiu et al., Impact of Cysteine Variants on the Structure, Activity, and Stability of Recombinant Human α-galactosidase A, Protein Science, vol. 24, No. 9, Jul. 14, 2015, pp. 1401-1411.
"RecName: Full=78 kDa Glucose-Regulated Protein", UniProt:Q3S4T7, Oct. 3, 2006, 2 pages.
Restriction Requirement for U.S. Appl. No. 16/399,979, dated Nov. 25, 2019, 6 pages.
Restriction Requirement received for U.S. Appl. No. 13/988,946, dated Aug. 6, 2014, 10 pages.
Restriction Requirement received for U.S. Appl. No. 14/122,858, dated Aug. 25, 2015, 9 pages.
Restriction Requirement received for U.S. Appl. No. 15/347,006, dated Oct. 17, 2017, 8 pages.
Rinderknecht et al., "Primary Structure of Human Insulin-like Growth Factor II", FEBS Letters, vol. 89, No. 2, May 1978, pp. 283-286.
Rotwein et al., "The Complex Genetics of Human Insulin-like Growth Factor 2 Are Not Reflected in Public Databases", Journal of Biological Chemistry, vol. 293, No. 12, Feb. 2, 2018, pp. 1-18.
Sawkar et al., "Gaucher Disease-Associated Glucocerebrosidases Show Mutation-Dependent Chemical Chaperoning Profiles", Chemistry and Biology, Current Biology, London, GB, vol. 12, No. 11, Jan. 11, 2005, pp. 1235-1244.
Sawkar et al., "Therapeutic Strategies to Ameliorate Lysosomal Storage Disorders—a Focus on Gaucher Disease", Cellular and Molecular Life Sciences, vol. 63, No. 10, 2006, pp. 1179-1192.
Schiffmann et al., "Effects of Long-term Migalastat Treatment on Renal Function by Baseline Proteinuria in Patients (PTS) With Fabry Disease", Nephrology Dialysis Transplantation, vol. 33 (Supplement 1), 2018, pp. i347-i358.
Schiffmann et al., "Long-Term Migalastat Treatment Stabilizes Renal Functions in Patients with Fabry Disease-Results from a Phase 3 Clinical Study (AT1001-041)", Presented at the 54th European Renal Association-European Dialysis and Transplant Association Congress, Jun. 3-6, 2017, 1 page.
Schiffmann et al., "Pegunigalsidase Alfa, a Novel PEGylated Enzyme Replacement Therapy for Fabry Disease, Provides Sustained Plasma Concentrations and Favorable Pharmacodynamics: A 1-Year Phase 1/2 Clinical Trial", Journal of Inherited Metabolic Disease, vol. 42, No. 3, May 2019, pp. 534-544.
Shimotori et al., "Novel Mutations of the GLA Gene in Japanese Patients with Fabry Disease and Their Functional Characterization by Active Site Specific Chaperone", Human Mutation, vol. 29, No. 2, Jan. 18, 2008, pp. 1-10.
Shin et al., "Prediction of Response of Mutated α-Galactosidase A to a Pharmacological Chaperone", Pharmacogenetics and Genomics, vol. 18, No. 9, Sep. 2008, pp. 773-780.
Shin et al., "Screening for Pharmacological Chaperones in Fabry Disease", Biochemical and Biophysical Research Communications, vol. 359, No. 1, 2007, pp. 168-173.
Steet, et al., "The Iminosugar Isofagomine Increase the Activity of N370s Mutant Acid β-Glucosidase in Gaucher Fibroblasts by Several Mechanisms", Proceedings of the National Academy of Sciences, vol. 103, No. 37, Sep. 12, 2006, pp. 13813-13818.
Sunder-Plassmann et al., "Migalastat for the Treatment of Fabry Disease", Expert Opinion on Orphan Drugs, vol. 6, No. 5, 2018, pp. 301-309.
Supplemental Notice of Allowance received for U.S. Appl. No. 13/988,946, dated Nov. 20, 2015, 5 pages.
Supplementary European Search Report received for European Patent Application No. 12793015.4, dated Jul. 7, 2016, 4 pages.
Torra et al., "Clinical Outcomes with Migalastat in Patients with Fabry Disease Based on Degree of Renal Impairment: Results from Phase 3 Trials", Nephrology Dialysis Transplantation 33 (Supplement 1), 2018, 1 page.
"Transfecting Plasmid DNA into GripTite(TM) 293 MSR Cells Using Lipofectamine™ LTX Reagent", Invitrogen, Jun. 20, 2006, 2 pages.
"Transfecting Plasmid DNA into HEK 293 Cells Using Lipofectamine™ LTX Reagent", Invitrogen, Nov. 17, 2006, 2 pages.
"Transfecting Plasmid DNA into COS-7 Cells Using Lipofectamine™ LTX Reagent", Invitrogen, Jun. 9, 2006, 2 pages.
Tsuji et al., "Signal Sequence and DNA-mediated Expression of Human Lysosomal α-galactosidase A", European Journal of Biochemistry, vol. 165, No. 2, 1987, pp. 275-280.
Tuske et al., "Development of a Novel Gene Therapy for Pompe Disease: Engineered Acid Alpha-glucosidase Transgene for Improved Expression and Muscle Targeting", American Society of Gene & Cell Therapy Annual Meeting in Washington DC, Apr. 30, 2019, 10 pages.
Tuske et al., "Development of a Novel Gene Therapy for Pompe Disease: Engineered Acid Alpha-glucosidase Transgene for Improved Expression and Muscle Targeting", Molecular Therapy, (Abstract 518), Apr. 15, 2019, 2 pages.
"UniParc—UPI00005DE123", Q354T7, last viewed on May 29, 2007, 2 pages.
"View of NCT00214500 on Sep. 21, 2005", Developed by the National Library of Medicine, Available online at: https://clinicaltrials.gov/archive/NCT00214500/2005_09_21, 2005, 3 pages.
"View of NCT00283933 on Jan. 30, 2006", Developed by the National Library of Medicine, Available online at: https://clinicaltrials.gov/archive/NCT00283933/2006_01_30, 2006, 3 pages.
"View of NCT00283959 on Jan. 30, 2006", Developed by the National Library of Medicine, Available online at: https://clinicaltrials.gov/archive/NCT00283959/2006_01_30, 2006, 3 pages.
"View of NCT00304512 on Mar. 17, 2006", Developed by the National Library of Medicine, Available online at: https://clinicaltrials.gov/archive/NCT00304512/2006_03_17, 2006, 4 pages.
Wacey et al., "Disentangling the Perturbational Effects of Amino Acid Substitutions in the DNA-Binding Domain of P53", Human Genetics, vol. 104, 1999, pp. 15-22.
Weinberg et al., "Effect of Shipment, Storage, Anticoagulant, and Cell Separation on Lymphocyte Proliferation Assays for Human Immunodeficiency Virus-Infected Patients", Clinical and Diagnostic Laboratory Immunology, vol. 5, No. 6, Nov. 1998, pp. 804-807.
Weinreb et al., "Guidance on the Use of Miglustat for Treating Patients with Type 1 Gaucher Disease", American Journal of Hematology, vol. 80, 2005, pp. 223-229.
Welch et al., "Influence of Molecular and Chemical Chaperones on Protein Folding", Cell Stress and Chaperones, vol. 1, No. 2, 1996, pp. 109-115.
Whisstock et al., "Prediction of Protein Function from Protein Sequence and Structure", Quarterly Reviews of Biophysics, vol. 36, No. 3, 2003, pp. 307-340.
Witkowski et al., "Conversion of a β-Ketoacyl Synthase to a Malonyl Decarboxylase by Replacement of the Active-Site Cysteine with Glutamine", Biochemistry, vol. 38, 1999, pp. 11643-11650.
Wu, Juan-Juan, "Molecular Chaperon and MHC", Foreign Medical Sciences Section of Immunology, vol. 27, No. 6, Nov. 2004, pp. 358-361 (Official Copy Only). (See Communication under 37 CFR § 1.98(a) (3)).
Wu et al., "Targeting to the Endoplasmic Reticulum Improves the Folding of Recombinant Human Telomerase Reverse Transcriptase", Protein Expression and Purification, vol. 56, No. 1, 2007, pp. 8-19.

(56) References Cited

OTHER PUBLICATIONS

Wustman et al., "Pharmacological Chaperone Therapy for Gaucher Disease: Mechanism of Action, a Survey of Responsive Mutations and Phase I Clinical Trial Results", Molecular Genetics and Metabolism, vol. 93, No. 2, 2008, 1 page.

Yam et al., "A Synthetic Chaperone Corrects the Trafficking Defect and Disease Phenotype in a Protein Misfolding Disorder", The FASEB Journal: Official Publication of the Federation of American Societies for Experimental Biology, vol. 19, No. 1, Jan. 2005, pp. 12-18.

Yam et al., "Pharmacological Chaperone Corrects Lysosomal Storage in Fabry Disease Caused by Trafficking-incompetent Variants", The American Journal of Physiology-Cell Physiology, vol. 290, 2006, pp. C1076-C1082.

* cited by examiner

Enzyme1 — Enzyme2

1) R49C - G361C
2) R49C – G360C
3) D233C – I359C
4) M51C – G360C
5) S276C – S276C

GB3 Substrate Histology Kidney

WT

GLA ko

GTx Amicus GLA

DISULFIDE BOND STABILIZED POLYPEPTIDE COMPOSITIONS AND METHODS OF USE

CROSS-REFERENCE

This application claims the benefit of U.S. Provisional Application No. 62/744,069, filed Oct. 10, 2018, which application is hereby incorporated herein by reference in its entirety.

SEQUENCE LISTING

The instant application contains a Sequence Listing which has been filed electronically in ASCII format and is hereby incorporated by reference in its entirety. Said ASCII copy, created on Jan. 23, 2020, is named 36003-704_201_SL.txt and is 55,210 bytes in size.

BACKGROUND

Genetic diseases can be treated with enzyme replacement therapy using recombinant polypeptides or gene therapy using nucleic acids encoding recombinant proteins. For example, Fabry disease may be treated using recombinant alpha-galactosidase A or small molecule chaperones such as 1-deoxygalactonojirimycin (Migalastat). However, the recombinant wildtype polypeptides often have poor stability at neutral pH and are quickly degraded in serum. This limits the half-life of the therapeutic enzyme substantially, as it is delivered by intravenous infusion.

SUMMARY

In certain aspects, there are provided gene therapy vectors comprising a nucleic acid construct comprising: a nucleic acid encoding a stabilized form of a protein for treating a genetic disorder. In some embodiments, the stabilized form comprises one or more non-native cysteine residues that form a disulfide bridge between non-native cysteines within the protein or between non-native cysteines of two monomers of the protein. In some embodiments, the protein is selected from the group consisting of alpha-galactosidase A, β-glucocerebrosidase, glucocerebrosidase, lysosomal acid lipase, glycosaminoglycan alpha-L-iduronidase, alpha-L-iduronidase, N-sulfoglucosamine sulfohydrolase (SGSH), N-acetyl-alpha-glucosaminidase (NAGLU), iduronate-2-sulfatase, N-acetylgalactosamine-6-sulfatase, glycosaminoglycan N-acetylgalactosamine 4-sulfatase, alpha-glucosidase, tripeptidyl peptidase 1 (TPP1), palmitoyl protein thioesterases (PPTs), ceroid lipofuscinoses neuronal 1, ceroid lipofuscinoses neuronal 2, ceroid lipofuscinoses neuronal 3, ceroid lipofuscinoses neuronal 4, ceroid lipofuscinoses neuronal 5, ceroid lipofuscinoses neuronal 6, ceroid lipofuscinoses neuronal 7, ceroid lipofuscinoses neuronal 8, ceroid lipofuscinoses neuronal 9, ceroid lipofuscinoses neuronal 10, ceroid lipofuscinoses neuronal 11, ceroid lipofuscinoses neuronal 12, ceroid lipofuscinoses neuronal 13, ceroid lipofuscinoses neuronal 14, ceroid lipofuscinoses neuronal 15, ceroid lipofuscinoses neuronal 16, and cyclin dependent kinase like 5. In some embodiments, the protein is selected from the group consisting of alpha-galactosidase A, β-glucocerebrosidase, glucocerebrosidase, lysosomal acid lipase, glycosaminoglycan alpha-L-iduronidase, alpha-L-iduronidase, N-sulfoglucosamine sulfohydrolase (SGSH), N-acetyl-alpha-glucosaminidase (NAGLU), iduronate-2-sulfatase, N-acetylgalactosamine-6-sulfatase, glycosaminoglycan N-acetylgalactosamine 4-sulfatase, alpha-glucosidase, tripeptidyl peptidase 1 (TPP1), palmitoyl protein thioesterases (PPTs), ceroid lipofuscinoses neuronal 4, ceroid lipofuscinoses neuronal 10 (cathepsin D), ceroid lipofuscinoses neuronal 11 (progranulin), ceroid lipofuscinoses neuronal 13 (cathepsin F), ceroid lipofuscinoses neuronal 14 (KCTD7), ceroid lipofuscinoses neuronal 15 (TBCK), and cyclin dependent kinase like 5. In some embodiments, the stabilized protein comprises a lysosomal enzyme. In some embodiments, the stabilized protein comprises a stabilized α-galactosidase (α-GAL) protein. In some embodiments, the stabilized α-galactosidase A (α-GAL) protein comprises one or more non-native cysteine residues selected from the group consisting of: (i) D233C and I359C; and (ii) M51C and G360C. In some embodiments, the stabilized protein comprises a stabilized palmitoyl protein thioesterase 1 (PPT1). In some embodiments, the stabilized PPT1 protein comprises non-native cysteine residues A171C and A183C. In some embodiments, the stabilized protein has a longer half-life at pH 7.4 compared to a corresponding protein without the non-native cysteines. In some embodiments, the stabilized protein can replace a protein defective or deficient in the genetic disorder. In some embodiments, the stabilized protein can reduce or slow one or more symptoms associated with the genetic disorder. In some embodiments, the stabilized protein is more effective at reducing or slowing one or more symptoms of the genetic disorder, compared to an unstabilized protein. In some embodiments, the genetic disorder is a neurological disorder. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), chronic granulomatous disease (CGD), infantile, juvenile and adult forms of neuronal ceroid lipofuscinosis, and CDKL5 deficiency disease. In some embodiments, the gene therapy vector is a viral vector selected from the group consisting of an adenovirus vector, an adeno-associated virus vector, a retrovirus vector, a lentivirus vector, and a herpes virus vector. In some embodiments, the adeno-associated virus is a serotype selected from the group consisting of: AAV-1, AAV-2, AAV-3, AAV-4, AAV-5, AAV-6, AAV-7, AAV-8, AAV-9, AAV-10, AAV-11, AAV-12, AAV-13, AAV rh.74, AAV-B1 and AAV-hu68. In some embodiments, the nucleic acid construct is comprised in a viral vector genome. In some embodiments, the viral vector genome comprises a recombinant AAV (rAAV) genome. In some embodiments, the rAAV genome comprises a self-complementary genome. In some embodiments, the rAAV genome comprises a single-stranded genome. In some embodiments, the rAAV genome comprises a first inverted terminal repeat and a second inverted terminal repeat. In some embodiments, the AAV inverted terminal repeats are AAV2 inverted terminal repeats. In some embodiments, the rAAV genome further comprises an SV40 intron. In some embodiments, the rAAV genome further comprises a polyadenylation sequence. In some embodiments, the construct further comprises a nucleic acid sequence encoding an α-GAL protein, wherein the nucleic acid sequence is at least 85% identical to one of SEQ ID NOs: 7-12. In some embodiments, the construct further comprises a nucleic acid sequence encoding an α-GAL protein, wherein the α-GAL protein comprises a sequence at least 85% identical to one of SEQ ID NOs: 1-6. In some embodiments, the construct further comprises a nucleic acid sequence encoding an α-GAL protein, wherein the nucleic acid sequence comprises the sequence of one of SEQ ID NOs: 8-12. In some embodiments, the construct further comprises a nucleic acid sequence encoding an α-GAL protein, wherein the α-GAL protein comprises the sequence of one of SEQ ID NOs: 2-6. In some embodiments, the construct further comprises a nucleic acid sequence encoding a PPT1 protein, wherein the nucleic acid sequence is at least 85% identical to one of SEQ ID NOs: 15-16. In some embodiments, the construct further comprises a nucleic acid sequence encoding a PPT1 protein, wherein the PPT1 protein comprises a sequence at least 85% identical to one of SEQ ID NOs: 13-14. In some embodiments, the construct further comprises a nucleic acid sequence encoding a PPT1 protein, wherein the nucleic acid sequence comprises the sequence of SEQ ID NO: 16. In some embodiments, the construct further comprises a nucleic acid sequence encoding a PPT1 protein, wherein the PPT1 protein comprises the sequence of SEQ ID NO: 14. In some embodiments, the construct further comprises a promoter sequence. In some embodiments, the promoter is a constitutive promoter. In some embodiments, the promoter is a tissue-specific promoter. In some embodiments, the construct further comprises one or more nucleic acid sequences selected from the group consisting of: a Kozak sequence, a CrPV IRES, a nucleic acid sequence encoding a linker, a nucleic acid sequence encoding a signal sequence, and a nucleic acid sequence encoding an IGF2 peptide. In some embodiments, the signal peptide sequence comprises a binding immunoglobulin protein (Bip) signal sequence. In some embodiments, the signal peptide sequence comprises the Bip signal sequence comprises an amino acid sequence at least 90% identical to an amino acid sequence selected from the group consisting of SEQ ID NOs: 29-33. In some embodiments, the construct further comprises an internal ribosomal entry sequence (IRES). In some embodiments, the IRES comprises a cricket paralysis virus (CrPV) IRES. In some embodiments, the construct further comprises a nucleic acid sequence encoding a variant IGF2 (vIGF2) peptide. In some embodiments, the vIGF2 peptide comprising an amino acid sequence at least 90% identical to an amino acid sequence selected from the group consisting of SEQ ID NOs: 17-27. In some embodiments, the nucleic acid sequence encoding the vIGF2 peptide is 5' to the nucleic acid sequence encoding the stabilized form of the protein. In some embodiments, the nucleic acid sequence encoding the vIGF2 peptide is 3' to the nucleic acid sequence encoding the stabilized form of the protein. In some embodiments, the construct is packaged within a viral capsid.

In additional aspects, there are provided pharmaceutical compositions comprising a gene therapy vector comprising a nucleic acid construct comprising: a nucleic acid encoding a stabilized form of a protein for treating a genetic disorder and a pharmaceutically acceptable excipient, carrier, or diluent. In some embodiments, the stabilized form comprises one or more non-native cysteine residues that form a disulfide bridge between non-native cysteines within the protein or between non-native cysteines of two monomers of the protein. In some embodiments, the protein is selected from the group consisting of alpha-galactosidase A, β-glucocerebrosidase, glucocerebrosidase, lysosomal acid lipase, glycosaminoglycan alpha-L-iduronidase, alpha-L-iduronidase, N-sulfoglucosamine sulfohydrolase (SGSH), N-acetyl-alpha-glucosaminidase (NAGLU), iduronate-2-sulfatase, N-acetylgalactosamine-6-sulfatase, glycosaminoglycan N-acetylgalactosamine 4-sulfatase, alpha-glucosidase, tripeptidyl peptidase 1 (TPP1), palmitoyl protein thioesterases (PPTs), ceroid lipofuscinoses neuronal 1, ceroid lipofuscinoses neuronal 2, ceroid lipofuscinoses neuronal 3, ceroid lipofuscinoses neuronal 4, ceroid lipofuscinoses neuronal 5, ceroid lipofuscinoses neuronal 6, ceroid lipofuscinoses neuronal 7, ceroid lipofuscinoses neuronal 8, ceroid lipofuscinoses neuronal 9, ceroid lipofuscinoses neuronal 10, ceroid lipofuscinoses neuronal 11, ceroid lipofuscinoses neuronal 12, ceroid lipofuscinoses neuronal 13, ceroid lipofuscinoses neuronal 14, ceroid lipofuscinoses neuronal 15, ceroid lipofuscinoses neuronal 16, and cyclin dependent kinase like 5. In some embodiments, the protein is selected from the group consisting of alpha-galactosidase A, β-glucocerebrosidase, glucocerebrosidase, lysosomal acid lipase, glycosaminoglycan alpha-L-iduronidase, alpha-L-iduronidase, N-sulfoglucosamine sulfohydrolase (SGSH), N-acetyl-alpha-glucosaminidase (NAGLU), iduronate-2-sulfatase, N-acetylgalactosamine-6-sulfatase, glycosaminoglycan N-acetylgalactosamine 4-sulfatase, alpha-glucosidase, tripeptidyl peptidase 1 (TPP1), palmitoyl protein thioesterases (PPTs), ceroid lipofuscinoses neuronal 4, ceroid lipofuscinoses neuronal 10 (cathepsin D), ceroid lipofuscinoses neuronal 11 (progranulin), ceroid lipofuscinoses neuronal 13 (cathepsin F), ceroid lipofuscinoses neuronal 14 (KCTD7), ceroid lipofuscinoses neuronal 15 (TBCK), and cyclin dependent kinase like 5. In some embodiments, the stabilized protein comprises a lysosomal enzyme. In some embodiments, the stabilized protein comprises a stabilized α-galactosidase (α-GAL) protein. In some embodiments, the stabilized α-galactosidase A (α-GAL) protein comprises one or more non-native cysteine residues selected from the group consisting of: (i) D233C and I359C; and (ii) M51C and G360C. In some embodiments, the stabilized protein comprises a stabilized palmitoyl protein thioesterase 1 (PPT1). In some embodiments, the stabilized PPT1 protein comprises non-native cysteine residues A171C and A183C. In some embodiments, the stabilized protein has a longer half-life at pH 7.4 compared to a corresponding protein without the non-native cysteines. In some embodiments, the stabilized protein can replace a protein defective or deficient in the genetic disorder. In some embodiments, the stabilized protein can reduce or slow one or more symptoms associated with the genetic disorder. In some embodiments, the stabilized protein is more effective at reducing or slowing one or more symptoms of the genetic disorder, compared to an unstabilized protein. In some embodiments, the genetic disorder is a neurological disorder. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), chronic granulomatous disease (CGD), infantile, juvenile and adult forms of neuronal ceroid lipofuscinosis, and CDKL5 deficiency disease. In some embodiments, the gene therapy vector is a viral vector selected from the group consisting of an adenovirus vector, an adeno-associated virus vector, a retrovirus vector, a lentivirus vector, and a herpes virus vector. In some embodiments, the adeno-associated virus is a serotype selected from the group consisting of: AAV-1, AAV-2, AAV-3, AAV-4, AAV-5, AAV-6, AAV-7, AAV-8, AAV-9, AAV-10, AAV-11, AAV-12, AAV-13, AAV rh.74, AAV-B1 and AAV-hu68. In some embodiments, the nucleic acid construct is comprised in a viral vector genome. In some embodiments, the viral vector genome comprises a recombinant AAV (rAAV) genome. In some embodiments, the rAAV genome comprises a self-complementary genome. In some embodiments, the rAAV genome comprises a single-stranded genome. In some embodiments, the rAAV genome comprises a first inverted terminal repeat and a second inverted terminal repeat. In some embodiments, the AAV inverted terminal repeats are AAV2 inverted terminal repeats. In some embodiments, the rAAV genome further comprises an SV40 intron. In some embodiments, the rAAV genome further comprises a polyadenylation sequence. In some embodiments, the construct further comprises a nucleic acid sequence encoding an α-GAL protein, wherein the nucleic acid sequence is at least 85% identical to one of SEQ ID NOs: 7-12. In some embodiments, the construct further comprises a nucleic acid sequence encoding an α-GAL protein, wherein the α-GAL protein comprises a sequence at least 85% identical to one of SEQ ID NOs: 1-6. In some embodiments, the construct further comprises a nucleic acid sequence encoding an α-GAL protein, wherein the nucleic acid sequence comprises the sequence of one of SEQ ID NOs: 8-12. In some embodiments, the construct further comprises a nucleic acid sequence encoding an α-GAL protein, wherein the α-GAL protein comprises the sequence of one of SEQ ID NOs: 2-6. In some embodiments, the construct further comprises a nucleic acid sequence encoding a PPT1 protein, wherein the nucleic acid sequence is at least 85% identical to one of SEQ ID NOs: 15-16. In some embodiments, the construct further comprises a nucleic acid sequence encoding a PPT1 protein, wherein the PPT1 protein comprises a sequence at least 85% identical to one of SEQ ID NOs: 13-14. In some embodiments, the construct further comprises a nucleic acid sequence encoding a PPT1 protein, wherein the nucleic acid sequence comprises the sequence of SEQ ID NO: 16. In some embodiments, the construct further comprises a nucleic acid sequence encoding a PPT1 protein, wherein the PPT1 protein comprises the sequence of SEQ ID NO: 14. In some embodiments, the construct further comprises a promoter sequence. In some embodiments, the promoter is a constitutive promoter. In some embodiments, the promoter is a tissue-specific promoter. In some embodiments, the construct further comprises one or more nucleic acid sequences selected from the group consisting of: a Kozak sequence, a CrPV IRES, a nucleic acid sequence encoding a linker, a nucleic acid sequence encoding a signal sequence, and a nucleic acid sequence encoding an IGF2 peptide. In some embodiments, the signal peptide sequence comprises a binding immunoglobulin protein (Bip) signal sequence. In some embodiments, the signal peptide sequence comprises the Bip signal sequence comprises an amino acid sequence at least 90% identical to an amino acid sequence selected from the group consisting of SEQ ID NOs: 29-33. In some embodiments, the construct further comprises an internal ribosomal entry sequence (IRES). In some embodiments, the IRES comprises a cricket paralysis virus (CrPV) IRES. In some embodiments, the construct further comprises a nucleic acid sequence encoding a variant IGF2 (vIGF2) peptide. In some embodiments, the vIGF2 peptide comprising an amino acid sequence at least 90% identical to an amino acid sequence selected from the group consisting of SEQ ID NOs: 17-27. In some embodiments, the nucleic acid sequence encoding the vIGF2 peptide is 5' to the nucleic acid sequence encoding the stabilized form of the protein. In some embodiments, the nucleic acid sequence encoding the vIGF2 peptide is 3' to the nucleic acid sequence encoding the stabilized form of the protein. In some embodiments, the construct is packaged within a viral capsid. In some embodiments, the excipient is selected from the group consisting of saline, maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate.

In further aspects, there are provided methods for treating a genetic disorder in a subject comprising administering to the subject a therapeutically effective amount of a gene therapy vector comprising a nucleic acid construct comprising: a nucleic acid encoding a stabilized form of a protein for treating a genetic disorder or a pharmaceutical compositions thereof. In some embodiments, the stabilized form comprises one or more non-native cysteine residues that form a disulfide bridge between non-native cysteines within the protein or between non-native cysteines of two monomers of the protein. In some embodiments, the protein is selected from the group consisting of alpha-galactosidase A, β-glucocerebrosidase, glucocerebrosidase, lysosomal acid lipase, glycosaminoglycan alpha-L-iduronidase, alpha-L-iduronidase, N-sulfoglucosamine sulfohydrolase (SGSH), N-acetyl-alpha-glucosaminidase (NAGLU), iduronate-2-sulfatase, N-acetylgalactosamine-6-sulfatase, glycosaminoglycan N-acetylgalactosamine 4-sulfatase, alpha-glucosidase, tripeptidyl peptidase 1 (TPP1), palmitoyl protein thioesterases (PPTs), ceroid lipofuscinoses neuronal 1, ceroid lipofuscinoses neuronal 2, ceroid lipofuscinoses neuronal 3, ceroid lipofuscinoses neuronal 4, ceroid lipofuscinoses neuronal 5, ceroid lipofuscinoses neuronal 6, ceroid lipofuscinoses neuronal 7, ceroid lipofuscinoses neuronal 8, ceroid lipofuscinoses neuronal 9, ceroid lipofuscinoses neuronal 10, ceroid lipofuscinoses neuronal 11, ceroid lipofuscinoses neuronal 12, ceroid lipofuscinoses neuronal 13, ceroid lipofuscinoses neuronal 14, ceroid lipofuscinoses neuronal 15, ceroid lipofuscinoses neuronal 16, and cyclin dependent kinase like 5. In some embodiments, the protein is selected from the group consisting of alpha-galactosidase A, β-glucocerebrosidase, glucocerebrosidase, lysosomal acid lipase, glycosaminoglycan alpha-L-iduronidase, alpha-L-iduronidase, N-sulfoglucosamine sulfohydrolase (SGSH), N-acetyl-alpha-glucosaminidase (NAGLU), iduronate-2-sulfatase, N-acetylgalactosamine-6-sulfatase, glycosaminoglycan N-acetylgalactosamine 4-sulfatase, alpha-glucosidase, tripeptidyl peptidase 1 (TPP1), palmitoyl protein thioesterases (PPTs), ceroid lipofuscinoses neuronal 4, ceroid lipofuscinoses neuronal 10 (cathepsin D), ceroid lipofuscinoses neuronal 11 (progranulin), ceroid lipofuscinoses neuronal 13 (cathepsin F), ceroid lipofuscinoses neuronal 14 (KCTD7), ceroid lipofuscinoses neuronal 15 (TBCK), and cyclin dependent kinase like 5. In some embodiments, the stabilized protein comprises a lysosomal enzyme. In some embodiments, the stabilized protein comprises a stabilized α-galactosidase (α-GAL) protein. In some embodiments, the stabilized α-galactosidase A (α-GAL) protein comprises one or more non-native cysteine residues D233C and I359C. In some embodiments, the stabilized protein comprises a stabilized palmitoyl protein thioesterase 1 (PPT1). In some embodiments, the stabilized PPT1 protein comprises non-native cysteine residues A171C and A183C. In some embodiments, the stabilized protein has a longer half-life at pH 7.4 compared to a corresponding protein without the non-native cysteines. In some embodiments, the stabilized protein can replace a protein defective or deficient in the genetic disorder. In some embodiments, the stabilized protein can reduce or slow one or more symptoms associated with the genetic disorder. In some embodiments, the stabilized protein is more effective at reducing or slowing one or more symptoms of the genetic disorder, compared to an unstabilized protein. In some embodiments, the genetic disorder is a neurological disorder. In some embodiments, the genetic disorder is a lysosomal storage disorder. In some embodiments, the genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), chronic granulomatous disease (CGD), infantile, juvenile and adult forms of neuronal ceroid lipofuscinosis, and CDKL5 deficiency disease. In some embodiments, the gene therapy vector is a viral vector selected from the group consisting of an adenovirus vector, an adeno-associated virus vector, a retrovirus vector, a lentivirus vector, and a herpes virus vector. In some embodiments, the adeno-associated virus is a serotype selected from the group consisting of: AAV-1, AAV-2, AAV-3, AAV-4, AAV-5, AAV-6, AAV-7, AAV-8, AAV-9, AAV-10, AAV-11, AAV-12, AAV-13, AAV rh.74, AAV-B1 and AAV-hu68. In some embodiments, the nucleic acid construct is comprised in a viral vector genome. In some embodiments, the viral vector genome comprises a recombinant AAV (rAAV) genome. In some embodiments, In some embodiments, In some embodiments, In some embodiments, In some embodiments, the rAAV genome comprises a self-complementary genome. In some embodiments, the rAAV genome comprises a single-stranded genome. In some embodiments, the rAAV genome comprises a first inverted terminal repeat and a second inverted terminal repeat. In some embodiments, the AAV inverted terminal repeats are AAV2 inverted terminal repeats. In some embodiments, the rAAV genome further comprises an SV40 intron. In some embodiments, the rAAV genome further comprises a poly-adenylation sequence. In some embodiments, the construct further comprises a nucleic acid sequence encoding an α-GAL protein, wherein the nucleic acid sequence is at least 85% identical to one of SEQ ID NOs: 7-12. In some embodiments, the construct further comprises a nucleic acid sequence encoding an α-GAL protein, wherein the α-GAL protein comprises a sequence at least 85% identical to one of SEQ ID NOs: 1-6. In some embodiments, the construct further comprises a nucleic acid sequence encoding an α-GAL protein, wherein the nucleic acid sequence comprises the sequence of one of SEQ ID NOs: 8-12. In some embodiments, the construct further comprises a nucleic acid sequence encoding an α-GAL protein, wherein the α-GAL protein comprises the sequence of one of SEQ ID NOs: 2-6. In some embodiments, the construct further comprises a nucleic acid sequence encoding a PPT1 protein, wherein the nucleic acid sequence is at least 85% identical to one of SEQ ID NOs: 15-16. In some embodiments, the construct further comprises a nucleic acid sequence encoding a PPT1 protein, wherein the PPT1 protein comprises a sequence at least 85% identical to one of SEQ ID NOs: 13-14. In some embodiments, the construct further comprises a nucleic acid sequence encoding a PPT1 protein, wherein the nucleic acid sequence comprises the sequence of SEQ ID NO: 16. In some embodiments, the construct further comprises a nucleic acid sequence encoding a PPT1 protein, wherein the PPT1 protein comprises the sequence of SEQ ID NO: 14. In some embodiments, the construct further comprises a promoter sequence. In some embodiments, the promoter is a constitutive promoter. In some embodiments, the promoter is a tissue-specific promoter. In some embodiments, the construct further comprises one or more nucleic acid sequences selected from the group consisting of: a Kozak sequence, a CrPV IRES, a nucleic acid sequence encoding a linker, a nucleic acid sequence encoding a signal sequence, and a nucleic acid sequence encoding an IGF2 peptide. In some embodiments, the signal peptide sequence comprises a binding immunoglobulin protein (Bip) signal sequence. In some embodiments, the signal peptide sequence comprises the Bip signal sequence comprises an amino acid sequence at least 90% identical to an amino acid sequence selected from the group consisting of SEQ ID NOs: 29-33. In some embodiments, the construct further comprises an internal ribosomal entry sequence (IRES). In some embodiments, the IRES comprises a cricket paralysis virus (CrPV) IRES. In some embodiments, the construct further comprises a nucleic acid sequence encoding a variant IGF2 (vIGF2) peptide. In some embodiments, the vIGF2 peptide comprising an amino acid sequence at least 90% identical to an amino acid sequence selected from the group consisting of SEQ ID NOs: 17-27. In some embodiments, the nucleic acid sequence encoding the vIGF2 peptide is 5' to the nucleic acid sequence encoding the stabilized form of the protein. In some embodiments, the nucleic acid sequence encoding the vIGF2 peptide is 3' to the nucleic acid sequence encoding the stabilized form of the protein. In some embodiments, the construct is packaged within a viral capsid. In some embodiments, the gene therapy vector or pharmaceutical composition is delivered by intrathecal, intracerebroventricular, intraparenchymal, or intravenous injection, or a combination thereof. In some embodiments, the gene therapy vector or pharmaceutical composition reduces or slows one or more symptoms of the genetic disorder in the subject. In some embodiments, the genetic disorder is a lysosomal storage disorder. In some embodiments, the genetic disorder is selected from the group consisting of aspartylglucosaminuria, batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), chronic granulomatous disease (CGD), neuronal ceroid lipofuscinosis, and CDKL5 deficiency disorder.

In additional aspects, there are provided stabilized human α-galactosidase A (α-GAL) dimers. In some embodiments stabilized α-GAL dimers comprise one or more non-native cysteine residues, wherein the one or more non-native cysteine residues form at least one intermolecular disulfide bond connecting a first subunit and a second subunit of the α-GAL dimer. In some embodiments, the one or more non-native cysteine residues are selected from the group consisting of: (i) D233C and I359C; and (ii) M51C and G360C. In some embodiments, the one or more non-native cysteine residues comprise D233C and I359C. In some embodiments, the one or more non-native cysteine residues comprise M51C and G360C. In some embodiments, the one or more non-native cysteine residues comprise i) D233C and I359C; and (ii) M51C and G360C. In some embodiments, the polypeptide has a sequence at least 90% identical to one of SEQ ID NOs: 1-6. In some embodiments, the polypeptide is encoded by a nucleic acid at least 85% identical to one of SEQ ID NOs: 7-12. In some embodiments, the polypeptide shows increased half-life at pH 7.4 compared with a wild type α-GAL polypeptide. In some embodiments, the polypeptide further comprises a variant IGF2 (vIGF2) peptide.

In further aspects, there are provided pharmaceutical compositions comprising stabilized human α-GAL dimers and a pharmaceutically acceptable excipient, carrier, or diluent. In some embodiments stabilized α-GAL dimers comprise one or more non-native cysteine residues, wherein the one or more non-native cysteine residues form at least one intermolecular disulfide bond connecting a first subunit and a second subunit of the α-GAL dimer. In some embodiments, the one or more non-native cysteine residues are selected from the group consisting of: (i) D233C and I359C; and (ii) M51C and G360C. In some embodiments, the one or more non-native cysteine residues comprise D233C and I359C. In some embodiments, the one or more non-native cysteine residues comprise M51C and G360C. In some embodiments, the one or more non-native cysteine residues comprise i) D233C and I359C; and (ii) M51C and G360C. In some embodiments, the polypeptide has a sequence at least 90% identical to one of SEQ ID NOs: 1-6. In some embodiments, the polypeptide is encoded by a nucleic acid at least 85% identical to one of SEQ ID NOs: 7-12. In some embodiments, the polypeptide shows increased half-life at pH 7.4 compared with a wild type α-GAL polypeptide. In some embodiments, the polypeptide further comprises a variant IGF2 (vIGF2) peptide. In some embodiments, the excipient is selected from the group consisting of saline, maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate.

In additional aspects, there are provided methods for treating Fabry disease in a subject comprising administering to the subject a therapeutically effective amount of a stabilized human α-GAL dimer or pharmaceutical composition thereof to a subject in need thereof. In some embodiments stabilized α-GAL dimers comprise one or more non-native cysteine residues, wherein the one or more non-native cysteine residues form at least one intermolecular disulfide bond connecting a first subunit and a second subunit of the α-GAL dimer. In some embodiments, the one or more non-native cysteine residues are selected from the group consisting of: (i) D233C and I359C; and (ii) M51C and G360C. In some embodiments, the one or more non-native cysteine residues comprise D233C and I359C. In some embodiments, the one or more non-native cysteine residues comprise M51C and G360C. In some embodiments, the one or more non-native cysteine residues comprise i) D233C and I359C; and (ii) M51C and G360C. In some embodiments, the polypeptide has a sequence at least 90% identical to one of SEQ ID NOs: 1-6. In some embodiments, the polypeptide is encoded by a nucleic acid at least 85% identical to one of SEQ ID NOs: 7-12. In some embodiments, the polypeptide shows increased half-life at pH 7.4 compared with a wild type α-GAL polypeptide. In some embodiments, the polypeptide further comprises a variant IGF2 (vIGF2) peptide. In some embodiments, the excipient is selected from the group consisting of saline, maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate. In some embodiments, the stabilized human α-GAL dimer or pharmaceutical composition is delivered by intrathecal, intracerebroventricular, intraperenchymal, subcutaneous, intramuscular, ocular, intravenous injection, or a combination thereof. In some embodiments, the stabilized human α-GAL dimer or pharmaceutical composition reduces or slows one or more symptoms of the Fabry disease in the subject.

In additional aspects, there are provided stabilized human palmitoyl protein thioesterase 1 (PPT1) molecules. In some embodiments, the stabilized PPT1 molecule comprises one or more non-native cysteine residues wherein the one or more non-native cysteine residues form at least one intramolecular disulfide bond within the PPT1 molecule. In some embodiments, the stabilized PPT1 comprises non-native cysteine residues A171C and A183C. In some embodiments, the polypeptide has a sequence at least 90% identical to one of SEQ ID NOs: 13-14. In some embodiments, the polypeptide is encoded by a nucleic acid at least 85% identical to one of SEQ ID NOs: 15-16. In some embodiments, the polypeptide shows increased half-life at pH 7.4 compared with a wild type PPT1 polypeptide. In some embodiments, the polypeptide further comprises a variant IGF2 (vIGF2) peptide.

In further aspects, there are provided pharmaceutical compositions comprising a stabilized PPT1 and a pharmaceutically acceptable excipient, carrier, or diluent. In some embodiments, the stabilized PPT1 molecule comprises one or more non-native cysteine residues wherein the one or more non-native cysteine residues form at least one intramolecular disulfide bond within the PPT1 molecule. In some embodiments, the stabilized PPT1 comprises non-native cysteine residues A171C and A183C. In some embodiments, the polypeptide has a sequence at least 90% identical to one of SEQ ID NOs: 13-14. In some embodiments, the polypeptide is encoded by a nucleic acid at least 85% identical to one of SEQ ID NOs: 15-16. In some embodiments, the polypeptide shows increased half-life at pH 7.4 compared with a wild type PPT1 polypeptide. In some embodiments, the polypeptide further comprises a variant IGF2 (vIGF2) peptide. In some embodiments, the excipient is selected from the group consisting of saline, maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate.

In additional aspects, there are provided methods for treating CLN1 disease in a subject comprising administering to the subject a therapeutically effective amount of a stabilized PPT1 or a pharmaceutical composition thereof to a subject in need thereof. In some embodiments, the stabilized PPT1 molecule comprises one or more non-native cysteine residues wherein the one or more non-native cysteine residues form at least one intramolecular disulfide bond within the PPT1 molecule. In some embodiments, the stabilized PPT1 comprises non-native cysteine residues A171C and A183C. In some embodiments, the polypeptide has a sequence at least 90% identical to one of SEQ ID NOs: 13-14. In some embodiments, the polypeptide is encoded by a nucleic acid at least 85% identical to one of SEQ ID NOs: 15-16. In some embodiments, the polypeptide shows increased half-life at pH 7.4 compared with a wild type PPT1 polypeptide. In some embodiments, the polypeptide further comprises a variant IGF2 (vIGF2) peptide. In some embodiments, the excipient is selected from the group consisting of saline, maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate. In some embodiments, the modified PPT1 or pharmaceutical composition is delivered by intrathecal, intracerebroventricular, intraperenchymal, subcutaneous, intramuscular, ocular, intravenous injection, or a combination thereof.

In additional aspects, there are provided modified human α-galactosidase A (α-GAL) polypeptides comprising cysteine substitutions of an α-GAL polypeptide sequence selected from the group consisting of: (i) D233C and I359C; and (ii) M51C and G360C. In some embodiments, the polypeptide comprises cysteine substitutions of an α-GAL polypeptide sequence of D233C and I359C. In some embodiments, the polypeptide comprises cysteine substitutions of an α-GAL polypeptide sequence of M51C and G360C. In some embodiments, the polypeptide forms a homodimer. In some embodiments, the homodimer is stabilized by a disulfide bond. In some embodiments, the polypeptide shows increased half-life at pH 7.4 compared with a wild type α-GAL polypeptide.

In further aspects, there are provided, nucleic acid molecules comprising a nucleic acid encoding a modified human α-GAL polypeptide. In some embodiments, the modified human α-GAL polypeptide comprises cysteine substitutions of an α-GAL polypeptide sequence selected from the group consisting of: (i) D233C and I359C; and (ii) M51C and G360C. In some embodiments, the polypeptide comprises cysteine substitutions of an α-GAL polypeptide sequence of D233C and I359C. In some embodiments, the polypeptide comprises cysteine substitutions of an α-GAL polypeptide sequence of M51C and G360C. In some embodiments, the polypeptide forms a homodimer. In some embodiments, the homodimer is stabilized by a disulfide bond. In some embodiments, the polypeptide shows increased half-life at pH 7.4 compared with a wild type α-GAL polypeptide.

In further aspects, there are provided gene therapy vectors comprising a nucleic acid molecule comprising a nucleic acid encoding a modified human α-GAL polypeptide. In some embodiments, the modified human α-GAL polypeptide comprises cysteine substitutions of an α-GAL polypeptide sequence selected from the group consisting of: (i) D233C and I359C; and (ii) M51C and G360C. In some embodiments, the polypeptide comprises cysteine substitutions of an α-GAL polypeptide sequence of D233C and I359C. In some embodiments, the polypeptide comprises cysteine substitutions of an α-GAL polypeptide sequence of M51C and G360C. In some embodiments, the polypeptide forms a homodimer. In some embodiments, the homodimer is stabilized by a disulfide bond. In some embodiments, the polypeptide shows increased half-life at pH 7.4 compared with a wild type α-GAL polypeptide.

In additional aspects, there are provided, modified human α-galactosidase A (α-GAL) polypeptides comprising cysteine substitutions of an α-GAL polypeptide sequence, wherein the cysteine substitutions facilitate disulfide bond formation between two α-GAL polypeptides to form a homodimer. In some embodiments, the polypeptide comprises cysteine substitutions of an α-GAL polypeptide sequence selected from the group consisting of: (i) D233C and I359C; and (ii) M51C and G360C. In some embodiments, the polypeptide comprises cysteine substitutions of an α-GAL polypeptide sequence of D233C and I359C. In some embodiments, the polypeptide comprises cysteine substitutions of an α-GAL polypeptide sequence of M51C and G360C. In some embodiments, the polypeptide shows increased half-life at pH 7.4 compared with a wild type α-GAL polypeptide.

In further aspects, there are provided nucleic acid molecule comprising a nucleic acid encoding a modified human α-GAL polypeptide. In some embodiments, the modified human α-galactosidase A (α-GAL) polypeptides comprise cysteine substitutions of an α-GAL polypeptide sequence, wherein the cysteine substitutions facilitate disulfide bond formation between two α-GAL polypeptides to form a homodimer. In some embodiments, the polypeptide comprises cysteine substitutions of an α-GAL polypeptide sequence selected from the group consisting of: (i) D233C and I359C; and (ii) M51C and G360C. In some embodiments, the polypeptide comprises cysteine substitutions of an α-GAL polypeptide sequence of D233C and I359C. In some embodiments, the polypeptide comprises cysteine substitutions of an α-GAL polypeptide sequence of M51C and G360C. In some embodiments, the polypeptide shows increased half-life at pH 7.4 compared with a wild type α-GAL polypeptide.

In additional aspects, there are provided gene therapy vectors comprising a nucleic acid encoding a modified human α-GAL polypeptide. In some embodiments, the modified human α-galactosidase A (α-GAL) polypeptide comprises cysteine substitutions of an α-GAL polypeptide sequence, wherein the cysteine substitutions facilitate disulfide bond formation between two α-GAL polypeptides to form a homodimer. In some embodiments, the polypeptide comprises cysteine substitutions of an α-GAL polypeptide sequence selected from the group consisting of: (i) D233C and I359C; and (ii) M51C and G360C. In some embodiments, the polypeptide comprises cysteine substitutions of an α-GAL polypeptide sequence of D233C and I359C. In some embodiments, the polypeptide comprises cysteine substitutions of an α-GAL polypeptide sequence of M51C and G360C. In some embodiments, the polypeptide shows increased half-life at pH 7.4 compared with a wild type α-GAL polypeptide.

In further aspects, there are provided homodimers comprising two modified human α-GAL polypeptides, wherein each modified human α-GAL polypeptide comprises cysteine substitutions of an α-GAL polypeptide sequence selected from the group consisting of: (i) D233C and I359C; and (ii) M51C and G360C. In some embodiments, each modified human α-GAL polypeptide comprises cysteine substitutions of an α-GAL polypeptide sequence of D233C and I359C. In some embodiments, each modified human α-GAL polypeptide comprises cysteine substitutions of an α-GAL polypeptide sequence of M51C and G360C. In some embodiments, the homodimer is stabilized by a disulfide bond. In some embodiments, the homodimer shows increased half-life at pH 7.4 compared with a wild type α-GAL homodimer.

In additional aspects, there are provided homodimers comprising two modified human α-GAL polypeptides, wherein each modified human α-GAL polypeptide comprises cysteine substitutions of an α-GAL polypeptide sequence, wherein the cysteine substitutions facilitate disulfide bond formation between two α-GAL polypeptides to form a homodimer. In some embodiments, the polypeptide comprises cysteine substitutions of an α-GAL polypeptide sequence selected from the group consisting of: (i) D233C and I359C; and (ii) M51C and G360C. In some embodiments, each modified human α-GAL polypeptide comprises cysteine substitutions of an α-GAL polypeptide sequence of D233C and I359C. In some embodiments, each modified human α-GAL polypeptide comprises cysteine substitutions of an α-GAL polypeptide sequence of M51C and G360C. In some embodiments, the homodimer is stabilized by a disulfide bond. In some embodiments, the homodimer shows increased half-life at pH 7.4 compared with a wild type α-GAL homodimer.

In further aspects, there are provided nucleic acid molecules comprising a nucleic acid encoding a modified α-GAL polypeptide, wherein the nucleic acid encodes a polypeptide comprising cysteine substitutions of an α-GAL polypeptide sequence selected from the group consisting of: (i) D233C and I359C; and (ii) M51C and G360C. In some embodiments, the nucleic acid encodes a polypeptide comprising cysteine substitutions of D233C and I359C. In some embodiments, the nucleic acid encodes a polypeptide comprising cysteine substitutions of M51C and G360C. In some embodiments, the polypeptide forms a homodimer. In some embodiments, the homodimer is stabilized by a disulfide bond. In some embodiments, the polypeptide shows increased half-life at pH 7.4 compared with a wild type α-GAL polypeptide. In some embodiments, the nucleic acid is a gene therapy construct. In some embodiments, the nucleic acid further comprises a promoter. In some embodiments, the promoter is a constitutive promoter. In some embodiments, the promoter is a tissue-specific promoter. In some embodiments, the nucleic acid comprises at least a portion of a virus nucleic acid sequence. In some embodiments, the virus is selected from wherein the virus comprises a retrovirus, an adenovirus, an adeno associated virus, a lentivirus, or a herpes virus.

In additional aspects, there are provided nucleic acid molecules comprising a nucleic acid encoding a modified human α-GAL polypeptide, wherein the nucleic acid encodes a polypeptide comprising cysteine substitutions of an α-GAL polypeptide sequence, wherein the cysteine substitutions facilitate disulfide bond formation between two α-GAL polypeptides to form a homodimer. In some embodiments, the polypeptide comprises cysteine substitutions of an α-GAL polypeptide sequence selected from the group consisting of: (i) D233C and I359C; and (ii) M51C and G360C. In some embodiments, the nucleic acid encodes a polypeptide comprising cysteine substitutions of D233C and I359C. In some embodiments, the nucleic acid encodes a polypeptide comprising cysteine substitutions of M51C and G360C. In some embodiments, the polypeptide forms a homodimer. In some embodiments, the homodimer is stabilized by a disulfide bond. In some embodiments, the polypeptide shows increased half-life at pH 7.4 compared with a wild type α-GAL polypeptide. In some embodiments, the nucleic acid is a gene therapy construct. In some embodiments, the nucleic acid further comprises a promoter. In some embodiments, the promoter is a constitutive promoter. In some embodiments, the promoter is a tissue-specific promoter. In some embodiments, the nucleic acid comprises at least a portion of a virus nucleic acid sequence. In some embodiments, the virus is selected from wherein the virus comprises a retrovirus, an adenovirus, an adeno associated virus, a lentivirus, or a herpes virus.

In additional aspects, there are provided nucleic acid constructs comprising at least one promoter and a nucleic acid encoding a modified human α-GAL polypeptide, wherein the modified human α-GAL polypeptide comprises cysteine substitutions of an α-GAL polypeptide sequence selected from the group consisting of: (i) D233C and I359C; and (ii) M51C and G360C. In some embodiments, the nucleic acid encodes a polypeptide comprising cysteine substitutions of an α-GAL polypeptide sequence of D233C and I359C. In some embodiments, the nucleic acid encodes a polypeptide comprising cysteine substitutions of an α-GAL polypeptide sequence of M51C and G360C. In some embodiments, the promoter is a constitutive promoter. In some embodiments, the promoter is a tissue-specific promoter. In some embodiments, the nucleic acid construct comprises one or more nucleic acids from the group consisting of: a CrPV IRES, a kozak sequence, a nucleic acid encoding a linker, a nucleic acid sequence encoding a leader sequence, and a nucleic acid encoding a IGF2 peptide. In some embodiments, the nucleic acid construct comprises at least a portion of a virus nucleic acid sequence. In some embodiments, the virus comprises a retrovirus, an adenovirus, an adeno associated virus, a lentivirus, or a herpes virus. In some embodiments, the polypeptide forms a homodimer. In some embodiments, the homodimer is stabilized by a disulfide bond. In some embodiments, the polypeptide shows increased half-life at pH 7.4 compared with a wild type α-GAL polypeptide. In some embodiments, the nucleic acid is packaged within in a viral capsid protein. In some embodiments, the nucleic acid construct is suitable for gene therapy.

In further aspects, there are provided nucleic acid constructs comprising at least one promoter and a nucleic acid encoding a modified human α-GAL polypeptide, wherein the modified human α-GAL polypeptide comprises cysteine substitutions of an α-GAL polypeptide sequence, wherein the cysteine substitutions facilitate disulfide bond formation between two α-GAL polypeptides to form a homodimer. In some embodiments, the polypeptide comprises cysteine substitutions of an α-GAL polypeptide sequence selected from the group consisting of: (i) D233C and I359C; and (ii)

M51C and G360C. In some embodiments, the nucleic acid encodes a polypeptide comprising cysteine substitutions of an α-GAL polypeptide sequence of D233C and I359C. In some embodiments, the nucleic acid encodes a polypeptide comprising cysteine substitutions of an α-GAL polypeptide sequence of M51C and G360C. In some embodiments, the promoter is a constitutive promoter. In some embodiments, the promoter is a tissue-specific promoter. In some embodiments, the nucleic acid construct comprises one or more nucleic acids from the group consisting of: a CrPV IRES, a kozak sequence, a nucleic acid encoding a linker, a nucleic acid sequence encoding a leader sequence, and a nucleic acid encoding a IGF2 peptide. In some embodiments, the nucleic acid construct comprises at least a portion of a virus nucleic acid sequence. In some embodiments, the virus comprises a retrovirus, an adenovirus, an adeno associated virus, a lentivirus, or a herpes virus. In some embodiments, the polypeptide forms a homodimer. In some embodiments, the homodimer is stabilized by a disulfide bond. In some embodiments, the polypeptide shows increased half-life at pH 7.4 compared with a wild type α-GAL polypeptide. In some embodiments, the nucleic acid is packaged within in a viral capsid protein. In some embodiments, the nucleic acid construct is suitable for gene therapy.

In further aspects, there are provided pharmaceutical compositions comprising (a) a modified human α-GAL polypeptide, wherein the modified human α-GAL polypeptide comprises cysteine substitutions of an α-GAL polypeptide sequence selected from the group consisting of: (i) D233C and I359C; and (ii) M51C and G360C and (b) a pharmaceutically acceptable excipient. In some embodiments, the modified human α-GAL polypeptide comprises cysteine substitutions of an α-GAL polypeptide sequence of D233C and I359C. In some embodiments, the modified human α-GAL polypeptide comprises cysteine substitutions of an α-GAL polypeptide sequence of M51C and G360C. In some embodiments, the modified human α-GAL polypeptide forms a homodimer. In some embodiments, the homodimer is stabilized by a disulfide bond. In some embodiments, the modified human α-GAL polypeptide shows increased half-life at pH 7.4 compared with a wild type α-GAL polypeptide. In some embodiments, the excipient is selected from the group consisting of saline, maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate. In some embodiments, the composition is suitable for enzyme replacement therapy.

In additional aspects, there are provided methods of ameliorating at least one symptom of Fabry disease in a subject in need thereof, the method comprising administering at least one dose of a composition comprising a gene therapy nucleic acid construct comprising at least one promoter and a nucleic acid encoding a modified human α-GAL polypeptide, wherein the modified human α-GAL polypeptide comprises cysteine substitutions of an α-GAL polypeptide sequence selected from the group consisting of: (i) D233C and I359C; and (ii) M51C and G360C. In some embodiments, the nucleic acid encodes a polypeptide comprising cysteine substitutions of an α-GAL polypeptide sequence of D233C and I359C. In some embodiments, the nucleic acid encodes a polypeptide comprising cysteine substitutions of an α-GAL polypeptide sequence of M51C and G360C. In some embodiments, the nucleic acid encodes a polypeptide which forms a homodimer. In some embodiments, the homodimer is stabilized by a disulfide bond. In some embodiments, the nucleic acid encodes a modified human α-GAL polypeptide having increased half-life at pH 7.4 compared with a wild type α-GAL polypeptide. In some embodiments, the promoter is a constitutive promoter. In some embodiments, the promoter is a tissue-specific promoter. In some embodiments, the nucleic acid comprises at least a portion of a virus. In some embodiments, the virus is selected from wherein the virus comprises a retrovirus, an adenovirus, an adeno associated virus, a lentivirus, or a herpes virus. In some embodiments, the nucleic acid is packaged within in a viral capsid protein. In some embodiments, the at least one symptom is selected from one or more of pain, skin discoloration, inability to sweat, eye cloudiness, gastrointestinal dysfunction, tinnitus, hearing loss, mitral valve prolapse, heart disease, joint pain, renal failure, and kidney dysfunction. In some embodiments, at least one symptom is reduced with a single administration of the gene therapy nucleic acid construct. In some embodiments, the method further comprises measuring an α-GAL activity in a tissue obtained from the subject following treatment.

In further aspects, there are provided methods of ameliorating at least one symptom of Fabry disease in a subject in need thereof, the method comprising administering at least one dose of a composition comprising a modified α-GAL polypeptide, wherein the modified human α-GAL polypeptide comprises cysteine substitutions of an α-GAL polypeptide sequence selected from the group consisting of: (i) D233C and I359C; and (ii) M51C and G360C. In some embodiments, the modified human α-GAL polypeptide cysteine substitutions of an α-GAL polypeptide sequence of D233C and I359C. In some embodiments, the modified human α-GAL polypeptide cysteine substitutions of an α-GAL polypeptide sequence of M51C and G360C. In some embodiments, the modified human α-GAL polypeptide forms a homodimer. In some embodiments, the homodimer is stabilized by a disulfide bond. In some embodiments, the modified human α-GAL polypeptide shows increased half-life at pH 7.4 compared with a wild type α-GAL polypeptide. In some embodiments, the at least one symptom is selected from one or more of pain, skin discoloration, inability to sweat, eye cloudiness, gastrointestinal dysfunction, tinnitus, hearing loss, mitral valve prolapse, heart disease, joint pain, renal failure, and kidney dysfunction.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

An understanding of the features and advantages of the present invention will be obtained by reference to the following detailed description that sets forth illustrative embodiments, in which the principles of the invention are utilized, and the accompanying drawings of which.

DETAILED DESCRIPTION

Figure 1A:
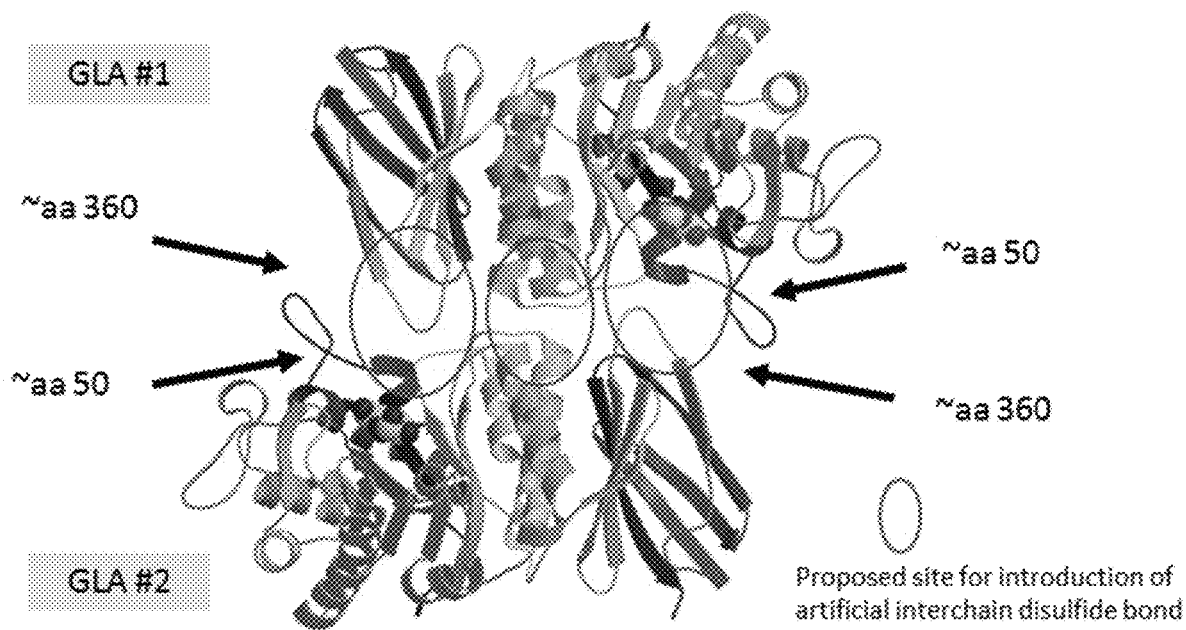
FIG. 1A and FIG. 1B show the structure of α-galactosidase A (α-GAL) and the proposed sites of amino acid substitutions.

Provided herein are variants of polypeptides for therapeutics including constructs for gene therapy having cysteine substitutions which enable stabilization due to formation of disulfide bonds within the molecule or to disulfide bonds forming between the two subunits in the polypeptide to form a dimer. These disulfide bonds result in a more stable recombinant enzyme at neutral pH, such as the pH of blood. Accordingly, a more stable polypeptide with longer half-life is provided that is useful for treatment of diseases resulting from mutations, including diseases resulting from mutation of α-GAL, such as Fabry disease; or mutation of PPT-1, such as CLN1 disease. Polypeptide variants (also termed "modified polypeptides") herein include but are not limited to variants of α-GAL and PPT-1.

Modified α-GAL Polypeptides

Provided herein are modified α-GAL polypeptides comprising cysteine substitutions of an α-GAL polypeptide sequence. Contemplated substitutions provided herein include: (i) R49C and G361C; (ii) R49C and G360C; (iii) D233C and I359C; (iv) M51C and G360C; and (v) S276C. In some embodiments, the polypeptide comprises cysteine substitutions of an α-GAL polypeptide sequence selected from the group consisting of: (i) D233C and I359C; and (ii) M51C and G360C. In some embodiments, the polypeptide comprises cysteine substitutions of an α-GAL polypeptide sequence of D233C and I359C. In some embodiments, the polypeptide comprises cysteine substitutions of an α-GAL polypeptide sequence of M51C and G360C. The modified α-GAL polypeptides a can form a homodimer is stabilized by at least one, more preferably two intermolecular disulfide bonds. The modified α-GAL polypeptides polypeptide shows increased half-life at pH 7.4 compared with a wildtype α-GAL polypeptide.

Wild type and exemplary Modified α-GAL sequences are provided in Table 1

TABLE 1 a-GAL Polypeptide Sequences

| α-GAL variant | Sequence | SEQ ID NO: |
|---|---|---|
| Human α-GAL wild type (NP_000160.1) | MQLRNPELHLGCALALRFLALVSWDIPGARALDNGLARTPTMGWLHWERFMCN LDCQEEPDSCISEKLFMEMAELMVSEGWKDAGYEYLCIDDCWMAPQRDSEGRL QADPQRFPHGIRQLANYVHSKGLKLGIYADVGNKTCAGFPGSFGYYDIDAQTFA DWGVDLLKFDGCYCDSLENLADGYKHMSLALNRTGRSIVYSCEWPLYMWPFQK PNYTEIRQYCNHWRNFADIDDSWKSIKSILDWTSFNQERIVDVAGPGGWNDPDM LVIGNFGLSWNQQVTQMALWAIMAAPLFMSNDLRHISPQAKALLQDKDVIAINQ DPLGKQGYQLRQGDNFEVWERPLSGLAWAVAMINRQEIGGPRSYTIAVASLGKG VACNPACFITQLLPVKRKLGFYEWTSRLRSHINPTGTVLLQLENTMQMSLKDLL | 1 |
| Human α-GAL R49C-G361C | MQLRNPELHLGCALALRFLALVSWDIPGARALDNGLARTPTMGWLHWECFMCN LDCQEEPDSCISEKLFMEMAELMVSEGWKDAGYEYLCIDDCWMAPQRDSEGRL QADPQRFPHGIRQLANYVHSKGLKLGIYADVGNKTCAGFPGSFGYYDIDAQTFA DWGVDLLKFDGCYCDSLENLADGYKHMSLALNRTGRSIVYSCEWPLYMWPFQK PNYTEIRQYCNHWRNFADIDDSWKSIKSILDWTSFNQERIVDVAGPGGWNDPDM LVIGNFGLSWNQQVTQMALWAIMAAPLFMSNDLRHISPQAKALLQDKDVIAINQ DPLGKQGYQLRQGDNFEVWERPLSGLAWAVAMINRQEIGCPRSYTIAVASLGKG VACNPACFITQLLPVKRKLGFYEWTSRLRSHINPTGTVLLQLENTMQMSLKDLL | 2 |
| Human A-GAL R49C-G360C | MQLRNPELHLGCALALRFLALVSWDIPGARALDNGLARTPTMGWLHWECFMCN LDCQEEPDSCISEKLFMEMAELMVSEGWKDAGYEYLCIDDCWMAPQRDSEGRL QADPQRFPHGIRQLANYVHSKGLKLGIYADVGNKTCAGFPGSFGYYDIDAQTFA DWGVDLLKFDGCYCDSLENLADGYKHMSLALNRTGRSIVYSCEWPLYMWPFQK PNYTEIRQYCNHWRNFADIDDSWKSIKSILDWTSFNQERIVDVAGPGGWNDPDM LVIGNFGLSWNQQVTQMALWAIMAAPLFMSNDLRHISPQAKALLQDKDVIAINQ DPLGKQGYQLRQGDNFEVWERPLSGLAWAVAMINRQEICGPRSYTIAVASLGKG VACNPACFITQLLPVKRKLGFYEWTSRLRSHINPTGTVLLQLENTMQMSLKDLL | 3 |
| Human α-GAL M51C-G360C | MQLRNPELHLGCALALRFLALVSWDIPGARALDNGLARTPTMGWLHWERFCCN LDCQEEPDSCISEKLFMEMAELMVSEGWKDAGYEYLCIDDCWMAPQRDSEGRL QADPQRFPHGIRQLANYVHSKGLKLGIYADVGNKTCAGFPGSFGYYDIDAQTFA DWGVDLLKFDGCYCDSLENLADGYKHMSLALNRTGRSIVYSCEWPLYMWPFQK PNYTEIRQYCNHWRNFADIDDSWKSIKSILDWTSFNQERIVDVAGPGGWNDPDM LVIGNFGLSWNQQVTQMALWAIMAAPLFMSNDLRHISPQAKALLQDKDVIAINQ DPLGKQGYQLRQGDNFEVWERPLSGLAWAVAMINRQEICGPRSYTIAVASLGKG VACNPACFITQLLPVKRKLGFYEWTSRLRSHINPTGTVLLQLENTMQMSLKDLL | 4 |

TABLE 1-continued a-GAL Polypeptide Sequences

| α-GAL variant | Sequence | SEQ ID NO: |
|---|---|---|
| Human α-GAL D233C-I359C | MQLRNPELHLGCALALRFLALVSWDIPGARALDNGLARTPTMGWLHWERFMCN<br>LDCQEEPDSCISEKLFMEMAELMVSEGWKDAGYEYLCIDDCWMAPQRDSEGRL<br>QADPQRFPHGIRQLANYVHSKGLKLGIYADVGNKTCAGFPGSFGYYDIDAQTFA<br>DWGVDLLKFDGCYCDSLENLADGYKHMSLALNRTGRSIVYSCEWPLYMWPFQK<br>PNYTEIRQYCNHWRNFADI<u>C</u>DSWKSIKSILDWTSFNQERIVDVAGPGGWNDPDM<br>LVIGNFGLSWNQQVTQMALWAIMAAPLFMSNDLRHISPQAKALLQDKDVIAINQ<br>DPLGKQGYQLRQGDNFEVWERPLSGLAWAVAMINRQE<u>C</u>GGPRSYTIAVASLGK<br>GVACNPACFITQLLPVKRKLGFYEWTSRLRSHINPTGTVLLQLENTMQMSLKDLL | 5 |
| Human α-GAL S276C | MQLRNPELHLGCALALRFLALVSWDIPGARALDNGLARTPTMGWLHWERFMCN<br>LDCQEEPDSCISEKLFMEMAELMVSEGWKDAGYEYLCIDDCWMAPQRDSEGRL<br>QADPQRFPHGIRQLANYVHSKGLKLGIYADVGNKTCAGFPGSFGYYDIDAQTFA<br>DWGVDLLKFDGCYCDSLENLADGYKHMSLALNRTGRSIVYSCEWPLYMWPFQK<br>PNYTEIRQYCNHWRNFADIDDSWKSIKSILDWTSFNQERIVDVAGPGGWNDPDM<br>LVIGNFGL<u>C</u>WNQQVTQMALWAIMAAPLFMSNDLRHISPQAKALLQD<u>C</u>DVIAINQ<br>DPLGKQGYQLRQGDNFEVWERPLSGLAWAVAMINRQEIGGPRSYTIAVASLGKG<br>VACNPACFITQLLPVKRKLGFYEWTSRLRSHINPTGTVLLQLENTMQMSLKDLL | 6 |

Also provided herein are modified α-GAL polypeptides comprising a polypeptide with a sequence containing cysteine residues at positions 51 and 360 and having at least 90% identity to a sequence set forth as SEQ ID NO: 4. In some embodiments, modified α-GAL polypeptides comprise a polypeptide with a sequence containing cysteine residues at positions 51 and 360 and having at least 95% identity to a sequence set forth as SEQ ID NO: 4. In some embodiments, modified α-GAL polypeptides comprise a polypeptide with a sequence containing cysteine residues at positions 51 and 360 and having at least 96% identity to a sequence set forth as SEQ ID NO: 4. In some embodiments, modified α-GAL polypeptides comprise a polypeptide with a sequence containing cysteine residues at positions 51 and 360 and having at least 97% identity to a sequence set forth as SEQ ID NO: 4. In some embodiments, modified α-GAL polypeptides comprise a polypeptide with a sequence containing cysteine residues at positions 51 and 360 and having at least 98% identity to a sequence set forth as SEQ ID NO: 4. In some embodiments, modified α-GAL polypeptides comprise a polypeptide with a sequence containing cysteine residues at positions 51 and 360 and having at least 99% identity to a sequence set forth as SEQ ID NO: 4. In some embodiments, modified α-GAL polypeptides comprise a polypeptide with a sequence containing cysteine residues at positions 51 and 360 and having more than 99% identity to a sequence set forth as SEQ ID NO: 4. In some embodiments, modified α-GAL polypeptides comprise a polypeptide with a sequence set forth as SEQ ID NO: 4.

Also provided herein are modified α-GAL polypeptides comprising a polypeptide with a sequence containing cysteine residues at positions 233 and 359 and having at least 90% identity to a sequence set forth as SEQ ID NO: 5. In some embodiments, modified α-GAL polypeptides comprise a polypeptide with a sequence containing cysteine residues at positions 233 and 359 and having at least 95% identity to a sequence set forth as SEQ ID NO: 5. In some embodiments, modified α-GAL polypeptides comprise a polypeptide with a sequence containing cysteine residues at positions 233 and 359 and having at least 96% identity to a sequence set forth as SEQ ID NO: 5. In some embodiments, modified α-GAL polypeptides comprise a polypeptide with a sequence containing cysteine residues at positions 233 and 359 and having at least 97% identity to a sequence set forth as SEQ ID NO: 5. In some embodiments, modified α-GAL polypeptides comprise a polypeptide with a sequence containing cysteine residues at positions 233 and 359 and having at least 98% identity to a sequence set forth as SEQ ID NO: 5. In some embodiments, modified α-GAL polypeptides comprise a polypeptide with a sequence containing cysteine residues at positions 233 and 359 and having at least 99% identity to a sequence set forth as SEQ ID NO: 5. In some embodiments, modified α-GAL polypeptides comprise a polypeptide with a sequence containing cysteine residues at positions 233 and 359 and having more than 99% identity to a sequence set forth as SEQ ID NO: 5. In some embodiments, modified α-GAL polypeptides comprise a polypeptide with a sequence set forth as SEQ ID NO: 5.

Also provided herein are homodimers comprising two modified α-GAL polypeptides, wherein each modified α-GAL polypeptide comprises cysteine substitutions of an α-GAL polypeptide sequence selected from the group consisting of: (i) R49C and G361C; (ii) R49C and G360C; (iii) D233C and I359C; (iv) M51C and G360C; and (v) S276C. In some embodiments, each modified α-GAL polypeptide comprises cysteine substitutions of an α-GAL polypeptide sequence selected from the group consisting of: (i) D233C and I359C; and (ii) M51C and G360C. In some embodiments, each modified α-GAL polypeptide comprises cysteine substitutions of an α-GAL polypeptide sequence of D233C and I359C. In some embodiments, each modified α-GAL polypeptide comprises cysteine substitutions of an α-GAL polypeptide sequence of M51C and G360C. In some embodiments, the homodimer is stabilized by a disulfide bond. In some embodiments, the homodimer shows increased half-life at pH 7.4 compared with a wild type α-GAL homodimer.

In some embodiments, modified α-GAL polypeptides have an increased half-life at pH 4.6. In some embodiments, the half-life at pH 4.6 is at least 50% greater than a wild type α-GAL polypeptide. In some embodiments, the half-life at pH 4.6 is at least 150% greater than a wild type α-GAL polypeptide. In some embodiments, the half-life at pH 4.6 is at least 200% greater than a wild type α-GAL polypeptide. In some embodiments, the half-life at pH 4.6 is at least 250% greater than a wild type α-GAL polypeptide. In some embodiments, the half-life at pH 4.6 is at least 300% greater than a wild type α-GAL polypeptide. In some embodiments, the half-life at pH 4.6 is at least 350% greater than a wild type α-GAL polypeptide. In some embodiments, the half-life at pH 4.6 is at least 400% greater than a wild type α-GAL polypeptide.

In some embodiments, the modified α-GAL dimer has a half-life at pH 4.6 that is increased by at least a factor of about 2, 2.5, 3, 3.5, 4, 4.5 or 5 compared to the half-life of wild type α-GAL at pH 4.6. More preferably, the modified α-GAL dimer has a half-life at pH 4.6 that is increased by at least a factor of about 3, 3.5, or 4 compared to the half-life of wild type α-GAL polypeptide at pH 4.6.

In some embodiments, the modified α-GAL dimer has an intracellular half-life at that is increased by at least a factor of about 2, 2.5, 3, 3.5, 4, 4.5 or 5 compared to the intracellular half-life of wild type human α-GAL. More preferably, the modified α-GAL dimer has an intracellular half-life that is increased by at least a factor of about 3, 3.5, or 4, 4.5 or 5 compared to the intracellular half-life of wild type α-GAL polypeptide.

The modified α-GAL dimer has a substantially increased half-life at pH 7.4 compared to wild type human α-GAL.

Nucleic Acids Encoding Modified α-GAL polypeptides

Also provided herein are nucleic acid molecules comprising nucleic acids encoding a modified α-GAL polypeptide. Contemplated nucleic acids include those encoding a polypeptide comprising cysteine substitutions of an α-GAL polypeptide sequence including: (i) R49C and G361C; (ii) R49C and G360C; (iii) D233C and I359C; (iv) M51C and G360C; and (v) S276C. In some embodiments, the nucleic acid encodes a polypeptide comprising cysteine substitutions of an α-GAL polypeptide sequence selected from the group consisting of: (i) D233C and I359C; and (ii) M51C and G360C. In some embodiments, the nucleic acid encodes a polypeptide comprising cysteine substitutions of D233C and I359C. In some embodiments, the nucleic acid encodes a polypeptide comprising cysteine substitutions of M51C and G360C. In some embodiments, the polypeptide forms a homodimer. In some embodiments, the homodimer is stabilized by a disulfide bond. In some embodiments, the polypeptide shows increased half-life at pH 7.4 compared with a wild type α-GAL polypeptide. In some embodiments, the nucleic acid is a gene therapy construct. In some embodiments, the nucleic acid further comprises a promoter. In some embodiments, the promoter is a constitutive promoter. In some embodiments, the promoter is a tissue-specific promoter. In some embodiments, the nucleic acid comprises at least a portion of a virus nucleic acid sequence. In some embodiments, the virus is selected from wherein the virus comprises a retrovirus, an adenovirus, an adeno associated virus, a lentivirus, or a herpes virus.

Also provided herein are nucleic acid constructs comprising at least one promoter and a nucleic acid encoding a modified α-GAL polypeptide. Modified α-GAL polypeptides are contemplated to comprise cysteine substitutions of an α-GAL polypeptide sequence including: (i) R49C and G361C; (ii) R49C and G360C; (iii) D233C and I359C; (iv) M51C and G360C; and (v) S276C. In some embodiments, the nucleic acid encodes a polypeptide comprising cysteine substitutions of an α-GAL polypeptide sequence selected from the group consisting of: (i) D233C and I359C; and (ii) M51C and G360C. In some embodiments, the nucleic acid encodes a polypeptide comprising cysteine substitutions of an α-GAL polypeptide sequence of D233C and I359C. In some embodiments, the nucleic acid encodes a polypeptide comprising cysteine substitutions of an α-GAL polypeptide sequence of M51C and G360C. In some embodiments, the promoter is a constitutive promoter. In some embodiments, the promoter is a tissue-specific promoter. In some embodiments, the nucleic acid construct comprises at least a portion of a virus nucleic acid sequence. In some embodiments, the virus comprises a retrovirus, an adenovirus, an adeno associated virus, a lentivirus, or a herpes virus. In some embodiments, the polypeptide forms a homodimer. In some embodiments, the homodimer is stabilized by a disulfide bond. In some embodiments, the polypeptide shows increased half-life at pH 7.4 compared with a wild type α-GAL polypeptide. In some embodiments, the nucleic acid is packaged within in a viral capsid protein. In some embodiments, the nucleic acid construct is suitable for gene therapy.

TABLE 2 a-GAL Nucleic Acid Sequences

| α-GAL variant | Sequence | SEQ ID NO: |
|---|---|---|
| α-GAL wild type | atgcagctgaggaacccagaactacatctgggctgcgcgcttgcgcttcgcttcctggccdcgtacctg<br>ggacatccctggggctagagcactggacaatggattggcaaggacgcctaccatgggctggctgcactg<br>ggagcgcttcatgtgcaaccttgactgccaggaagagccagattcctgcatcagtgagaagctcttcatgg<br>agatggcagagctcatggtctcagaaggctggaaggatgcaggttatgagtacctctgcattgatgactgt<br>tggatggctccccaaagagattcagaaggcagacttcaggcagacccctcagcgctacctcatgggattc<br>gccagctagctaattatgttcacagcaaaggactgaagctagggatttatgcagatgttggaaataaaacct<br>gcgcaggcttccctgggagttaggatactacgacattgatgcccagacctagctgactggggagtagat<br>ctgctaaaatttgatggttgttactgtgacagtttggaaaatttggcagatggttataagcacatgtccttggc<br>cctgaataggactggcagaagcattgtgtactcctgtgagtggcctctttatatgtggcccttttcaaaagccc<br>aattatacagaaatccgacagtactgcaatcactggcgaaattttgctgacattgatgattcctggaaaagta<br>taaagagtatcttggactggacatcttttaaccaggagagaattgttgatgttgctggaccaggggggttgga<br>atgacccagatatgttagtgattggcaactttggcctcagctggaatcagcaagtaactcagatggccctct<br>gggctatcatggctgctcctttattcatgtctaatgacctccgacacatcagccctcaagccaaagctctcct<br>tcaggataaggacgtaattgccatcaatcaggacccccttgggcaagcaagggtaccagcttagacaggg<br>agacaactttgaagtgtgggaacgacctctctcaggcttagcctgggctgtagctatgataaaccggcag<br>gagattggtggacctcgctcttataccatcgcagttgcttccctgggtaaaggagtggcctgtaatcctgcc<br>tgcttcatcacacagctcctccctgtgaaaaggaagctagggttctatgaatggacttcaaggttaagaagt<br>cacataaatcccacaggcactgttttgcttcagctagaaaatacaatgcagatgtcattaaaagacttactta<br>a | 7 |
| α-GAL R49C-G361C | atgcagctgaggaacccagaactacatctgggctgcgcgcttgcgcttcgcttcctggccdcgtacctg<br>ggacatccctggggctagagcactggacaatggattggcaaggacgcctaccatgggctggctgcactg<br>ggagTgcttcatgtgcaaccttgactgccaggaagagccagattcctgcatcagtgagaagctcttcatg<br>gagatggcagagctcatggtctcagaaggctggaaggatgcaggttatgagtacctctgcattgatgact | 8 |

TABLE 2-continued a-GAL Nucleic Acid Sequences

| α-GAL variant | Sequence | SEQ ID NO: |
|---|---|---|
| | gttggatggctccccaaagagattcagaaggcagacttcaggcagaccctcagcgctacctcatgggatt cgccagctagctaattatgttcacagcaaaggactgaagctagggatttatgcagatgttggaaataaaac ctgcgcaggcttccctgggagttaggatactacgacattgatgcccagacctagctgactggggagtag atctgctaaaatttgatggttgttactgtgacagtttggaaaatttggcagatggttataagcacatgtccttgg ccctgaataggactggcagaagcattgtgtactcctgtgagtggcctctttatatgtggccctttcaaaagcc caattatacagaaatccgacagtactgcaatcactggcgaaattttgctgacattgatgattcctggaaaagt ataaagagtatcttggactggacatctttttaaccaggagagaattgttgatgttgctggaccaggggggttgg aatgacccagatatgttagtgattggcaactttggcctcagctggaatcagcaagtaactcagatggccctc tgggctatcatggctgctcctttattcatgtctaatgacctccgacacatcagccctcaagccaaagctctcc ttcaggataaggacgtaattgccatcaatcaggaccccttgggcaagcaagggtaccagcttagacagg gagacaactttgaagtgtgggaacgacctctctcaggcttagcctgggctgtagctatgataaaccggca ggagattggtTgCcctcgctcttataccatcgcagttgcttccctgggtaaaggagtggcctgtaatcctgc cctgcttcatcacacagctcctccctgtgaaaaggaagctagggttctatgaatggacttcaaggttaagaa gtcacataaatcccacaggcactgttttgcttcagctagaaaatacaatgcagatgtcattaaaagacttactt taa | |
| α-GAL R49C-G360C | atgcagctgaggaacccagaactacatctgggctgcgcgcttgcgcttcgcttcctggccctcgtttcctg ggacatccctggggctagagcactggacaatggattggcaaggacgcctaccatgggctggctgcactg ggagTgcttcatgtgcaaccttgactgccaggaagagccagattcctgcatcagtgagaagctcttcatg gagatggcagagctcatggtctcagaaggctggaaggatgcaggttatgagtacctctgcattgatgact gttggatggctccccaaagagattcagaaggcagacttcaggcagaccctcagcgctttcctcatgggatt cgccagctagctaattatgttcacagcaaaggactgaagctagggatttatgcagatgttggaaataaaac ctgcgcaggcttccctgggagttttggatactacgacattgatgcccagacctttgctgactggggagtag atctgctaaaatttgatggttgttactgtgacagtttggaaaatttggcagatggttataagcacatgtccttgg ccctgaataggactggcagaagcattgtgtactcctgtgagtggcctctttatatgtggccctttcaaaagcc caattatacagaaatccgacagtactgcaatcactggcgaaattttgctgacattgatgattcctggaaaagt ataaagagtatcttggactggacatctttttaaccaggagagaattgttgatgttgctggaccaggggggttgg aatgacccagatatgttagtgattggcaactttggcctcagctggaatcagcaagtaactcagatggccctc tgggctatcatggctgctcctttattcatgtctaatgacctccgacacatcagccctcaagccaaagctctcc ttcaggataaggacgtaattgccatcaatcaggaccccttgggcaagcaagggtaccagcttagacagg gagacaactttgaagtgtgggaacgacctctctcaggcttagcctgggctgtagctatgataaaccggca ggagattTgtggacctcgctcttataccatcgcagttgcttccctgggtaaaggagtggcctgtaatcctgc ctgcttcatcacacagctcctccctgtgaaaaggaagctagggttctatgaatggacttcaaggttaagaag tcacataaatcccacaggcactgttttgcttcagctagaaaatacaatgcagatgtcattaaaagacttacttt aa | 9 |
| α-GAL M51C-G360C | atgcagctgaggaacccagaactacatctgggctgcgcgcttgcgcttcgcttcctggccctcgtttcctg ggacatccctggggctagagcactggacaatggattggcaaggacgcctaccatgggctggctgcactg ggagcgcttcTGCtgcaaccttgactgccaggaagagccagattcctgcatcagtgagaagctcttcat ggagatggcagagctcatggtctcagaaggctggaaggatgcaggttatgagtacctctgcattgatgac tgttggatggctccccaaagagattcagaaggcagacttcaggcagaccctcagcgctttcctcatgggat tcgccagctagctaattatgttcacagcaaaggactgaagctagggatttatgcagatgttggaaataaaac ctgcgcaggcttccctgggagttttggatactacgacattgatgcccagacctttgctgactggggagtag atctgctaaaatttgatggttgttactgtgacagtttggaaaatttggcagatggttataagcacatgtccttgg ccctgaataggactggcagaagcattgtgtactcctgtgagtggcctctttatatgtggccctttcaaaagcc caattatacagaaatccgacagtactgcaatcactggcgaaattttgctgacattgatgattcctggaaaagt ataaagagtatcttggactggacatctttttaaccaggagagaattgttgatgttgctggaccaggggggttgg aatgacccagatatgttagtgattggcaactttggcctcagctggaatcagcaagtaactcagatggccctc tgggctatcatggctgctcctttattcatgtctaatgacctccgacacatcagccctcaagccaaagctctcc ttcaggataaggacgtaattgccatcaatcaggaccccttgggcaagcaagggtaccagcttagacagg gagacaactttgaagtgtgggaacgacctctctcaggcttagcctgggctgtagctatgataaaccggca ggagattTgtggacctcgctcttataccatcgcagttgcttccctgggtaaaggagtggcctgtaatcctgc ctgcttcatcacacagctcctccctgtgaaaaggaagctagggttctatgaatggacttcaaggttaagaag tcacataaatcccacaggcactgttttgcttcagctagaaaatacaatgcagatgtcattaaaagacttacttt aa | 10 |
| α-GAL D233C-I359C | atgcagctgaggaacccagaactacatctgggctgcgcgcttgcgcttcgcttcctggccctcgtacctg ggacatccctggggctagagcactggacaatggattggcaaggacgcctaccatgggctggctgcactg ggagcgcttcatgtgcaaccttgactgccaggaagagccagattcctgcatcagtgagaagctcttcatgg agatggcagagctcatggtctcagaaggctggaaggatgcaggttatgagtacctctgcattgatgactgt tggatggctccccaaagagattcagaaggcagacttcaggcagaccctcagcgctacctcatgggattc gccagctagctaattatgttcacagcaaaggactgaagctagggatttatgcagatgttggaaataaaacct gcgcaggcttccctgggagttaggatactacgacattgatgcccagacctagctgactggggagtagat ctgctaaaatttgatggttgttactgtgacagtaggaaaataggcagatggttataagcacatgtccttggc cctgaataggactggcagaagcattgtgtactcctgtgagtggcctctttatatgtggccctacaaaagccc aattatacagaaatccgacagtactgcaatcactggcgaaattttgctgacattTGCgattcctggaaaa gtataaagagtatcttggactggacatctttttaaccaggagagaattgttgatgttgctggaccagggggtt ggaatgacccagatatgttagtgattggcaactaggcctcagctggaatcagcaagtaactcagatggcc ctctgggctatcatggctgctcctttattcatgtctaatgacctccgacacatcagccctcaagccaaagctc tccttcaggataaggacgtaattgccatcaatcaggaccccttgggcaagcaagggtaccagcttagaca gggagacaactttgaagtgtgggaacgacctctctcaggcttagcctgggctgtagctatgataaaccgg caggagTGCggtggacctcgctcttataccatcgcagttgcttccctgggtaaaggagtggcctgtaat cctgccttgcttcatcacacagctcctccctgtgaaaaggaagctagggttctatgaatggacttcaaggtta agaagtcacataaatcccacaggcactgttagcttcagctagaaaatacaatgcagatgtcattaaaagac ttactttaa | 11 |

TABLE 2-continued a-GAL Nucleic Acid Sequences

| α-GAL variant | Sequence | SEQ ID NO: |
|---|---|---|
| α-GAL S276C | atgcagctgaggaacccagaactacatctgggctgcgcgcttgcgcttcgcttcctggccctcgtacctg<br>ggacatccctggggctagagcactggacaatggattggcaaggacgcctaccatgggctggctgcactg<br>ggagcgcttcatgtgcaaccttgactgccaggagagccagattcctgcatcagtgagaagctcttcatgg<br>agatggcagagctcatggtctcagaaggctggaaggatgcaggttatgagtacctctgcattgatgactgt<br>tggatggctccccaaagagattcagaaggcagacttcaggcagaccctcagcgctacctcatgggattc<br>gccagctagctaattatgttcacagcaaaggactgaagctagggatttatgcagatgttggaaataaaacct<br>gcgcaggcttccctgggagttaggatactacgacattgatgcctagctgactggggagtagat<br>ctgctaaaatttgatggttgttactgtgacagtaggaaaataggcagatggttataagcacatgtccttggc<br>cctgaataggactggcagaagcattgtgtactcctgtgagtggcctctttatatgtggccctttcaaaagccc<br>aattatacagaaatccgacagtactgcaatcactggcgaaattttgctgacattgatgattcctggaaaagta<br>taaagagtatcttggactggacatcttttaaccaggagagaattgttgattgctggaccagggggttgga<br>atgacccagatatgttagtgattggcaactaggcctcTgctggaatcagcaagtaactcagatggccctct<br>gggctatcatggctgctcctttattcatgtctaatgacctccgacacatcagccctcaagccaaagctctcct<br>tcaggataaggacgtaattgccatcaatcaggacccttgggcaagcaagggtaccagcttagacaggg<br>agacaactttgaagtgtggaacgacctctctcaggcttagcctgggctgtagctatgataaaccggcag<br>gagattggtggacctcgctcttataccatcgcagttgcttccctgggtaaaggagtggcctgtaatcctgcc<br>tgcttcatcacacagctcctccctgtgaaaaggaagctagggttctatgaatggacttcaaggttaagaagt<br>cacataaatcccacaggcactgttagcttcagctagaaaatacaatgcagatgtcattaaaagacttacttta<br>a | 12 |

In some embodiments, nucleic acids encoding modified α-GAL polypeptides herein have an increased half-life compared with a wild type α-GAL polypeptide. In some embodiments, the half-life is at least 50% greater than a wild type α-GAL polypeptide. In some embodiments, the half-life is at least 150% greater than a wild type α-GAL polypeptide. In some embodiments, the half-life is at least 200% greater than a wild type α-GAL polypeptide. In some embodiments, the half-life is at least 250% greater than a wild type α-GAL polypeptide. In some embodiments, the half-life is at least 300% greater than a wild type α-GAL polypeptide. In some embodiments, the half-life is at least 350% greater than a wild type α-GAL polypeptide.

Modified PPT-1 Polypeptides

Provided herein are modified PPT-1 polypeptides comprising cysteine substitutions of a PPT-1 polypeptide sequence. Contemplated substitutions provided herein include A171C and A183C. In some embodiments, the polypeptide comprises cysteine substitutions of a PPT-1 polypeptide sequence of A171C and A183C. The modified PPT-1 polypeptide is stabilized by at least one, more preferably two intramolecular disulfide bonds. The modified PPT-1 polypeptides polypeptide show increased half-life at pH 7.4 compared with a wildtype PPT-1 polypeptide.

Wild type and exemplary Modified PPT-1 are provided in Table 3.

TABLE 3

PPT-1 Polypeptide Sequences

| PPT-1 variant | Sequence | SEQ ID NO: |
|---|---|---|
| Human PPT-1 wild type (NP_000301.1) | MASPGCLWLLAVALLPWTCASRALQHLDPPAPLPLVIWHGMGDSCCNPLSMGAI<br>KKMVEKKIPGIYVLSLEIGKTLMEDVENSFFLNVNSQVTTVCQALAKDPKLQQGY<br>NAMGFSQGGQFLRAVAQRCPSPPMINLISVGGQHQGVFGLPRCPGESSHICDFIRK<br>TLNAGAYSKVVQERLVQAEYWHDPIKEDVYRNHSIFLADINQERGINESYKKNL<br>MALKKFVMVKFLNDSIVDPVDSEWFGFYRSGQAKETIPLQETSLYTQDRLGLKE<br>MDNAGQLVFLATEGDHLQLSEEWFYAHIIPFLG | 13 |
| PPT-1 A171C A183C | MASPGCLWLLAVALLPWTCASRALQHLDPPAPLPLVIWHGMGDSCCNPLSMGAI<br>KKMVEKKIPGIYVLSLEIGKTLMEDVENSFFLNVNSQVTTVCQALAKDPKLQQGY<br>NAMGFSQGGQFLRAVAQRCPSPPMINLISVGGQHQGVFGLPRCPGESSHICDFIRK<br>TLNAGCYSKVVQERLVQCEYWHDPIKEDVYRNHSIFLADINQERGINESYKKNL<br>MALKKFVMVKFLNDSIVDPVDSEWFGFYRSGQAKETIPLQETSLYTQDRLGLKE<br>MDNAGQLVFLATEGDHLQLSEEWFYAHIIPFLG | 14 |

Also provided herein are modified PPT-1 polypeptides comprising a polypeptide with a sequence containing cysteine residues at positions 171 and 183 and having at least 90% identity to a sequence set forth as SEQ ID NO: 14. In some embodiments, modified PPT-1 polypeptides comprise a polypeptide with a sequence containing cysteine residues at positions 171 and 183 and having at least 95% identity to a sequence set forth as SEQ ID NO: 14. In some embodiments, modified PPT-1 polypeptides comprise a polypeptide with a sequence containing cysteine residues at positions 171 and 183 and having at least 96% identity to a sequence set forth as SEQ ID NO: 14. In some embodiments, modified PPT-1 polypeptides comprise a polypeptide with a sequence containing cysteine residues at positions 171 and 183 and having at least 97% identity to a sequence set forth as SEQ ID NO: 14. In some embodiments, modified PPT-1 polypeptides comprise a polypeptide with a sequence containing cysteine residues at positions 171 and 183 and having at least 98% identity to a sequence set forth as SEQ ID NO: 14. In some embodiments, modified PPT-1 polypeptides comprise a polypeptide with a sequence containing cysteine residues at positions 171 and 183 and having at least 99% identity to a sequence set forth as SEQ ID NO: 14. In some embodiments, modified PPT-1 polypeptides comprise a polypeptide with a sequence containing cysteine residues at positions 171 and 183 and having more than 99% identity to a sequence set forth as SEQ ID NO: 14. In some embodiments, modified PPT-1 polypeptides comprise a polypeptide with a sequence set forth as SEQ ID NO: 14.

In some embodiments, modified PPT-1 polypeptides have an increased half-life at pH 4.6. In some embodiments, the half-life at pH 4.6 is at least 50% greater than a wild type PPT-1 polypeptide. In some embodiments, the half-life at pH 4.6 is at least 150% greater than a wild type PPT-1 polypeptide. In some embodiments, the half-life at pH 4.6 is at least 200% greater than a wild type PPT-1 polypeptide. In some embodiments, the half-life at pH 4.6 is at least 250% greater than a wild type PPT-1 polypeptide. In some embodiments, the half-life at pH 4.6 is at least 300% greater than a wild type PPT-1 polypeptide. In some embodiments, the half-life at pH 4.6 is at least 350% greater than a wild type PPT-1 polypeptide. In some embodiments, the half-life at pH 4.6 is at least 400% greater than a wild type PPT-1 polypeptide.

In some embodiments, the modified PPT-1 polypeptide has a half-life at pH 4.6 that is increased by at least a factor of about 2, 2.5, 3, 3.5, 4, 4.5 or 5 compared to the half-life of wild type PPT-1 at pH 4.6. More preferably, the modified PPT-1 polypeptide has a half-life at pH 4.6 that is increased by at least a factor of about 3, 3.5, or 4 compared to the half-life of wild type PPT-1 polypeptide at pH 4.6.

In some embodiments, the modified PPT-1 polypeptide has an intracellular half-life at that is increased by at least a factor of about 2, 2.5, 3, 3.5, 4, 4.5 or 5 compared to the intracellular half-life of wild type human α-GAL. More preferably, the modified PPT-1 polypeptide has an intracellular half-life that is increased by at least a factor of about 3, 3.5, or 4, 4.5 or 5 compared to the intracellular half-life of wild type PPT-1 polypeptide.

The modified PPT-1 polypeptide has a substantially increased half-life at pH 7.4 compared to wild type human α-GAL.

Nucleic Acids Encoding Modified PPT-1 Polypeptides

Also provided herein are nucleic acid molecules comprising nucleic acids encoding a modified PPT-1 polypeptide. Contemplated nucleic acids include those encoding a polypeptide comprising cysteine substitutions of a PPT-1 polypeptide sequence including: A171C and A183C. In some embodiments, the nucleic acid encodes a polypeptide comprising cysteine substitutions of A171C and A183C. In some embodiments, the polypeptide is stabilized by a disulfide bond. In some embodiments, the polypeptide shows increased half-life at pH 7.4 compared with a wild type PPT-1 polypeptide. In some embodiments, the nucleic acid is a gene therapy construct. In some embodiments, the nucleic acid further comprises a promoter. In some embodiments, the promoter is a constitutive promoter. In some embodiments, the promoter is a tissue-specific promoter. In some embodiments, the nucleic acid comprises at least a portion of a virus nucleic acid sequence. In some embodiments, the virus is selected from wherein the virus comprises a retrovirus, an adenovirus, an adeno associated virus, a lentivirus, or a herpes virus.

TABLE 4

PPT-1 Nucleic Acid Sequences

| PPT-1 variant | Sequence | SEQ ID NO: |
|---|---|---|
| PPT-1 wild type | TTATTTTGATTCACCGCAGAGGGCGGTCTACGAGAGCGCAGAG<br>CCCCACTCGGCCAGCGGGGTCTGGCGGGGGACCTGTCGCGCTG<br>AAAGCTCCAGGGTAGGGCCGACGCCCATCAGGCTGGGCATCCG<br>TTCGGGATGCGCAGGTTGCGATCTGCAACCGGCGGCGCCACGC<br>CCAGGCGGGCGGAGCGCGGTTCCCGGAGTCTCGCGCCCGCGGT<br>CATGTGACACAGCGAAGATGGCGTCGCCCGGCTGCCTGTGGCT<br>CTTGGCTGTGGCTCTCCTGCCATGGACCTGCGCTTCTCGGGCGC<br>TGCAGCATCTGGACCCGCCGGCGCCGCTGCCGTTGGTGATCTGG<br>CATGGGATGGGAGACAGCTGTTGCAATCCCTTAAGCATGGGTG<br>CTATTAAAAAAATGGTGGAGAAGAAAATACCTGGAATTTACGT<br>CTTATCTTTAGAGATTGGGAAGACCCTGATGGAGGACGTGGAG<br>AACAGCTTCTTCTTGAATGTCAATTCCCAAGTAACAACAGTGTG<br>TCAGGCACTTGCTAAGGATCCTAAATTGCAGCAAGGCTACAAT<br>GCTATGGGATTCTCCCAGGGAGGCCAATTTCTGAGGGCAGTGG<br>CTCAGAGATGCCCTTCACCTCCCATGATCAATCTGATCTCGGTT<br>GGGGGACAACATCAAGGTGTTTTTGGACTCCCTCGATGCCCAG<br>GAGAGAGCTCTCACATCTGTGACTTCATCCGAAAAACACTGAA<br>TGCTGGGCGTACTCCAAAGTTGTTCAGGAACGCCTCGTGCAA<br>GCCGAATACTGGCATGACCCCATAAAGGAGGATGTGTATCGCA<br>ACCACAGCATCTTCTTGGCAGATATAAATCAGGAGCGGGGTAT<br>CAATGAGTCCTACAAGAAAAACCTGATGGCCCTGAAGAAGTTT<br>GTGATGGTGAAATTCCTCAATGATTCCATTGTGGACCCTGTAGA<br>TTCGGAGTGGTTTGGATTTTACAGAAGTGGCCAAGCCAAGGAA<br>ACCATTCCCTTACAGGAGACCTCCCTGTACACACAGGACCGCCT<br>GGGGCTAAAGGAAATGGACAATGCAGGACAGCTAGTGTTTCTG<br>GCTACAGAAGGGGACCATCTTCAGTTGTCTGAAGAATGGTTTTA<br>TGCCCACATCATACCATTCCTTGGATGAAACCCGTATAGTTCAC<br>AATAGAGCTCAGGGAGCCCCTAACTCTTCCAAACCACATGGGA<br>GACAGTTTCCTTCATGCCCAAGCCTGAGCTCAGATCCAGCTTGC<br>AACTAATCCTTCTATCATCTAACATGCCCTACTTGGAAAGATCT<br>AAGATCTGAATCTTATCCTTTGCCATCTTCTGTTACCATATGGTG<br>TTGAATGCAAGTTTAATTACCATGGAGATTGTTTTACAAACTTT<br>TGATGTGGTCAAGTTCAGTTTTAGAAAAGGGAGTCTGTTCCAGA | 15 |

TABLE 4-continued

PPT-1 Nucleic Acid Sequences

| PPT-1 variant | Sequence | SEQ ID NO: |
|---|---|---|
| | TCAGTGCCAGAACTGTGCCCAGGCCCAAAGGAGACAACTAACT<br>AAAGTAGTGAGATAGATTCTAAGGGCAAACATTTTTCCAAGTCT<br>TGCCATATTTCAAGCAAAGAGGTGCCCAGGCCTGAGGTACTCA<br>CATAAATGCTTTGTTTTGCTGGTGATTTAACCAGTGCTTGGAAA<br>AATCTTGCTTGGCTATTTCTGCATCATTTCTTAAGGCTGCCTTCC<br>TCTCTCAGTACGTTGCCCTCTGTGCTATCATCTTATCATCAATTA<br>TTAGACAAATCCCACTGGCCTACAGTCTTGCTTCTGCAGCACCC<br>ACTTTGTCTCCTCAGGTAGTGATGAATTAGTTGCTGTCACAAAA<br>GGAGGGAAGTAGCACCCAAATTAAGTTGCTTAAGAGAGGAAAT<br>GTACATCTTGTATAACTTAGGGAGCGAAGAAAATGTAGGCGCG<br>AAAGTGAAAAGTGAGGCAGCTAGTTCTTCCTATTCCATTCTCGA<br>CCAACCTGCCCTTTCTTAATATGACTAGTGGTCTTGATGCTAGA<br>GTCAACTTACTCTGTTGCTGGCTTTAGCAGAGAATAGGAGGAAC<br>CATATGAAAAAGATCAGGCTTTCTGACTTCCATCCCCAAAACAC<br>ATTTACCAGCATACTCCAAACTGTTTCTGATGTGTTCCATGAGA<br>AAAGGATTGTTTGCTCAAAAAGCTTGGAAAATACTACACACTC<br>CCTTTCTCCTTCTGGAGATCAACCCACATTAGAGTGTCTAAGGA<br>CTCCTGAGAATTCCTGTTACAGTAAACAAAACTAACGTAATCTA<br>CCATTTCCTACACTATTTGAGCATGGAAATCATAGTCCCCACTC<br>TGTGAAAACTTAACGCTTTTTGGAAGACATTTCTGTAGCATGTC<br>AGTTTGGAGAAATGATGAGCTACGCCTTGATGAAAGAACCGTG<br>TTGGTGCTGCTAAGTTTAGCCATTATGGTTTTTCCTTTCTCTCTC<br>TTAAGCCTTATTCTTCAACTAAAAGATGAGGATTAAGAGCAAG<br>AAGTTGGGGGGATGTGAAAATAATTTTATGAGGTTGTCTAAA<br>ATAAAGAGTAGTTTCTTATC | |
| PPT-1<br>A171C<br>A183C | ATGGCATCACCGGGTTGCCTCTGGTTGTTGGCCGTTGCGTTGCT<br>TCCGTGGACATGTGCATCAAGAGCTCTTCAACATCTGGATCCCC<br>CAGCTCCCCTGCCGCTCGTAATCTGGCACGGGATGGGGGATTC<br>ATGTTGTAACCCGTTGTCAATGGGCGCGATAAAAAAGATGGTT<br>GAAAAGAAGATTCCAGGCATCTACGTTCTGTCCCTGGAAATCG<br>GTAAGACACTGATGGAAGACGTGGAGAACTCCTTCTTTCTCAAC<br>GTCAATAGTCAGGTCACTACCGTCTGTCAAGCATTGGCAAAGG<br>ACCCTAAACTTCAGCAGGGGTACAATGCGATGGGGTTTAGCCA<br>GGGCGGACAGTTTCTTAGAGCCGTCGCACAGCGCTGTCCATCTC<br>CCCCGATGATTAACCTTATATCTGTCGGGGGACAACACCAGGGT<br>GTTTTTGGTCTTCCTCGCTGTCCTGGTGAAAGCTCCCACATCTGT<br>GATTTCATACGCAAAACGTTGAACGCAGGATGCTATAGTAAAG<br>TCGTCCAAGAACGGCTTGTTCAATGCGAGTATTGGCATGACCCA<br>ATAAAAGAAGACGTTTATAGGAATCACTCTATCTTCTTGGCCGA<br>TATCAACCAAGAACGCGGAATCAACGAAAGCTACAAAAAGAAT<br>CTTATGGCTCTCAAGAAATTTGTTATGGTGAAATTCCTTAATGA<br>CTCTATAGTAGATCCTGTCGATTCAGAATGGTTCGGGTTCTACA<br>GGTCTGGCCAGGCGAAGGAGACTATTCCCCTCCAAGAAACGTC<br>TCTCTATACACAAGACAGACTCGGACTGAAAGAGATGGATAAT<br>GCGGGCCAGTTGGTCTTCTTGGCTACGGAAGGCGATCATCTCCA<br>ACTCTCCGAAGAGTGGTTCTATGCCCATATAATCCCGTTCCTGG<br>GCTAA | 16 |

In some embodiments, nucleic acids encoding modified PPT-1 polypeptides herein have an increased half-life compared with a wild type PPT-1 polypeptide. In some embodiments, the half-life is at least 50% greater than a wild type PPT-1 polypeptide. In some embodiments, the half-life is at least 150% greater than a wild type PPT-1 polypeptide. In some embodiments, the half-life is at least 200% greater than a wild type PPT-1 polypeptide. In some embodiments, the half-life is at least 250% greater than a wild type PPT-1 polypeptide. In some embodiments, the half-life is at least 300% greater than a wild type PPT-1 polypeptide. In some embodiments, the half-life is at least 350% greater than a wild type PPT-1 polypeptide.

IGF2 Peptides

In some cases, modified polypeptides herein, such as modified α-GAL or modified PPT-1 polypeptides herein are fused to an Insulin-Like Growth Factor 2 (IGF2) peptide for targeting modified polypeptides to the lysosome where they are needed. Variants in the IGF2 peptide sequence maintain high affinity binding to IGF2/CI-MPR and eliminate binding to IGF1, insulin receptors, and IGF binding proteins (IGFBP). The variant IGF2 peptide is substantially more selective and has reduced safety risks compared to conventional IGF2 fusion proteins. IGF2 peptides herein include those having an amino acid sequence of AYRPSETLCGGELVDTLQFVCGDRGFYFSRPASRVSRRSR-GIVEECCFRSCDLALLETYCATPAKSE (SEQ ID NO: 17). Additional IGF2 peptides have variant amino acid sequences optimized for improved targeting. Variant IGF2 peptides include variant amino acids at positions, 26, 27, 43, 48, 49, 50, 54, 55, or 65 of a wild type IGF2 sequence. These include substitutions at F26, Y27, V43, F48, R49, S50, A54, L55, or K65 of SEQ ID NO: 17. In some embodiments, the IGF2 peptide has a sequence having one or more substitutions from the group consisting of F26S, Y27L, V43L, F48T, R49S, S50I, A54R, L55R, and K65R. In some embodiments, the IGF2 peptide has a sequence having a substitution of F26S. In some embodiments, the IGF2 peptide has a sequence having a substitution of Y27L. In some embodiments, the IGF2 peptide has a sequence having a substitution of V43L. In some embodiments, the IGF2 peptide has a sequence having a substitution of F48T. In some embodiments, the IGF2 peptide has a sequence having a substitution of R49S. In some embodiments, the IGF2 peptide has a sequence having a substitution of S50I. In some embodiments, the IGF2 peptide has a sequence having a substitution of A54R. In some embodiments, the IGF2 peptide has a sequence having a substitution of L55R. In some embodiments, the IGF2 peptide has a sequence having a substitution of K65R. In some embodiments, the IGF2 peptide has a sequence having a substitution of F26S, Y27L, V43L, F48T, R49S, S50I, A54R, and L55R. In some embodiments, the IGF2 peptide has an N-terminal deletion. In some embodiments, the IGF2 peptide has an N-terminal deletion of one amino acid. In some embodiments, the IGF2 peptide has an N-terminal deletion of two amino acids. In some embodiments, the IGF2 peptide has a sequence having a substitution of L17N. In some embodiments, the IGF2 peptide has a sequence having a substitution of P31G. In some embodiments, the IGF2 peptide has a sequence having a substitution of R38G. In some embodiments, the IGF2 peptide has a sequence having a substitution of E45W. In some embodiments, the IGF2 peptide has a sequence having a substitution of S50G. In some embodiments, the IGF2 peptide has a sequence having substitutions of R38G and E45W. In some embodiments, the IGF2 peptide has a sequence having substitutions of R38G, E45W, and S50G. In some embodiments, the IGF2 peptide has a sequence having substitutions of P31G, R38G, E45W, and S50G. In some embodiments, the IGF2 peptide has a sequence having substitutions of L17N, P31G, R38G, E45W, and S50G. Exemplary peptide sequences are represented by SEQ ID NOs: 17-27.

TABLE 5

IGF Peptide Sequences (variant residues are underlined)

| Peptide | Sequence | SEQ ID NO |
|---|---|---|
| Wild type | AYRPSETLCGGELVDTLQFVCGDRGFYFSRPASR VSRRSRGIVEECCFRSCDLALLETYCATPAKSE | 17 |
| F26S | AYRPSETLCGGELVDTLQFVCGDRGSYFSRPASR VSRRSRGIVEECCFRSCDLALLETYCATPAKSE | 18 |
| Y27L | AYRPSETLCGGELVDTLQFVCGDRGFLFSRPASRV SRRSRGIVEECCFRSCDLALLETYCATPAKSE | 19 |
| V43L | AYRPSETLCGGELVDTLQFVCGDRGFYFSRPASR VSRRSRGILEECCFRSCDLALLETYCATPAKSE | 20 |
| F48T | AYRPSETLCGGELVDTLQFVCGDRGFYFSRPASR VSRRSRGIVEECCTRSCDLALLETYCATPAKSE | 21 |
| R49S | AYRPSETLCGGELVDTLQFVCGDRGFYFSRPASR VSRRSRGIVEECCFSSCDLALLETYCATPAKSE | 22 |
| S50I | AYRPSETLCGGELVDTLQFVCGDRGFYFSRPASR VSRRSRGIVEECCFRICDLALLETYCATPAKSE | 23 |
| A54R | AYRPSETLCGGELVDTLQFVCGDRGFYFSRPASR VSRRSRGIVEECCFRSCDLRLLETYCATPAKSE | 24 |
| L55R | AYRPSETLCGGELVDTLQFVCGDRGFYFSRPASR VSRRSRGIVEECCFRSCDLARLETYCATPAKSE | 25 |
| F26S, Y27L, V43L, F48T, R49S, S50I, A54R, L55R | AYRPSETLCGGELVDTLQFVCGDRGSLFSRPASRV SRRSRGILEECCTSICDLRRLETYCATPAKSE | 26 |
| Δ1-6, Y27L, K65R | TLCGGELVDTLQFVCGDRGFLFSRPASRVSRRSRG IVEECCFRSCDLALLETYCATPARSE | 27 | ments, the IGF2 peptide has an N-terminal deletion of three amino acids. In some embodiments, the IGF2 peptide has an N-terminal deletion of three amino acids. In some embodiments, the IGF2 peptide has an N-terminal deletion of four amino acids. In some embodiments, the IGF2 peptide has an N-terminal deletion of five amino acids. In some embodiments, the IGF2 peptide has an N-terminal deletion of six amino acids. In some embodiments, the IGF2 peptide has an N-terminal deletion of seven amino acids. In some embodiments, the IGF2 peptide has an N-terminal deletion of seven amino acids and a substitution of Y27L and K65R.

Additional substitutions are contemplated for decreasing instability while maintaining CI-MPR binding affinity. These substitutions are contemplated to be combined with any other substitution described herein. In some embodi- Internal Ribosomal Entry Sequences Nucleic acids encoding a modified polypeptides herein, such as nucleic acids encoding modified α-GAL and PP-1 polypeptides, in some embodiments, further comprise an internal ribosome entry sequence (IRES) for increasing gene expression by bypassing the bottleneck of translation initiation. Suitable internal ribosomeal entry sequences for optimizing expression for gene therapy include but are not limited to a cricket paralysis virus (CrPV) IRES, a picornavirus IRES, an Aphthovirus IRES, a Kaposi's sarcoma-associated herpesvirus IRES, a Hepatitis A IRES, a Hepatitis C IRES, a Pestivirus IRES, a Cripavirus IRES, a *Rhopalosiphum padi* virus IRES, a Merek's disease virus IRES, and other suitable IRES sequences. In some embodiments, the gene therapy construct comprises a CrPV IRES. In some embodiments, the CrPV IRES has a nucleic acid sequence of (SEQ ID NO: 28)
CGGUGUCGAAGUAGAAUUUCUAUCUCGACACGCGGCCUUCCAAGCAGU

UAGGGAAACCGACUUCUUUGAAGAAGAAAGCUGACUAUGUGAUCUUAU

UAAAAUUAGGUUAAAUUUCGAGGUUAAAAAUAGUUUUAAUAUUGCUAU

AGUCUUAGAGGUCUUGUAUAUUUAUACUUACCACACAAGAUGGACCGG

AGCAGCCCUCCAAUAUCUAGUGUACCCUCGUGCUCGCUCAAACAUUAA

GUGGUGUUGUGCGAAAAGAAUCUCACUUCAAGAA

Signal Sequence

Provided herein are nucleic acid molecules comprising nucleic acids encoding modified polypeptides, such as modified α-GAL polypeptides or modified PPT-1 polypeptides, wherein the nucleic acid molecules further comprise a signal peptide, which improves secretion of the therapeutic protein from the cell transduced with the gene therapy construct. The signal peptide in some embodiments improves protein processing of therapeutic proteins, and facilitates translocation of the nascent polypeptide-ribosome complex to the ER and ensuring proper co-translational and post-translational modifications. In some embodiments, the signal peptide is located (i) in an upstream position of the signal translation initiation sequence, (ii) in between the translation initiation sequence and the therapeutic protein, or (iii) a downstream position of the therapeutic protein. Signal peptides useful in gene therapy constructs include but are not limited to binding immunoglobulin protein (BiP) signal peptide from the family of HSP70 proteins (e.g., HSPA5, heat shock protein family A member 5), and variants thereof These signal peptides have ultrahigh affinity to the signal recognition particle. Examples of BiP amino acid sequences are provided in Table 6 below. In some embodiments, the signal peptide has an amino acid sequence that is at least 90% identical to a sequence selected from the group consisting of SEQ ID Nos: 29-33. In some embodiments, the signal peptide differs from a sequence selected from the group consisting of SEQ ID Nos: 29-33 by 5 or fewer, 4 or fewer, 3 or fewer, 2 or fewer, or 1 amino acid.

TABLE 6

Signal Sequences

| Signal Sequence | Amino Acid Sequence | SEQ ID NO: |
|---|---|---|
| Native human Bip | MKLSLVAAMLLLLSAARA | 29 |
| Modified Bip-1 | MKLSLVAAMLLLLSLVAAMLLLLSAARA | 30 |
| Modified Bip-2 | MKLSLVAAMLLLLWVALLLLSAARA | 31 |
| Modified Bip-3 | MKLSLVAAMLLLLSLVALLLLSAARA | 32 |
| Modified Bip-4 | MKLSLVAAMLLLLALVALLLLSAARA | 33 |

Kozak Sequence

Provided herein are nucleic acid molecules comprising nucleic acids encoding modified polypeptides, such as modified α-GAL polypeptides or modified PPT-1 polypeptides, wherein the nucleic acid molecules further comprise a nucleic acid having a kozak sequence, which aids in initiation of translation of the mRNA. Kozak sequences contemplated herein have a consensus sequence of gccRccAUGG (SEQ ID NO: 34) where a lowercase letter denotes the most common base at the position and the base varies, uppercase letters indicate highly conserved bases that only vary rarely change. R indicates that a purine (adenine or guanine) is always observed at that position. The sequence in parentheses (gcc) is of uncertain significance.

Therapeutic Protein

Gene therapy constructs provided herein comprise a nucleic acid encoding a stabilized form of a protein for treating a genetic disorder. The therapeutic protein expressed from the gene therapy construct replaces the absent or defective protein. Therapeutic proteins, therefore, are chosen based on the genetic defect in need of treatment in an individual. Stabilized forms herein comprise one or more non-native cysteine residues that form a disulfide bridge between the non-native cysteines within the protein or between non-native cysteines of two monomers of the protein.

In some embodiments, gene therapy constructs herein encode an enzyme, such as an enzyme having a genetic defect in an individual with a lysosomal storage disorder. In some embodiments, enzymes encoded by gene therapy constructs provided herein include but are not limited to alpha-galactosidase A, β-glucocerebrosidase, glucocerebrosidase, lysosomal acid lipase, glycosaminoglycan alpha-L-iduronidase, alpha-L-iduronidase, N-sulfoglucosamine sulfohydrolase (SGSH), N-acetyl-alpha-glucosaminidase (NAGLU), iduronate-2-sulfatase, N-acetylgalactosamine-6-sulfatase, glycosaminoglycan N-acetylgalactosamine 4-sulfatase, alpha-glucosidase, tripeptidyl peptidase 1 (TPP1), palmitoyl protein thioesterases, ceroid lipofuscinoses neuronal 1, ceroid lipofuscinoses neuronal 2, ceroid lipofuscinoses neuronal 3, ceroid lipofuscinoses neuronal 4, ceroid lipofuscinoses neuronal 5, ceroid lipofuscinoses neuronal 6, ceroid lipofuscinoses neuronal 7, ceroid lipofuscinoses neuronal 8, ceroid lipofuscinoses neuronal 9, ceroid lipofuscinoses neuronal 10, ceroid lipofuscinoses neuronal 11, ceroid lipofuscinoses neuronal 12, ceroid lipofuscinoses neuronal 13, ceroid lipofuscinoses neuronal 14, ceroid lipofuscinoses neuronal 15, ceroid lipofuscinoses neuronal 16, and cyclin dependent kinase like 5.

Gene Therapy Vectors and Compositions

Provided herein are gene therapy vectors comprising a nucleic acid construct comprising: a nucleic acid encoding a stabilized form of a protein for treating a neurological or genetic disorder, the stabilized form comprising one or more non-native cysteine residues that form a disulfide bridge between non-native cysteines within the protein or between non-native cysteines of two monomers of the protein. In some embodiments, the stabilized form comprises a modified α-GAL polypeptide or a modified PPT-1 polypeptide.

In some embodiments, the nucleic acid encoding a modified polypeptide is cloned into a number of types of vectors. For example, in some embodiments, the nucleic acid is cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector encoding the modified polypeptide is provided to a cell in the form of a viral vector. Viral vector technology is described, e.g., in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

Also provided herein are compositions and systems for gene transfer. A number of virally based systems have been developed for gene transfer into mammalian cells. For example, retroviruses provide a convenient platform for gene delivery systems. A selected gene, in some embodiments, is inserted into a vector and packaged in retroviral particles using suitable techniques. The recombinant virus is then isolated and delivered to cells of the subject either in vivo or ex vivo. A number of retroviral systems are suitable for gene therapy. In some embodiments, adenovirus vectors are used. A number of adenovirus vectors are suitable for gene therapy. In some embodiments, adeno-associated virus vectors are used. A number of adeno-associated viruses are suitable for gene therapy. In one embodiment, lentivirus vectors are used.

Gene therapy constructs provided herein comprise a vector (or gene therapy expression vector) into which the gene of interest is cloned or otherwise which includes the gene of interest in a manner such that the nucleotide sequences of the vector allow for the expression (constitutive or otherwise regulated in some manner) of the gene of interest. The vector constructs provided herein include any suitable gene expression vector that is capable of being delivered to a tissue of interest and which will provide for the expression of the gene of interest in the selected tissue of interest.

In some embodiments, the vector is an adeno-associated virus (AAV) vector because of the capacity of AAV vectors to cross the blood-brain barrier and transduction of neuronal tissue. In methods provided herein, AAV of any serotype is contemplated to be used. The serotype of the viral vector used in certain embodiments is selected from the group consisting of AAV1 vector, an AAV2 vector, an AAV3 vector, an AAV4 vector, an AAV5 vector, an AAV6 vector, an AAV7 vector, an AAV8 vector, an AAV9 vector, an AAVrhS vector, an AAVrh10 vector, an AAVrh33 vector, an AAVrh34 vector, an AAVrh74 vector, an AAV Anc80 vector, an AAVPHP.B vector, an AAVhu68 vector, an AAV-DJ vector, and others suitable for gene therapy.

AAV vectors are DNA parvoviruses that are nonpathogenic for mammals. Briefly, AAV-based vectors have the rep and cap viral genes that account for 96% of the viral genome removed, leaving the two flanking 145 base pair inverted terminal repeats (ITR) which are used to initiate viral DNA replication, packaging, and integration.

Further embodiments include use of other serotype capsids to create an AAV1 vector, an AAV2 vector, an AAV3 vector, an AAV4 vector, an AAV5 vector, an AAV6 vector, an AAV7 vector, an AAV8 vector, an AAV9 vector, an AAVrhS vector, an AAVrh10 vector, an AAVrh33 vector, an AAVrh34 vector, an AAVrh74 vector, an AAV Anc80 vector, an AAVPHP.B vector, an AAV-DJ vector, and others suitable for gene therapy. Optionally, the AAV viral capsid is AAV2/9, AAV9, AAVrhS, AAVrh10, AAVAnc80, or AAV PHP.B.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements is often increased to 50 bp apart before activity begins to decline. Depending on the promoter, it appears that individual elements function either cooperatively or independently to activate transcription.

An example of a promoter that is capable of expressing a stabilized protein, such as a modified α-GAL polypeptide or a modified PPT-1 polypeptide transgene in a mammalian T-cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving expression from transgenes cloned into a lentiviral vector (see, e.g., Milone et al., Mol. Ther. 17(8): 1453-1464 (2009)). Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences are sometimes also used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, gene therapy vectors are not contemplated to be limited to the use of constitutive promoters. Inducible promoters are also contemplated here. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline-regulated promoter. In some embodiments, the promoter is an α-GAL promoter.

In order to assess the expression of a modified polypeptide the expression vector to be introduced into a cell often contains either a selectable marker gene or a reporter gene or both to facilitate identification and selection of expressing cells from the population of cells sought to be transfected or infected through viral vectors. In other aspects, the selectable marker is often carried on a separate piece of DNA and used in a co-transfection procedure. Both selectable markers and reporter genes are sometimes flanked with appropriate regulatory sequences to enable expression in the host cells. Useful selectable markers include, for example, antibiotic-resistance genes, such as neo and the like.

Methods of introducing and expressing genes into a cell are suitable for methods herein. In the context of an expression vector, the vector is readily introduced into a host cell, e.g., mammalian, bacterial, yeast, or insect cell by any method in the art. For example, the expression vector is transferred into a host cell by physical, chemical, or biological means.

Physical methods for introducing a polynucleotide into a host cell include calcium phosphate precipitation, lipofection, particle bombardment, microinjection, gene gun, electroporation, and the like. Methods for producing cells comprising vectors and/or exogenous nucleic acids are suitable for methods herein (see, e.g., Sambrook et al., 2012, Molecular Cloning: A Laboratory Manual, volumes 1-4, Cold Spring Harbor Press, NY). One method for the introduction of a polynucleotide into a host cell is calcium phosphate transfection Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid is associated with a lipid. The nucleic acid associated with a lipid, in some embodiments, is encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, in some embodiments, liposomes are present in a bilayer structure, as micelles, or with a "collapsed" structure. Alternately, liposomes are simply interspersed in a solution, possibly forming aggregates that are not uniform in size or shape. Lipids are fatty substances which are, in some embodiments, naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use are obtained from commercial sources. For example, in some embodiments, dimyristyl phosphatidylcholine ("DMPC") is obtained from Sigma, St. Louis, Mo.; in some embodiments, dicetyl phosphate ("DCP") is obtained from K & K Laboratories (Plainview, N.Y.); cholesterol ("Choi"), in some embodiments, is obtained from Calbiochem-Behring; dimyristyl phosphatidylglycerol ("DMPG") and other lipids are often obtained from Avanti Polar Lipids, Inc. (Birmingham, Ala.). Stock solutions of lipids in chloroform or chloroform/methanol are often stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes are often characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids, in some embodiments, assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the a modified α-GAL polypeptide in order to confirm the presence of the recombinant DNA sequence in the host cell, a variety of assays are contemplated to be performed. Such assays include, for example, "molecular biological" assays suitable for methods herein, such as Southern and Northern blotting, RT-PCR and PCR; "biochemical" assays, such as detecting the presence or absence of a particular peptide, e.g., by immunological means (ELISAs and western blots) or by assays described herein to identify agents falling within the scope herein.

The present disclosure further provides a vector comprising a modified polypeptide encoding nucleic acid molecule. In one aspect, a therapeutic fusion protein vector is capable of being directly transduced into a cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the modified polypeptide construct in mammalian cells. In one aspect, the mammalian cell is a human cell.

Pharmaceutical Compositions

Provided herein are pharmaceutical compositions comprising a modified polypeptide a stabilized form of a protein for treating a genetic disorder, the stabilized form comprising one or more non-native cysteine residues that form a disulfide bridge between non-native cysteines within the protein or between non-native cysteines of two monomers of the protein and (ii) a pharmaceutically acceptable excipient. In some embodiments, the modified polypeptide forms a homodimer. In some embodiments, the homodimer is stabilized by a disulfide bond. In some embodiments, the modified polypeptide shows increased half-life at pH 7.4 compared with a wild type polypeptide.

Additionally provided herein are pharmaceutical compositions comprising (i) a modified α-GAL polypeptide, wherein the modified α-GAL polypeptide comprises cysteine substitutions of an α-GAL polypeptide sequence and (ii) a pharmaceutically acceptable excipient. Contemplated substitutions include: (i) D233C and I359C; and (ii) M51C and G360C. In some embodiments, the modified α-GAL polypeptide comprises cysteine substitutions of an α-GAL polypeptide sequence of D233C and I359C. In some embodiments, the modified α-GAL polypeptide comprises cysteine substitutions of an α-GAL polypeptide sequence of M51C and G360C. In some embodiments, the modified α-GAL polypeptide forms a homodimer. In some embodiments, the homodimer is stabilized by a disulfide bond. In some embodiments, the modified α-GAL polypeptide shows increased half-life at pH 7.4 compared with a wild type α-GAL polypeptide. In some embodiments, the composition comprises a chaperone. In some embodiments, the chaperone comprises Migalastat.

Further provided herein are pharmaceutical compositions comprising (i) a modified PPT-1 polypeptide, wherein the modified PPT-1 polypeptide comprises cysteine substitutions of a PPT-1 polypeptide sequence and (ii) a pharmaceutically acceptable excipient. Contemplated substitutions include A171C and A183C. In some embodiments, the modified PPT-1 polypeptide forms a homodimer. In some embodiments, the homodimer is stabilized by a disulfide bond. In some embodiments, the modified PPT-1 polypeptide shows increased half-life at pH 7.4 compared with a wild type PPT-1 polypeptide. In some embodiments, the composition comprises a chaperone.

Suitable excipients for pharmaceutical compositions herein include but are not limited to saline, maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate.

In some embodiments, pharmaceutical compositions herein comprise modified α-GAL polypeptides herein having an increased half-life at pH 4.6 compared with a wild type α-GAL polypeptide. In some embodiments, the half-life at pH 4.6 is at least 50% greater than a wild type α-GAL polypeptide. In some embodiments, the half-life at pH 4.6 is at least 150% greater than a wild type α-GAL polypeptide. In some embodiments, the half-life at pH 4.6 is at least 200% greater than a wild type α-GAL polypeptide. In some embodiments, the half-life at pH 4.6 is at least 250% greater than a wild type α-GAL polypeptide. In some embodiments, the half-life at pH 4.6 is at least 300% greater than a wild type α-GAL polypeptide. In some embodiments, the half-life at pH 4.6 is at least 350% greater than a wild type α-GAL polypeptide. In some embodiments, the half-life at pH 4.6 is at least 400% greater than a wild type α-GAL polypeptide.

In some embodiments, pharmaceutical compositions herein comprise modified PPT-1 polypeptides herein having an increased half-life at pH 4.6 compared with a wild type PPT-1 polypeptide. In some embodiments, the half-life at pH 4.6 is at least 50% greater than a wild type PPT-1 polypeptide. In some embodiments, the half-life at pH 4.6 is at least 150% greater than a wild type PPT-1 polypeptide. In some embodiments, the half-life at pH 4.6 is at least 200% greater than a wild type PPT-1 polypeptide. In some embodiments, the half-life at pH 4.6 is at least 250% greater than a wild type PPT-1 polypeptide. In some embodiments, the half-life at pH 4.6 is at least 300% greater than a wild type PPT-1 polypeptide. In some embodiments, the half-life at pH 4.6 is at least 350% greater than a wild type PPT-1 polypeptide. In some embodiments, the half-life at pH 4.6 is at least 400% greater than a wild type PPT-1 polypeptide.

In some embodiments, pharmaceutical compositions herein comprise modified α-GAL polypeptides having an increased half-life at pH 7.4. In some embodiments, the half-life at pH 7.4. is at least 50% greater than a wild type α-GAL polypeptide. In some embodiments, the half-life at pH 7.4 is at least 150% greater than a wild type α-GAL polypeptide. In some embodiments, the half-life at pH 7.4 is at least 200% greater than a wild type α-GAL polypeptide. In some embodiments, the half-life at pH 7.4 is at least 250% greater than a wild type α-GAL polypeptide. In some embodiments, the half-life at pH 7.4 is at least 300% greater than a wild type α-GAL polypeptide. In some embodiments, the half-life at pH 7.4 is at least 350% greater than a wild type α-GAL polypeptide. In some embodiments, the half-life at pH 7.4 is at least 400% greater than a wild type α-GAL polypeptide. In some embodiments, the half-life at pH 7.4 is at least 500% greater than a wild type α-GAL polypeptide. In some embodiments, the half-life at pH 7.4 is at least 600% greater than a wild type α-GAL polypeptide. In some embodiments, the half-life at pH 7.4 is at least 700% greater than a wild type α-GAL polypeptide. In some embodiments, the half-life at pH 7.4 is at least 800% greater than a wild type α-GAL polypeptide. In some embodiments, the half-life at pH 7.4 is at least 900% greater than a wild type α-GAL polypeptide. In some embodiments, the half-life at pH 7.4 is at least 1000% greater than a wild type α-GAL polypeptide.

In some embodiments, pharmaceutical compositions herein comprise modified PPT-1 polypeptides having an increased half-life at pH 7.4. In some embodiments, the half-life at pH 7.4. is at least 50% greater than a wild type PPT-1 polypeptide. In some embodiments, the half-life at pH 7.4 is at least 150% greater than a wild type PPT-1 polypeptide. In some embodiments, the half-life at pH 7.4 is at least 200% greater than a wild type PPT-1 polypeptide. In some embodiments, the half-life at pH 7.4 is at least 250% greater than a wild type PPT-1 polypeptide. In some embodiments, the half-life at pH 7.4 is at least 300% greater than a wild type PPT-1 polypeptide. In some embodiments, the half-life at pH 7.4 is at least 350% greater than a wild type PPT-1 polypeptide. In some embodiments, the half-life at pH 7.4 is at least 400% greater than a wild type PPT-1 polypeptide. In some embodiments, the half-life at pH 7.4 is at least 500% greater than a wild type PPT-1 polypeptide. In some embodiments, the half-life at pH 7.4 is at least 600% greater than a wild type PPT-1 polypeptide. In some embodiments, the half-life at pH 7.4 is at least 700% greater than a wild type PPT-1 polypeptide. In some embodiments, the half-life at pH 7.4 is at least 800% greater than a wild type PPT-1 polypeptide. In some embodiments, the half-life at pH 7.4 is at least 900% greater than a wild type PPT-1 polypeptide. In some embodiments, the half-life at pH 7.4 is at least 1000% greater than a wild type PPT-1 polypeptide.

Methods of Treatment
Gene Therapy Methods

Also provided herein are methods of ameliorating at least one symptom of a genetic disease in a subject in need thereof. Some such methods comprise administering at least one dose of a composition comprising a gene therapy a nucleic acid encoding a stabilized form of a protein for treating a genetic disorder, the stabilized form comprising one or more non-native cysteine residues that form a disulfide bridge between non-native cysteines within the protein or between non-native cysteines of two monomers of the protein. In some embodiments, the nucleic acid encodes a polypeptide which forms a homodimer. In some embodiments, the homodimer is stabilized by a disulfide bond. In some embodiments, the nucleic acid encodes a polypeptide having increased half-life at pH 7.4 compared with a wild type polypeptide. In some embodiments, the promoter is a constitutive promoter. In some embodiments, the promoter is a tissue-specific promoter. In some embodiments, the nucleic acid comprises at least a portion of a virus. In some embodiments, the virus is selected from wherein the virus comprises a retrovirus, an adenovirus, an adeno associated virus, a lentivirus, or a herpes virus. In some embodiments, the nucleic acid is packaged within in a viral capsid protein. In some embodiments, the at least one symptom is selected from one or more of pain, skin discoloration, inability to sweat, eye cloudiness, gastrointestinal dysfunction, tinnitus, hearing loss, mitral valve prolapse, heart disease, joint pain, renal failure, and kidney dysfunction. In some embodiments, at least one symptom is reduced with a single administration of the gene therapy nucleic acid construct. In some embodiments, the method further comprises measuring an activity in a tissue obtained from the subject following treatment.

In some embodiments the gene therapy vector or pharmaceutical composition is administered to the cerebrospinal fluid. In some embodiments, the gene therapy vector or pharmaceutical composition is delivered by intrathecal, intracerebroventricular, intraperenchymal, or intravenous injection, or a combination thereof. In some embodiments, the gene therapy vector or pharmaceutical composition is administered by intrathecal injection. In some embodiments, the gene therapy vector or pharmaceutical composition is administered via intravenous injection.

In some embodiments, the genetic disorder is a neurological disorder. In some embodiments, the genetic disorder is a lysosomal storage disorder. In some embodiments, genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), chronic granulomatous disease (CGD), infantile, juvenile and adult forms of neuronal ceroid lipofuscinosis, and CDKL5 deficiency disease.

Also provided herein are methods of ameliorating at least one symptom of Fabry disease in a subject in need thereof. Some such methods comprise administering at least one dose of a composition comprising a gene therapy nucleic acid construct comprising at least one promoter and a nucleic acid encoding a modified α-GAL polypeptide comprising cysteine substitutions of an α-GAL polypeptide sequence. Modified α-GAL polypeptides are contemplated to comprise cysteine substitutions including: (i) R49C and G361C; (ii) R49C and G360C; (iii) D233C and I359C; (iv) M51C and G360C; and (v) S276C. In some embodiments, the nucleic acid encodes a polypeptide comprising cysteine substitutions of an α-GAL polypeptide sequence selected from the group consisting of: (i) D233C and I359C; and (ii) M51C and G360C. In some embodiments, the nucleic acid encodes a polypeptide comprising cysteine substitutions of an α-GAL polypeptide sequence of D233C and I359C. In some embodiments, the nucleic acid encodes a polypeptide comprising cysteine substitutions of an α-GAL polypeptide sequence of M51C and G360C. In some embodiments, the nucleic acid encodes a polypeptide which forms a homodimer. In some embodiments, the homodimer is stabilized by a disulfide bond. In some embodiments, the nucleic acid encodes a modified α-GAL polypeptide having increased half-life at pH 7.4 compared with a wild type α-GAL polypeptide. In some embodiments, the promoter is a constitutive promoter. In some embodiments, the promoter is a tissue-specific promoter. In some embodiments, the nucleic acid comprises at least a portion of a virus. In some embodiments, the virus is selected from wherein the virus comprises a retrovirus, an adenovirus, an adeno associated virus, a lentivirus, or a herpes virus. In some embodiments, the nucleic acid is packaged within in a viral capsid protein. In some embodiments, the at least one symptom is selected from one or more of pain, skin discoloration, inability to sweat, eye cloudiness, gastrointestinal dysfunction, tinnitus, hearing loss, mitral valve prolapse, heart disease, joint pain, renal failure, and kidney dysfunction. In some embodiments, at least one symptom is reduced with a single administration of the gene therapy nucleic acid construct. In some embodiments, the method further comprises measuring an α-GAL activity in a tissue obtained from the subject following treatment. In some embodiments, the method further comprises administering a chaperone. In some embodiments, the chaperone comprises Migalastat.

Also provided herein are methods of ameliorating at least one symptom of CLN1 disease in a subject in need thereof. Some such methods comprise administering at least one dose of a composition comprising a gene therapy nucleic acid construct comprising at least one promoter and a nucleic acid encoding a modified PPT-1 polypeptide comprising cysteine substitutions of PPT-1 polypeptide sequence. Modified PPT-1 polypeptides are contemplated to comprise cysteine substitutions including A171C and A183C. In some embodiments, the nucleic acid encodes a polypeptide which forms a homodimer. In some embodiments, the homodimer is stabilized by a disulfide bond. In some embodiments, the nucleic acid encodes a modified PPT-1 polypeptide having increased half-life at pH 7.4 compared with a wild type PPT-1 polypeptide. In some embodiments, the promoter is a constitutive promoter. In some embodiments, the promoter is a tissue-specific promoter. In some embodiments, the nucleic acid comprises at least a portion of a virus. In some embodiments, the virus is selected from wherein the virus comprises a retrovirus, an adenovirus, an adeno associated virus, a lentivirus, or a herpes virus. In some embodiments, the nucleic acid is packaged within in a viral capsid protein. In some embodiments, the at least one symptom is selected from one or more of pain, skin discoloration, inability to sweat, eye cloudiness, gastrointestinal dysfunction, tinnitus, hearing loss, mitral valve prolapse, heart disease, joint pain, renal failure, and kidney dysfunction. In some embodiments, at least one symptom is reduced with a single administration of the gene therapy nucleic acid construct. In some embodiments, the method further comprises measuring a PPT-1 activity in a tissue obtained from the subject following treatment. In some embodiments, the method further comprises administering a chaperone. In some embodiments, the chaperone comprises Migalastat.

In some embodiments, treatment via methods described herein delivers a gene encoding a therapeutic protein to a cell in need of the therapeutic protein. In some embodiments, the treatment delivers the gene to all somatic cells in the individual. In some embodiments, the treatment replaces the defective gene in the targeted cells. In some embodiments, cells treated ex vivo to express the therapeutic protein are delivered to the individual.

In some embodiments, gene therapy treatments herein comprise administering a nucleic acid encoding modified α-GAL polypeptides herein having an intracellular half-life that is increased by at least a factor of about 2, 2.5, 3, 3.5, 4, 4.5 or 5 compared to the half-life of wild type human α-GAL.

Enzyme Replacement Therapy Methods

Also provided method of ameliorating at least one symptom of a genetic disease in a subject in need thereof, the method comprising administering at least one dose of a composition comprising a stabilized form of a protein for treating a genetic disorder, wherein the stabilized form comprising one or more non-native cysteine residues that form a disulfide bridge between non-native cysteines within the protein or between non-native cysteines of two monomers of the protein. In some embodiments, the modified polypeptide forms a homodimer. In some embodiments, the homodimer is stabilized by a disulfide bond. In some embodiments, the modified polypeptide shows increased half-life at pH 7.4 compared with a wild type polypeptide. In some embodiments, the at least one symptom is selected from one or more of mental impairment, seizures, loss of speech, and loss of motor skills. In some embodiments, the method further comprises administering a chaperone. In some embodiments, the chaperone comprises Migalastat.

In some embodiments, the composition is administered via intrathecal, intracerebroventricular, intraperenchymal, subcutaneous, intramuscular, ocular, intravenous injection, or a combination thereof In some embodiments, the genetic disorder is a neurological disorder. In some embodiments, the genetic disorder is a lysosomal storage disorder. In some embodiments, genetic disorder is selected from the group consisting of aspartylglucosaminuria, Batten disease, cystinosis, Fabry disease, Gaucher disease type I, Gaucher disease type II, Gaucher disease type III, Pompe disease, Tay Sachs disease, Sandhoff disease, metachomatic leukodystrophy, mucolipidosis type I, mucolipidosis type II, mucolipidosis type III, mucolipidosis type IV, Hurler disease, Hunter disease, Sanfilippo disease type A, Sanfilippo disease type B, Sanfilippo disease type C, Sanfilippo disease type D, Morquio disease type A, Morquio disease type B, Maroteau-Lamy disease, Sly disease, Niemann-Pick disease type A, Niemann-Pick disease type B, Niemann-Pick disease type C1, Niemann-Pick disease type C2, Schindler disease type I, Schindler disease type II, adenosine deaminase severe combined immunodeficiency (ADA-SCID), chronic granulomatous disease (CGD), infantile, juvenile and adult forms of neuronal ceroid lipofuscinosis, and CDKL5 deficiency disease.

Also provided method of ameliorating at least one symptom of Fabry disease in a subject in need thereof, the method comprising administering at least one dose of a composition comprising a modified α-GAL polypeptide, wherein the modified α-GAL polypeptide comprises cysteine substitutions of an α-GAL polypeptide sequence. Contemplated cysteine substitutions include: (i) D233C and I359C; and (ii) M51C and G360C. In some embodiments, the modified α-GAL polypeptide cysteine substitutions of an α-GAL polypeptide sequence of D233C and I359C. In some embodiments, the modified α-GAL polypeptide cysteine substitutions of an α-GAL polypeptide sequence of M51C and G360C. In some embodiments, the modified α-GAL polypeptide forms a homodimer. In some embodiments, the homodimer is stabilized by a disulfide bond. In some embodiments, the modified α-GAL polypeptide shows increased half-life at pH 7.4 compared with a wild type α-GAL polypeptide. In some embodiments, the at least one symptom is selected from one or more of pain, skin discoloration, inability to sweat, eye cloudiness, gastrointestinal dysfunction, tinnitus, hearing loss, mitral valve prolapse, heart disease, joint pain, renal failure, and kidney dysfunction. In some embodiments, the method further comprises administering a chaperone. In some embodiments, the chaperone comprises Migalastat.

Also provided method of ameliorating at least one symptom of a CLN-1 disease in a subject in need thereof, the method comprising administering at least one dose of a composition comprising a modified PPT-1 polypeptide, wherein the PPT-1 polypeptide comprises one or more non-native cysteine residues that form a disulfide bridge between non-native cysteines within the protein or between non-native cysteines of two monomers of the protein. Contemplated cysteine substitutions include: A171C and A183C. In some embodiments, the modified PPT-1 polypeptide forms a homodimer. In some embodiments, the homodimer is stabilized by a disulfide bond. In some embodiments, the modified PPT-1 polypeptide shows increased half-life at pH 7.4 compared with a wild type PPT-1 polypeptide. In some embodiments, the at least one symptom is selected from one or more of mental impairment, seizures, loss of speech, and loss of motor skills. In some embodiments, the method further comprises administering a chaperone. In some embodiments, the chaperone comprises Migalastat.

In some embodiments, methods herein comprise administering modified polypeptides herein having an increased half-life compared with a wild type polypeptide. In some embodiments, the half-life is at least 50% greater than a wild type polypeptide. In some embodiments, the half-life is at least 150% greater than a wild type polypeptide. In some embodiments, the half-life is at least 200% greater than a wild type polypeptide. In some embodiments, the half-life is at least 250% greater than a wild type polypeptide. In some embodiments, the half-life is at least 300% greater than a wild type polypeptide. In some embodiments, the half-life is at least 350% greater than a wild type polypeptide.

In some embodiments, methods herein comprise administering modified α-GAL polypeptides herein having an increased half-life compared with a wild type α-GAL polypeptide. In some embodiments, the half-life is at least 50% greater than a wild type α-GAL polypeptide. In some embodiments, the half-life is at least 150% greater than a wild type α-GAL polypeptide. In some embodiments, the half-life is at least 200% greater than a wild type α-GAL polypeptide. In some embodiments, the half-life is at least 250% greater than a wild type α-GAL polypeptide. In some embodiments, the half-life is at least 300% greater than a wild type α-GAL polypeptide. In some embodiments, the half-life is at least 350% greater than a wild type α-GAL polypeptide.

In some embodiments, methods herein comprise administering modified PPT-1 polypeptides herein having an increased half-life compared with a wild type PPT-1 polypeptide. In some embodiments, the half-life is at least 50% greater than a wild type PPT-1 polypeptide. In some embodiments, the half-life is at least 150% greater than a wild type PPT-1 polypeptide. In some embodiments, the half-life is at least 200% greater than a wild type PPT-1 polypeptide. In some embodiments, the half-life is at least 250% greater than a wild type PPT-1 polypeptide. In some embodiments, the half-life is at least 300% greater than a wild type PPT-1 polypeptide. In some embodiments, the half-life is at least 350% greater than a wild type PPT-1 polypeptide.

Definitions

Stabilized" as used herein with respect to a protein refers to a modified protein (e.g., modified to contain non-native cysteine residues) that maintains one or more of its biological activities for a period of time that is longer than a corresponding protein without the modification. In some embodiments, stabilized proteins maintain biological activity for a time that is about 10%, 20%, 30%, 40%, 50%, 60%, 70%, 80%, 90%, 100%, 150%, 200%, 250%, 300%, 350%, 400%, 450% or 500% longer than the corresponding protein without the modification. In some embodiments, stabilized proteins maintain biological activity for a time that is at least 10% longer, at least 20% longer, at least 30% longer, at least 40% longer, at least 50% longer, at least 60% longer, at least 70% longer, at least 80% longer, at least 90% longer, at least 100% longer, at least 150% longer, at least 200% longer, at least 250% longer, at least 300% longer %, at least 350% longer, at least 400% longer, at least 450% longer or at least 500% longer than the corresponding protein without the modification. In some embodiments, the stabilized protein has a longer half-life compared to a corresponding protein without the non-native cysteines. In some embodiments, the stabilized protein has a longer half-life at pH 4.0 to pH 8.0, or pH 4.0 to 6.0, or pH 6.0 to 8.0 compared to a corresponding protein without the non-native cysteines. In some embodiments, the stabilized protein has a longer half-life at pH 4.5 to 5.0 or 7.0 to 7.5 compared to a corresponding protein without the non-native cysteines. In some embodiments, the stabilized protein has a longer half-life at pH 7.4 compared to a corresponding protein without the non-native cysteines. In some embodiments, the stabilized protein has a longer half-life at pH 4.6 compared to a corresponding protein without the non-native cysteines.

As used herein "ex vivo gene therapy" refers to methods where patient cells are genetically modified outside the subject, for example to express a therapeutic gene. Cells with the new genetic information are then returned to the subject from whom they were derived.

As used herein "in vivo gene therapy" refers to methods where a vector carrying the therapeutic gene(s) is directly administered to the subject.

As used herein "fusion protein" and "therapeutic fusion protein" are used interchangeably herein and refer to a therapeutic protein having at least one additional protein, peptide, or polypeptide, linked to it. In some instances, fusion proteins are a single protein molecule containing two or more proteins or fragments thereof, covalently linked via peptide bond within their respective peptide chains, without chemical linkers. In some embodiments, the fusion protein comprises a therapeutic protein and a signal peptide, a peptide that increases endocytosis of the fusion protein, or both. In some embodiments, the peptide that increases endocytosis is a peptide that binds CI-MPR.

As used herein "plasmid" refers to circular, double-stranded unit of DNA that replicates within a cell independently of the chromosomal DNA.

As used herein "promoter" refers to a site on DNA to which the enzyme RNA polymerase binds and initiates the transcription of DNA into RNA.

As used herein "somatic therapy" refers to methods where the manipulation of gene expression in cells that will be corrective to the patient but not inherited by the next generation. Somatic cells include all the non-reproductive cells in the human body As used herein "somatic cells" refers to all body cells except the reproductive cells.

As used herein "tropism" refers to preference of a vector, such as a virus for a certain cell or tissue type. Various factors determine the ability of a vector to infect a particular cell. Viruses, for example, must bind to specific cell surface receptors to enter a cell. Viruses are typically unable to infect a cell if it does not express the necessary receptors.

As used herein "vector", or "gene therapy vector", used interchangeably herein, refers to gene therapy delivery vehicles, or carriers, that deliver therapeutic genes to cells. A gene therapy vector is any vector suitable for use in gene therapy, e.g., any vector suitable for the therapeutic delivery of nucleic acid polymers (encoding a polypeptide or a variant thereof) into target cells (e.g., sensory neurons) of a patient. In some embodiments, the gene therapy vector delivers the nucleic acid encoding a therapeutic protein or therapeutic fusion protein to a cell where the therapeutic protein or fusion is expressed and secreted from the cell. The vector may be of any type, for example it may be a plasmid vector or a minicircle DNA. Typically, the vector is a viral vector. These include both genetically disabled viruses such as adenovirus and nonviral vectors such as liposomes. The viral vector may for example be derived from an adeno-associated virus (AAV), a retrovirus, a lentivirus, a herpes simplex virus, or an adenovirus. AAV derived vectors. The vector may comprise an AAV genome or a derivative thereof.

"Construct" as used herein refers to a nucleic acid molecule or sequence that encodes a therapeutic protein or fusion protein and optionally comprises additional sequences such as a translation initiation sequence or IRES sequence.

The term "transduction" is used to refer to the administration/delivery of the nucleic acid encoding the therapeutic protein to a target cell either in vivo or in vitro, via a replication-deficient rAAV of the disclosure resulting in expression of a functional polypeptide by the recipient cell. Transduction of cells with a gene therapy vector such as a rAAV of the disclosure results in sustained expression of polypeptide or RNA encoded by the rAAV. The present disclosure thus provides methods of administering/delivering to a subject a gene therapy vector such as an rAAV encoding a therapeutic protein by an intrathecal, intraretinal, intraocular, intravitreous, intracerebroventricular, intraparechymal, or intravenous route, or any combination thereof "Intrathecal" delivery refers to delivery into the space under the arachnoid membrane of the brain or spinal cord. In some embodiments, intrathecal administration is via intracisternal administration.

The terms "recipient", "individual", "subject", "host", and "patient", are used interchangeably herein and in some cases, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human.

As used herein, the terms "treatment," "treating," "ameliorating a symptom," and the like, in some cases, refer to administering an agent, or carrying out a procedure, for the purposes of obtaining a therapeutic effect, including inhibiting, attenuating, reducing, preventing or altering at least one aspect or marker of a disorder, in a statistically significant manner or in a clinically sgnificant manner. The term "ameliorate" or "treat" does not state or imply a cure for the underlying condition. "Treatment," or "to ameliorate" (and like) as used herein, may include treating a mammal, particularly in a human, and includes: (a) preventing the disorder or a symptom of a disorder from occurring in a subject which may be predisposed to the disorder but has not yet been diagnosed as having it (e.g., including disorders that may be associated with or caused by a primary disorder; (b) inhibiting the disorder, i.e., arresting its development; (c) relieving the disorder, i.e., causing regression of the disorder; and (d) improving at least one symptom of the disorder. Treating may refer to any indicia of success in the treatment or amelioration or prevention of a disorder, including any objective or subjective parameter such as abatement; remission; diminishing of symptoms or making the disorder condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with the disorder. The term "therapeutic effect" refers to the reduction, elimination, or prevention of the disorder, symptoms of the disorder, or side effects of the disorder in the subject.

The term "affinity" refers to the strength of binding between a molecule and its binding partner or receptor.

As used herein, the phrase "high affinity" refers to, for example, a therapeutic fusion containing such a peptide that binds CI-MPR which has an affinity to CI-MPR that is about 100 to 1,000 times or 500 to 1,000 times higher than that of the therapeutic protein without the peptide. In some embodiments, the affinity is at least 100, at least 500, or at least 1000 times higher than without the peptide. For example, where the therapeutic protein and CI-MPR are combined in relatively equal concentration, the peptide of high affinity will bind to the available CI-MPR so as to shift the equilibrium toward high concentration of the resulting complex.

"Secretion" as used herein refers to the release of a protein from a cell into, for example, the bloodstream to be carried to a tissue of interest or a site of action of the therapeutic protein. When a gene therapy product is secreted into the interstitial space of an organ, secretion can allow for cross-correction of neighboring cells.

"Delivery" as used herein means drug delivery. In some embodiments, the process of delivery means transporting a drug substance (e.g., therapeutic protein or fusion protein produced from a gene therapy vector) from outside of a cell (e.g., blood, tissue, or interstitial space) into a target cell for therapeutic activity of the drug substance.

"Engineering" or "protein engineering" as used here in refers to the manipulation of the structures of a protein by providing appropriate a nucleic acid sequence that encodes for the protein as to produce desired properties, or the synthesis of the protein with particular structures.

A "therapeutically effective amount" in some cases means the amount that, when administered to a subject for treating a disease, is sufficient to effect treatment for that disease.

As used herein, the term "about" a number refers to a range spanning that from 10% less than that number through 10% more than that number, and including values within the range such as the number itself.

As used herein, the term "comprising" an element or elements of a claim refers to those elements but does not preclude the inclusion of an additional element or elements.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Identifying Amino Acid Residues for Cysteine Substitution of Wild Type α-GAL The crystal structure of dimerized α-GAL (PDB ID 3HG3) was examined for potential sites for substituting in cysteine residues, generating additional disulfide bonds for enhanced stability (FIG. 1A). NAMD with CHARMM forcefields was used for the analysis. Based on the analysis, the cysteine mutants shown in Table 8 were prepared using standard methods of directed mutagenesis.

TABLE 8

α-GAL Disulfide Mutants

| Mutations | SEQ ID NO |
| --- | --- |
| R49C-G361C | 2 |
| R49C-G360C | 3 |
| M51C-G360C | 4 |
| D233C-I359C | 5 |
| S276C | 6 |

Figure 1B:
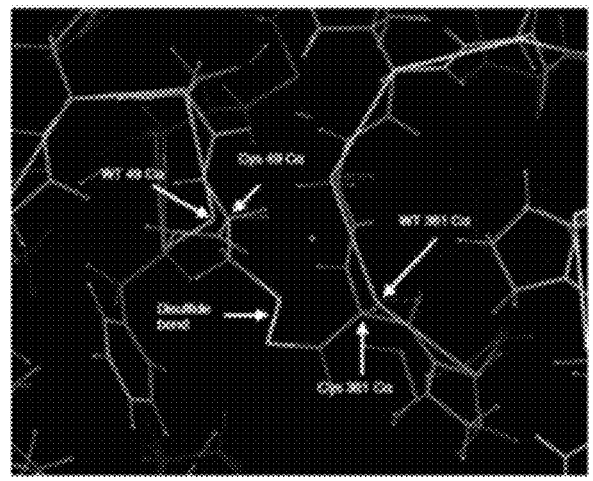

See also FIG. 1B. Amino acid sequences are provided in Table 1.

Example 2: Dimerization and Enzymatic Activity of Modified α-GAL

Figure 2A:
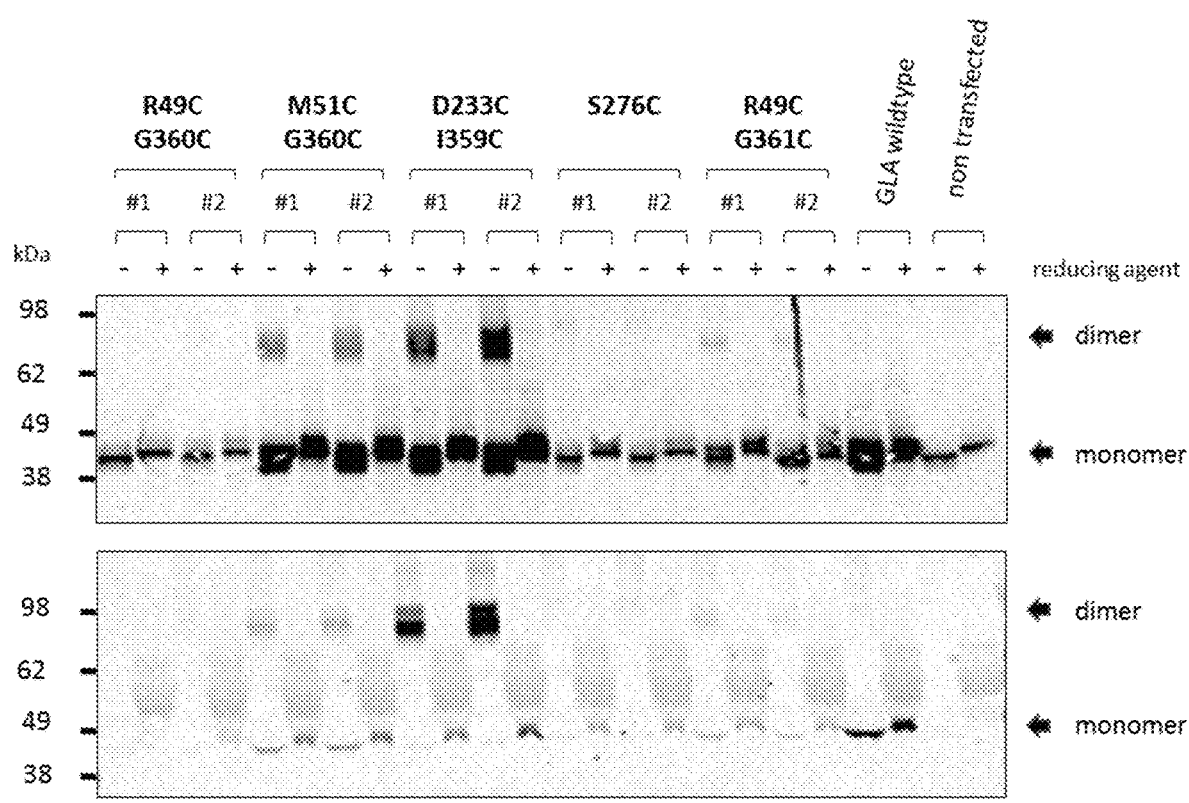
FIG. 2A shows modified α-GAL dimer formation.

The formation of disulfide bonded dimers of modified α-GAL was examined in cell lysate and culture media (FIG. 2A). Clones of each α-GAL construct were transiently expressed in 293HEK cell. Cell lysates and culture media were run on 4-12% gradient SDS-PAGE and transferred to nitrocellulose. α-GAL was detected by Western Blotting with rabbit monoclonal anti- α-GAL 1:2000 (abcam ab168341).

Figure 2B:
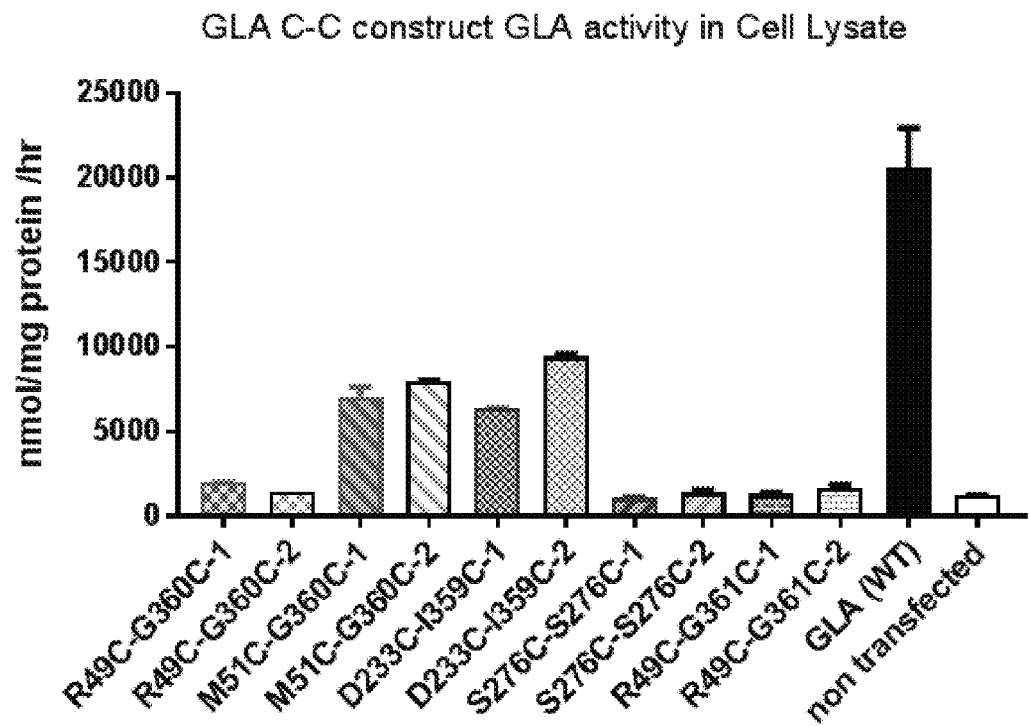
FIG. 2B shows modified α-GAL enzymatic activity.
Figure 2B:
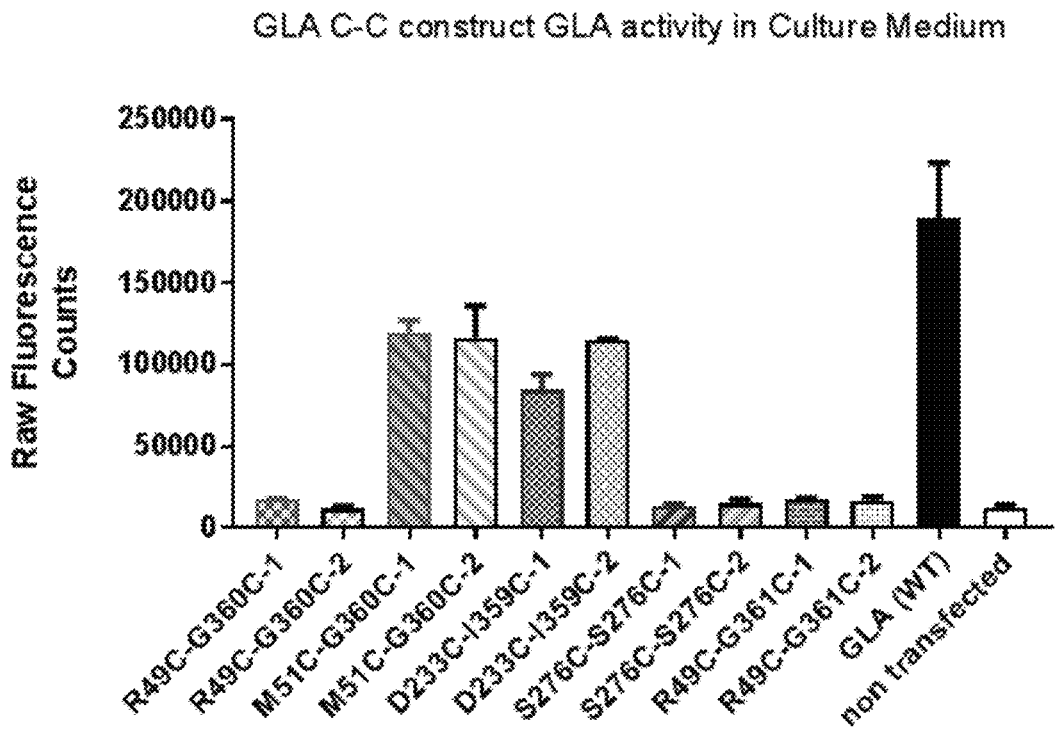

Reduced and non-reduced samples were subjected to electrophoresis and Western blotting. As seen in FIG. 2, M51C-G360C and D233C-I359C versions of the α-GAL readily formed disulfide bonded α-GAL dimers.

To prepare the samples, 1×10^6 cells were harvested with transient expression of α-GAL constructs. Cells were lysed in 500 ul 20 mM sodium phosphate buffer pH6.5, 0.25% TX-100. Cell lysate was centrifuged for 2 min @ 10,000 g and transfer supernatant to new tube. 40 ul of cell lysate or culture media was transferred to new tube and 16 µl of LDS 4× Sample Buffer was added with 6 µl of 10× Reducing agent (for reducing conditions). Sample mix prepared as below was heated at 95° C. for 5 minutes. 1×MOPS SDS running buffer was used for electrophoresis.

To test for enzymatic activity, lysate or culture medium were incubated with 4-methylumbelliferone-α-D-galactopyranoside (4-MUG) substrate for 1 hour. Enzymatic reaction was then stopped, and the α-GAL enzymatic activity was measured by fluorescence at excitation 360 nm and emission at 450 nm. As shown in FIG. 2B, the M51C-G360C and D233C-I359C disulfide α-GAL mutants were both enzymatically active. Because the specific activity and amount of α-GAL in each sample were not quantified, FIG. 2B does not provide a quantitative comparison of the activity between the wild type and mutant versions of α-GAL.

Example 3: Stability Analysis of Modified α-GAL in Acidic Environments Over Time To test pH stability over 24 h, transiently expressed mutant and wildtype α-GAL was captured using Concanavalin A (ConA) agarose pull-down according to standard methods. The ConA eluate was diluted in either pH 4.6 buffer or pH 7.4 buffer. Samples were pre-incubated at pH 4.6 or 7.4 at 0, 0.5, 1, 2, 4, 5 and 24 hours.

Figure 3A:
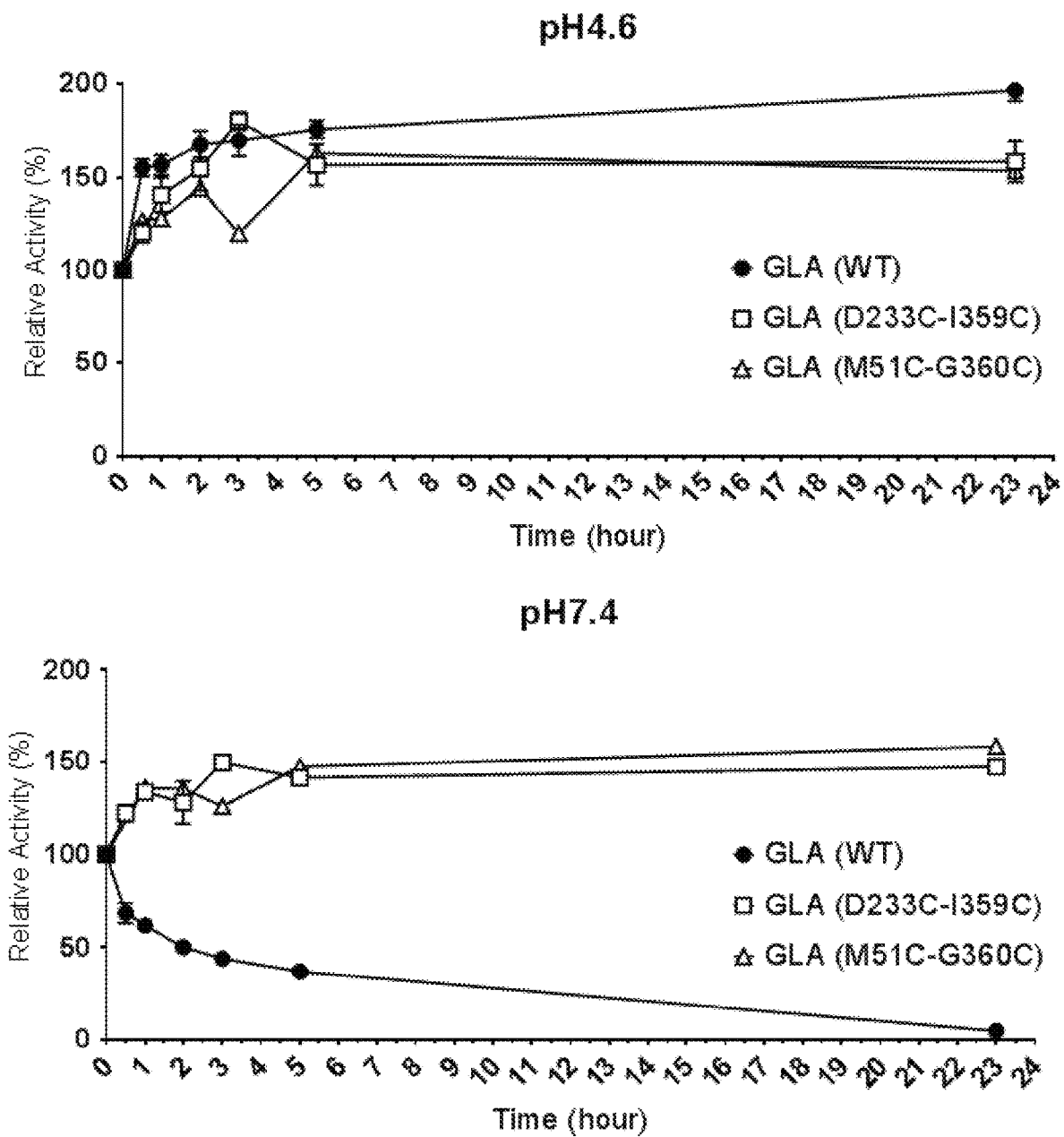
FIG. 3A shows stability of α-GAL at pH 4.6 and pH 7.4 over 24 hours.

To measure enzyme activity pH 4.6 buffer was added to each sample and tested for activity on a 4-MUG substrate. The reaction mixture was incubated 37° C. for 1 hour. The reaction was terminated by adding 125 uL Stop buffer (0.4 M Glycin-NaOH, pH 10.8) Fluorescence was read with Spectramax plate reader: Ex: 360 nm, Em: 450 nm. The results are shown in FIG. 3A.

Figure 3B:
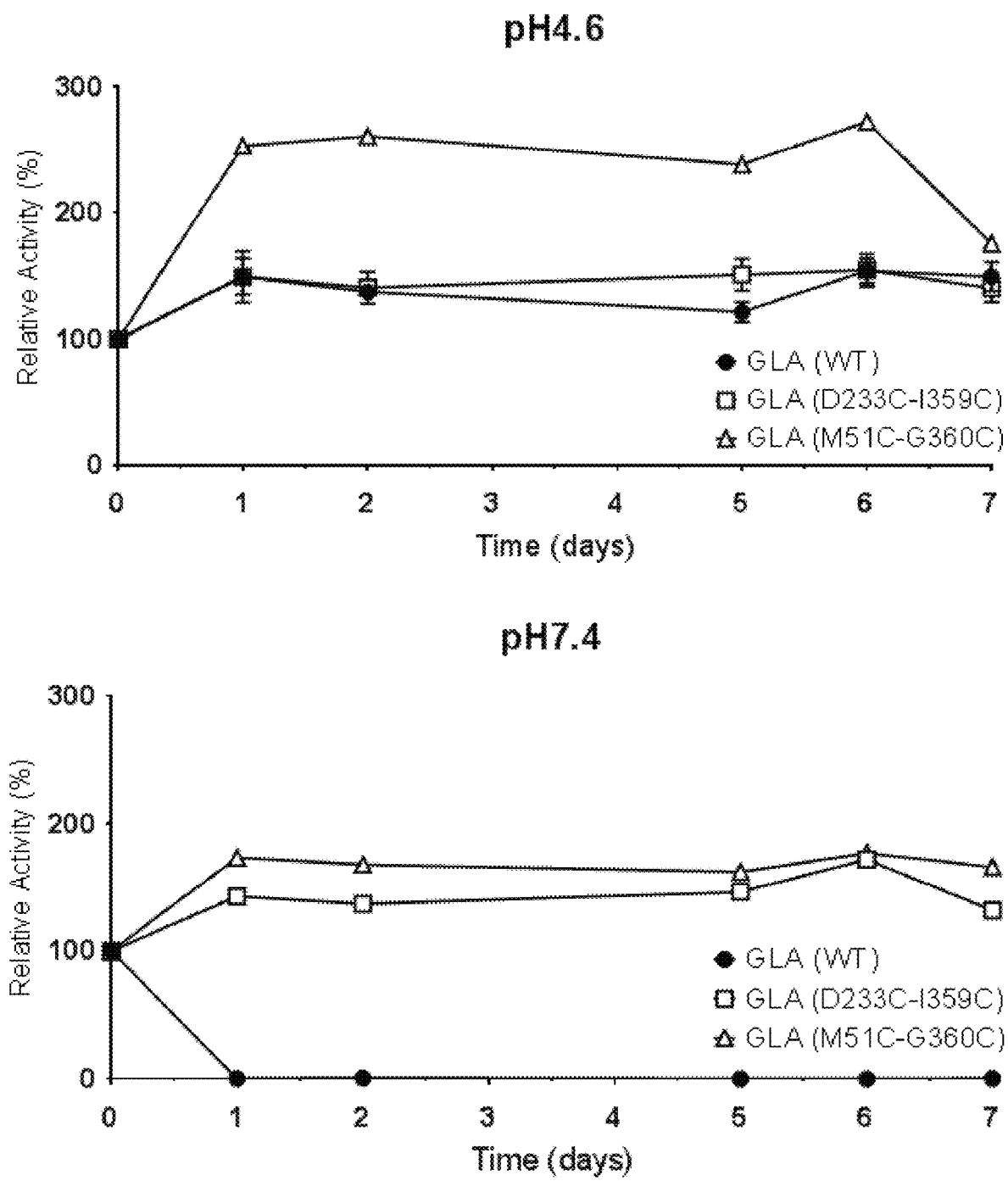
FIG. 3B shows stability of α-GAL at pH 4.6 and pH 7.4 over 7 days.

For long-term stability testing, transiently expressed modified and wild type α-GALs were isolated from culture media and enriched and purified using ConA agarose beads as described above. The eluted α-GAL was incubated in pH 4.6 or pH 7.4 for time course stability experiments. The time points included 0 hr, 0.5 hr, 1 hr, 2 hr, 4 hr, 5 hr, 24 hr, 2 days, 5 days, 6 days, and 7 days. FIG. 3B shows M51C-G360C α-GAL to be more stable over a span of 7 days than the wild type control at pH 4.6. Both modified α-GALs were substantially more stable than wild type control at pH 7.4 over 7 days.

Example 4: α-GAL Uptake and Enzymatic Assay by Fabry Patient Fibroblasts

Cell Uptake Protocol

To conduct the uptake assay, on day 1 300,000 Fabry patient fibroblasts (R301Q) were seeded per well in 6-well plates. On day 2, medium was replaced with 1.8 mL uptake medium and incubated for 1 hour at 37 C with 5% CO2. Cells were given a 200 uL dose of 250 nM enzyme (Fabrazyme, M51C-G360C, D233C-I359C and WT) prepared in uptake medium into 6-well prepared in step 2 for 16-18 hours. On day 3, 300 uL of 1 M Tris was added and incubated at room temperature for 30 min. 400 uL 1M NaH2SO4 was added and mixed. Cell plates were washed with 1 ml DPBS two times. 500 uL water was added into each well and cells were collected from the plate. Matricgreen was added before freezing at −80° C. freezer until assay. Plates were spun before enzyme and protein assays.

The protein assay was conducted by adding 20 uL cell lysate into 130 uL water. 150 uL BCA working reagent was added and incubated at 37 C.° for 2 hours. The plate was then read on a Spectramax.

The enzyme assay was conducted by adding 5 uL cell lysate into 15 uL Assay Buffer then adding 50 uL 4-MUG substrate. This was incubated at 37° C. for 1 hour. 125 uL Stop Buffer was added and read at the Spectramax.

As a control, frozen cell lysates were thawed at room temperature and sonicated for 5 min. 50 μL was transferred into 13 mL silanized glass tubes. 25 μL of Glucopsychosine (IS) (conc. 125 ng/mL) was added. 1 mL of methanol was added and the mixture was sonicated for approximately 10 min. 500 μL of 1N HCl was added, vortexed then sonicated for approximately 10 minutes. The mixture was then shaken for approximately 30 minutes at room temperature. Samples were centrifuged at 4,000 rpm for 10 min. at room temperature. Supernatant was transferred onto preconditioned SPE cartridges.

Solid samples were prepared by condition the SPE cartridges with 1 ml of methanol and 1 ml of Millipore water. Samples were loaded on the SPE cartridges. Cartridges were washed with 2 mL 0.1N HCl and then 2 mL MEOH. Samples were eluted with 2 mL 5% ammonium hydroxide in methanol into clean silanized glass. Samples were evaporated under nitrogen to dryness at 40° C. 25 μL of DMSO was added to each extract and vortexed. 125 μL (175 μL was used for run 03) of mobile phase B was added and vortexed. Samples were transferred into glass vials. 10 μl was injected onto analytical column.

Figure 4A:
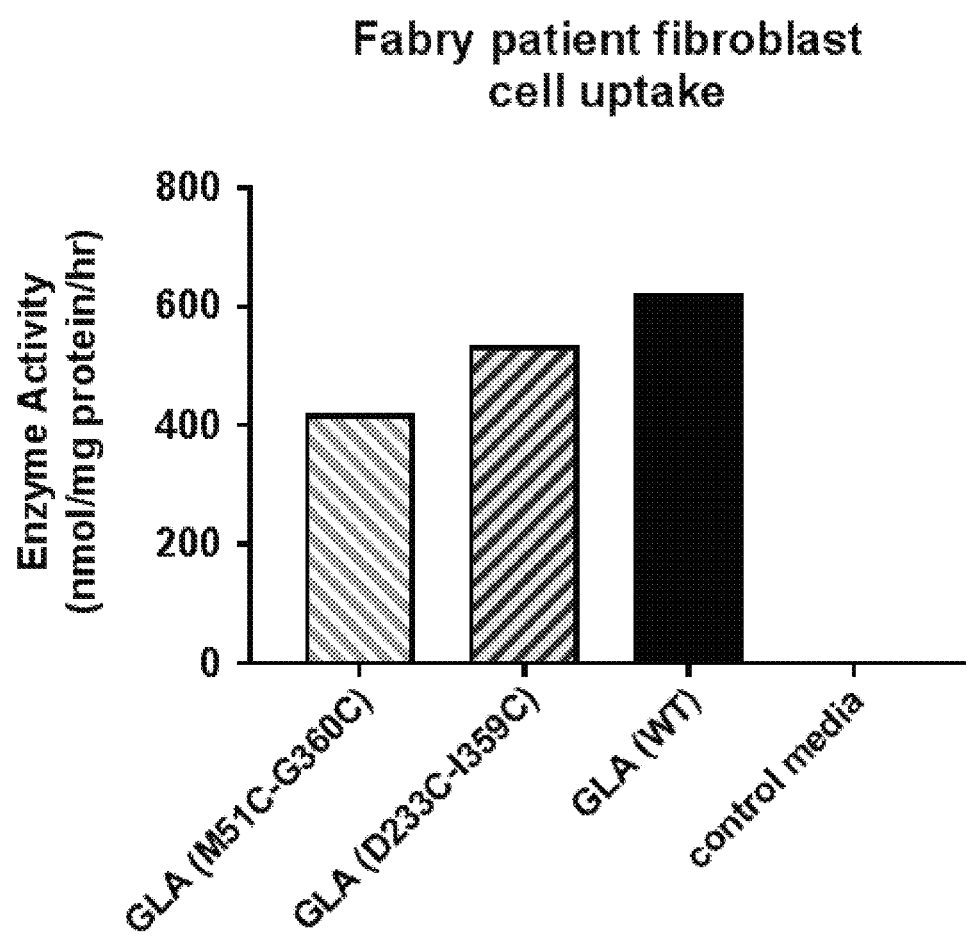
FIG. 4A shows uptake and enzymatic activity of modified α-GAL of Fabry patient fibroblasts.
Figure 4B:
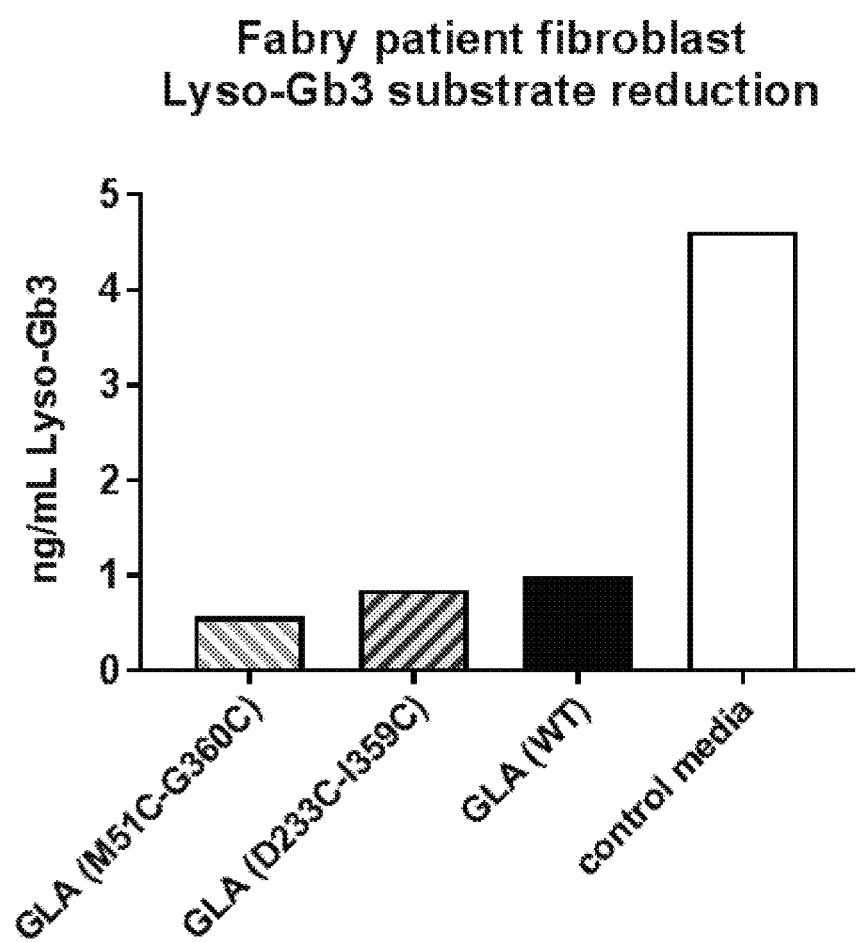
FIG. 4B shows reduction of globotriaosylsphingosine (lyso-Gb3) in Fabry patient fibroblasts.

Fibroblasts from Fabry disease patients were cultured and seeded in 6-well plates. Cells treated with wild type α-GALs were used as positive control for the uptake and subsequent enzymatic studies. Fibroblasts were incubated for 16 to 18 hr with wild type α-GAL, M51C-G360C α-GAL, or D233C-I359C α-GAL. The cells were then lysed for α-GAL enzymatic assay as determined by fluorescent output. FIG. 4A shows that both M51C-G360C and D233C-I359C α-GALs were able to restore α-GAL enzymatic activity at least as well wild type α-GAL. See FIG. 4B. Globotriaosylsphingosine (lyso-Gb3) is a biomarker for Fabry Disease. Successful treatment of Fabry Disease leads to significant reduction of lyso-Gb3 as determined by LC-MS/MS.

Example 5: Variant Homodimers Uptake in FB-14 (R301Q) Fabry Patient Fibroblasts

Figure 5:
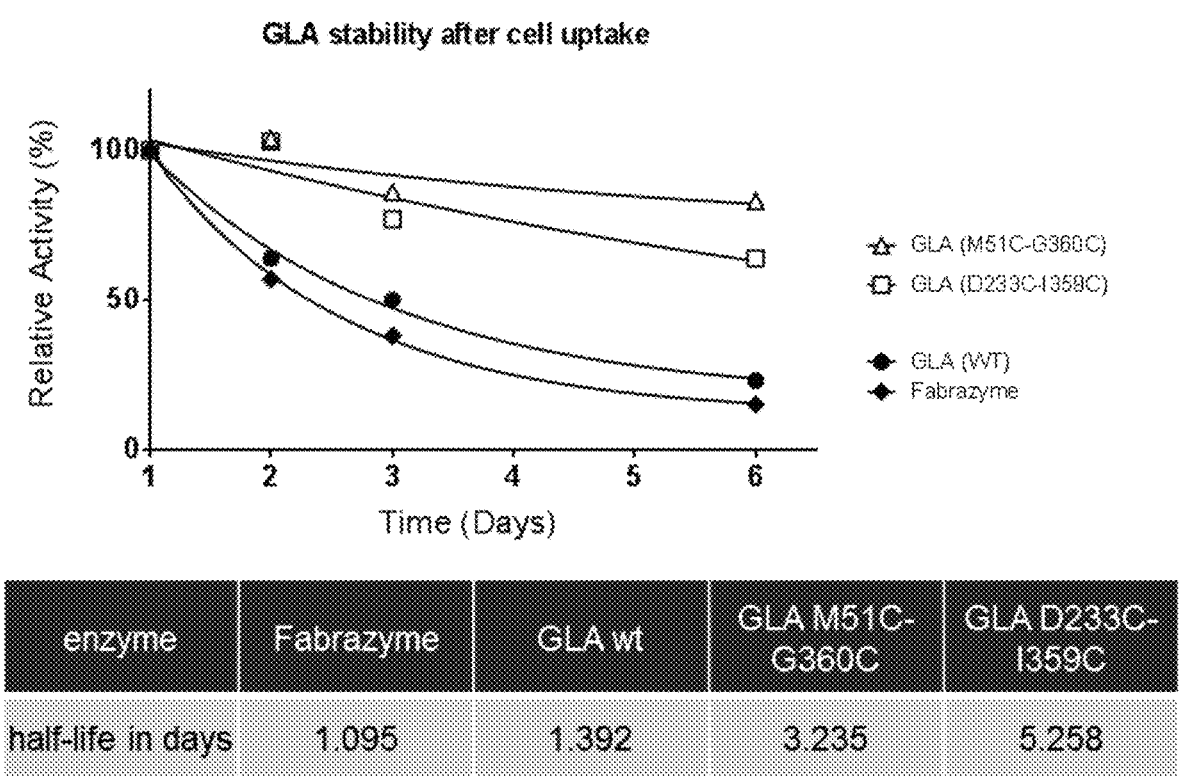
FIG. 5 shows activity of enhanced half-life of two α-GAL disulfide dimers in Fabry disease cells.

Fabry patient fibroblast cells were seeded in 6-well plate for Fabrazyme and α-GAL cell uptake studies. Cells were incubated for 16 h at 37 C, 5% CO2 incubator in uptake media containing 7 nM of either Fabrazyme, wild type α-GAL, M51C-G360C α-GAL, or D233C-I359C α-GAL. At day 1 cells were washed and further maintained in regular growth media for 5 additional days. Cells were harvested at time points indicated in FIG. 5. Cell lysates were used to determine enzyme activity. α-GAL enzyme activity was determined and normalized with cell lysate protein concentration as nmol/mg protein/hr. It was determined that the variant homodimers have 2-3-fold longer half-life inside the cell after cell uptake than wildtype and 3-4-fold longer than Fabrazyme (FIG. 5).

Example 6: Fabry Disease Gene Therapy in Mouse Model

The AAV vectors were diluted in sterile PBS. The AAV vectors included: AAVhu68.CB7.hGLAnatural.rBG, AAVhu68.CB7.hGLAco.rBG, and AAVhu68.CB7.hGLA-M51C-G360Cco.rBG.

Vector Production

The reference GLA sequence and the variant with the methionine to cysteine at position 51 and glycine to cysteine at position 360 were back-translated and the nucleotide sequence was codon optimized to generate a cis-plasmid for AAV production with the expression cassette under CB7 promoter. In addition, natural hGLA (reference sequence) cDNA was ordered and cloned into the same AAV-cis backbone to compare with a codon-optimized sequence. AAVhu68 vectors were produced and titrated as previously described (Lock, Alvira et al. 2010, "Rapid, simple, and versatile manufacturing of recombinant adeno-associated viral vectors at scale." Hum Gene Ther 21(10): 1259-1271). Briefly, HEK293 cells were triple-transfected and the culture supernatant was harvested, concentrated, and purified with an iodixanol gradient. The purified vectors were titrated with droplet digital PCR using primers targeting the rabbit Beta-globin polyA sequence as previously described (Lock M, R. Alvira, S. J. Chen and J. M. Wilson, "Absolute determination of single-stranded and self-complementary adeno-associated viral vector genome titers by droplet digital PCR." Hum Gene Ther Methods 25(2): 115-125 (2014)).

Animals

*Mus musculus*, Fabry mice Gla knock-out, in a C57BL/6/129 background founders were purchased at Jackson Labs (stock #003535—"also known as" α-Gal A KO mice"). The breeding colony was maintained at the Gene Therapy Program AAALAC accredited barrier mouse facility, using heterozygote to heterozygote mating in order to produce null and WT controls within the same litters. The Gla knock-out mouse is a widely used model for Fabry disease.

The mice appear clinically normal, but they exhibit a progressive accumulation of the GLA substrate Globotriaosylsphingosine (aka lyso-GB3) in plasma and Globotriaosylceramide (aka GL3, GB3) in liver, heart, kidney, skin small and large intestine and the central nervous system. The small size, reproducible phenotype, and efficient breeding allow quick studies that are optimal for preclinical candidates in vivo screening.

Animal holding rooms were maintained at a temperature range of 64-79° F. (18-26° C.) with a humidity range of 30-70%. Animals were housed with their parents and littermates until weaning and next in standard caging of 2 to 5 animals per cage in the Translational Research Laboratories (TRL) GTP vivarium. Cages, water bottles, and bedding substrates are autoclaved into the barrier facility. An automatically controlled 12-hour light/dark cycle was maintained. Each dark period began at 1900 hours (±30 minutes). Food was provided ad libitum (Purina, LabDiet®, 5053, Irradiated, PicoLab®, Rodent Diet 20, 25 lb). Water was accessible to all animals ad libitum via individually placed water bottle in each housing cage.

In Vivo Studies and Histology

Mice received $5 \times 10^{11}$ GCs (approximately $2.5 \times 10^{13}$ GC/kg) of AAVhu68.CB7.hGLA (various hGLA constructs) in 0.1 mL via the lateral tail vein, were bled on Day 7 and Day 21 post vector dosing for serum isolation and were terminally bled (for plasma isolation) and euthanized by exsanguination 28 days post injection. Tissues were promptly collected, starting with brain.

Tissues for histology were formalin-fixed and paraffin embedded using standard methods. Spinal cord with DRG (in bone) was fixed in ZF, decalcified in EDTA and processed according to standard procedures of the GTP Morphology Core. Zinc-formalin is used to obtain good tissue preservation and was used to stain the Gb3 storage by IHC and for morphology (H&E).

Immunostaining for GL3 was performed on formalin-fixed paraffin-embedded samples. Sections were deparaffinized, blocked with 1% donkey serum in PBS+0.2% Triton for 15 min, and then sequentially incubated with primary (Amsbio AMS.A2506, anti-Gb3 monoclonal antibody) and biotinylated secondary antibodies diluted in blocking buffer; an HRP based colorimetric reaction was used to detect the signal. Slides were reviewed in a blinded fashion by a board-certified Veterinary Pathologist.

Figure 6:
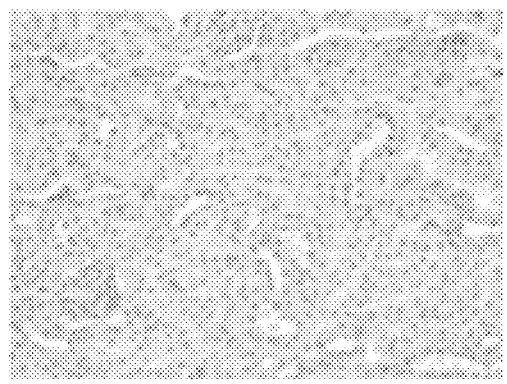
FIG. 6 shows GB3 substrate histology in wildtype mice and GLA knockout mice with and without treatment with modified α-GAL gene therapy.
Figure 6:
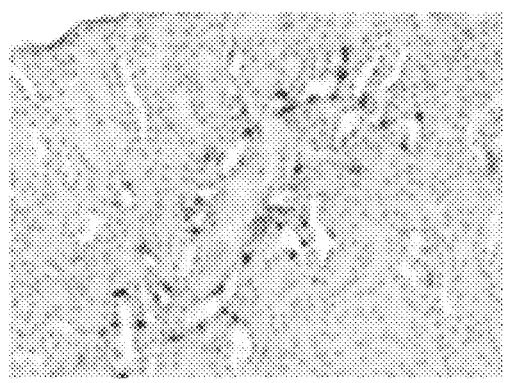
Figure 6:
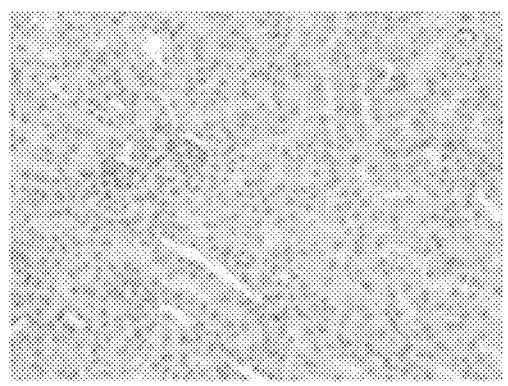

Fabry –/– mice vehicle PBS controls display marked GL3 (dark staining on IHC stained sections) accumulation. WT mice and all vector treated mice have near complete to complete clearance of GL3 storage (FIG. 6).

GLA Activity

Plasma or supernatant of homogenized tissues were mixed with 6 mM 4-MU-α-galactopyranoside pH 4.6, 90 mM GalNAc and incubated for three hours at 37° C. The reaction was stopped with 0.4 M glycine pH 10.8. Relative fluorescence units, RFUs were measured using a Victor3 fluorimeter, ex 355 nm and emission at 460 nm. Activity in units of nmol/mL/hr was calculated by interpolation from a standard curve of 4-MU. Activity levels in individual tissue samples were normalized for total protein content in the homogenate supernatant. Equal volumes are used for plasma samples.

Figure 7:
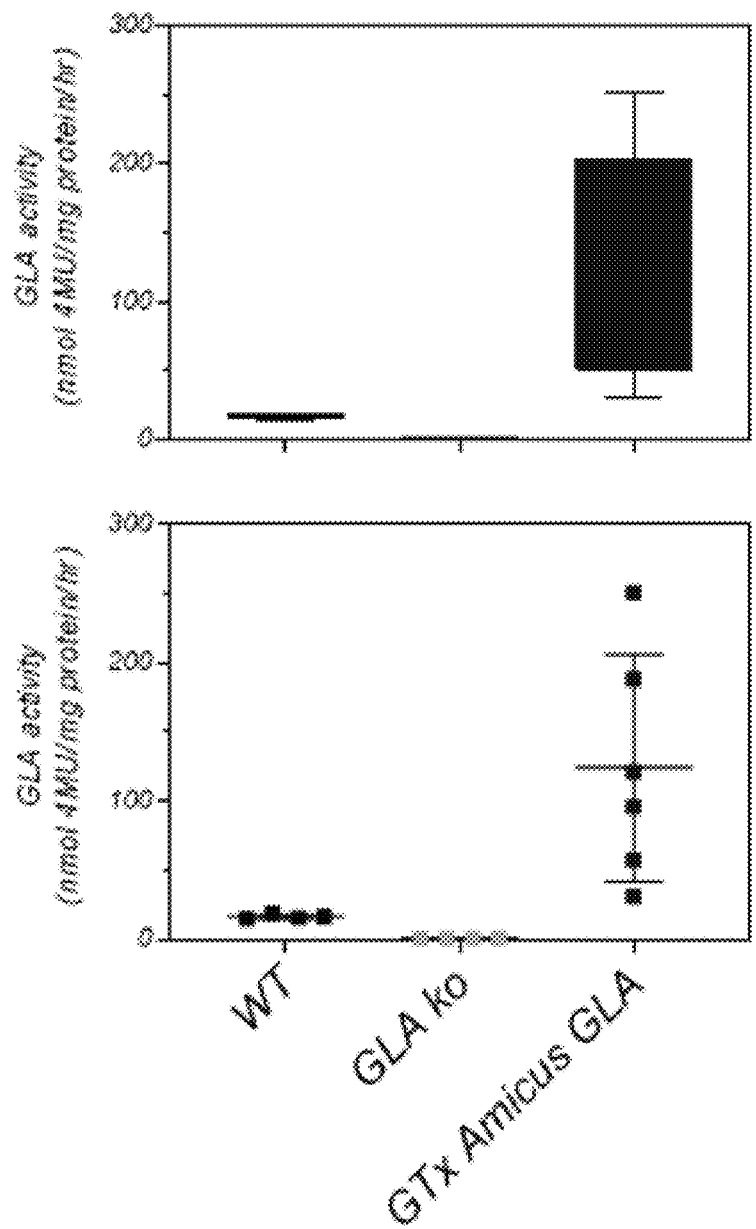
FIG. 7 shows GLA enzyme activity in wildtype mice and GLA knockout mice with and without treatment with modified α-GAL gene therapy.

Fabry –/– mice displayed a complete lack of α-Gal A activity. Treatment of Fabry mice with AAVhu68.CB7.hGLA-M51C-G360Cco.rBG GTx vector resulted in >7-fold higher GLA activity in kidney than wildtype (FIG. 7).

Quantitation of Globotriaosylceramide (Aka GL3, GB3) by LC-MS/MS

The GLA substrate, GL3, in tissue homogenate was quantified by a LC-MS/MS assay. Briefly, an internal standard was added to homogenate samples (50 µL) and the samples were processed using C18-based solid-phase extraction (SPE). A standard curve was prepared to known concentrations of GL3 (8.83 nM to 4.41 µM) from stocks containing twelve ceramide forms. Monitored responses from all twelve isoforms were to be summed and a ratio was generated with respect to internal standard in this assay. The resultant ratios of study samples were then compared against the prepared curve for GL3 quantification.

Figure 8:
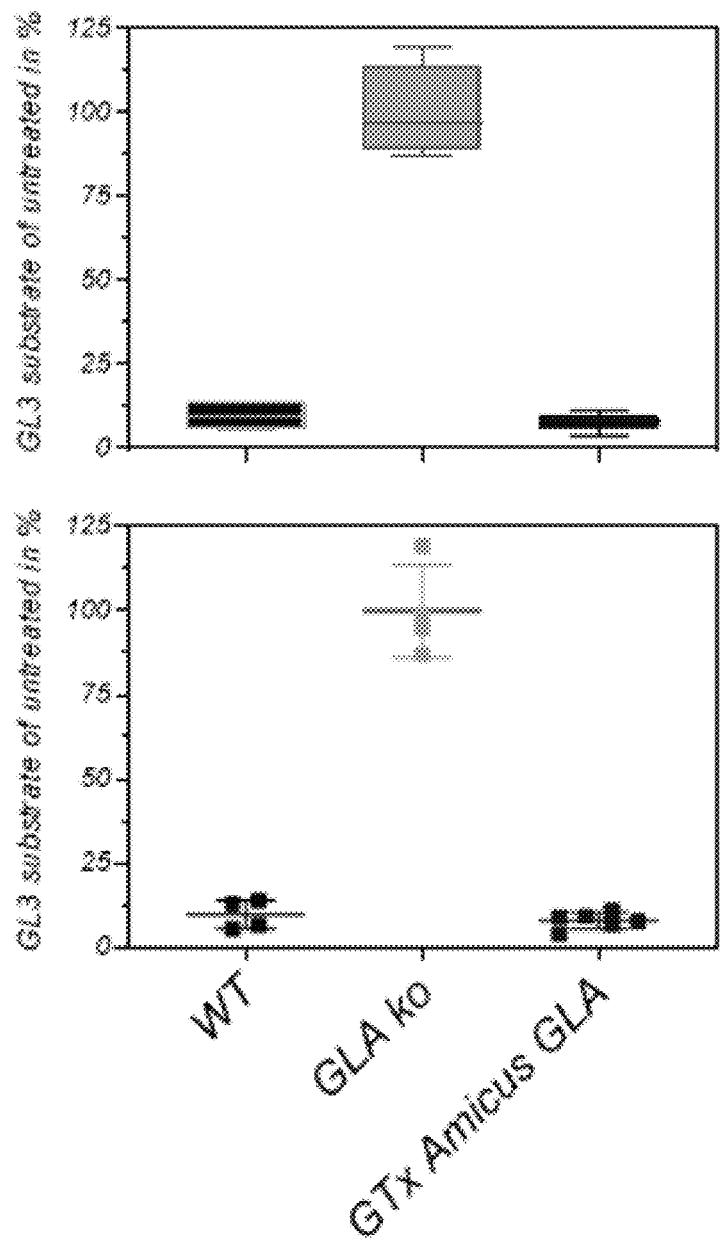
FIG. 8 shows GB3 substrate measured in kidney tissue lysate in wildtype mice and GLA knockout mice with and without treatment with modified α-GAL gene therapy.

Fabry –/– mice displayed a >10-fold accumulation of the GLA substrate Globotriaosylceramide (GL3). Treatment of Fabry mice with AAVhu68.CB7.hGLA-M51C-G360Cco.rBG GTx vector resulted in a completed reduction of GL3 in kidney to wildtype level (FIG. 8).

Quantitation of Globotriaosylsphingosine (Aka Lyso-GB3) by LC-MS/MS

The GLA substrate, lyso-GB3, in plasma is quantified by a LC-MS/MS assay. Briefly, a stable C13-labeled internal standard is added to the plasma samples (50 µL) and the samples are processed using C18/cation exchange mixed mode solid-phase extraction (SPE). A standard curve is prepared to known concentrations of lyso-GB3 (0.254 nM to 254 nM) and lyso-GB3 response of study samples are then compared against the prepared curve for lyso-GB3 quantification.

GLA Signature Peptide by LC/MS

Plasma is precipitated in 100% methanol and centrifuged. Supernatants are discarded. The pellet is spiked with a stable isotope-labeled peptide unique to hGLA as an internal standard and resuspended with trypsin and incubated at 37° C. for two hours. The digestion is stopped with 10% formic acid. Peptides are separated by C-18 reverse phase chromatography and identified and quantified by ESI-mass spectroscopy. The total GLA concentration in plasma is calculated from the signature peptide concentration.

Cell Surface Receptor Binding Assay

A 96-well plate is coated with receptor, washed, and blocked with BSA. CHO culture conditioned media or plasma containing equal activities of either rhGLA or engineered GLA is serially diluted three-fold to give a series of nine decreasing concentrations and incubated with co-coupled receptor. After incubation the plate is washed to remove any unbound GLA and 4-MU-α-galactopyranoside added for one hour at 37° C. The reaction is stopped with 1.0 M glycine, pH 10.5 and RFUs were read by a Spectramax fluorimeter; ex 370, emission 460. RFU's for each sample and are converted to activity in nmol/mL/hr by interpolation from a standard curve of 4-MU. Nonlinear regression is done using GraphPad Prism.

Example 7: Stabilized PPT-1 Constructs

A stabilized PPT-1 construct was engineered based on the crystal structure (PDB ID 3GRO). These two cysteines are predicted to form a disulfide bond, which stabilizes the structure and was found to extend the half-life of enzymatic function (see data below). The expression level of this construct in HEG 293 was found to be close to that of wildtype PPT-1.

Improved Stability and Half-Life of PPT-1 Enzyme

An intramolecular disulfide bridge was engineered into PPT-1 in order to stabilize the enzyme, as determined by measuring the half-life of the active enzyme. The residues that were mutated, A171C/A183C, were chosen because the equivalent residues in a homologous protein, PPT-2, form a disulfide bridge. This natural variation in a homologous protein was used to inform the engineering efforts in PPT-1.

Stability Testing of Construct PPT-1

Figure 9:
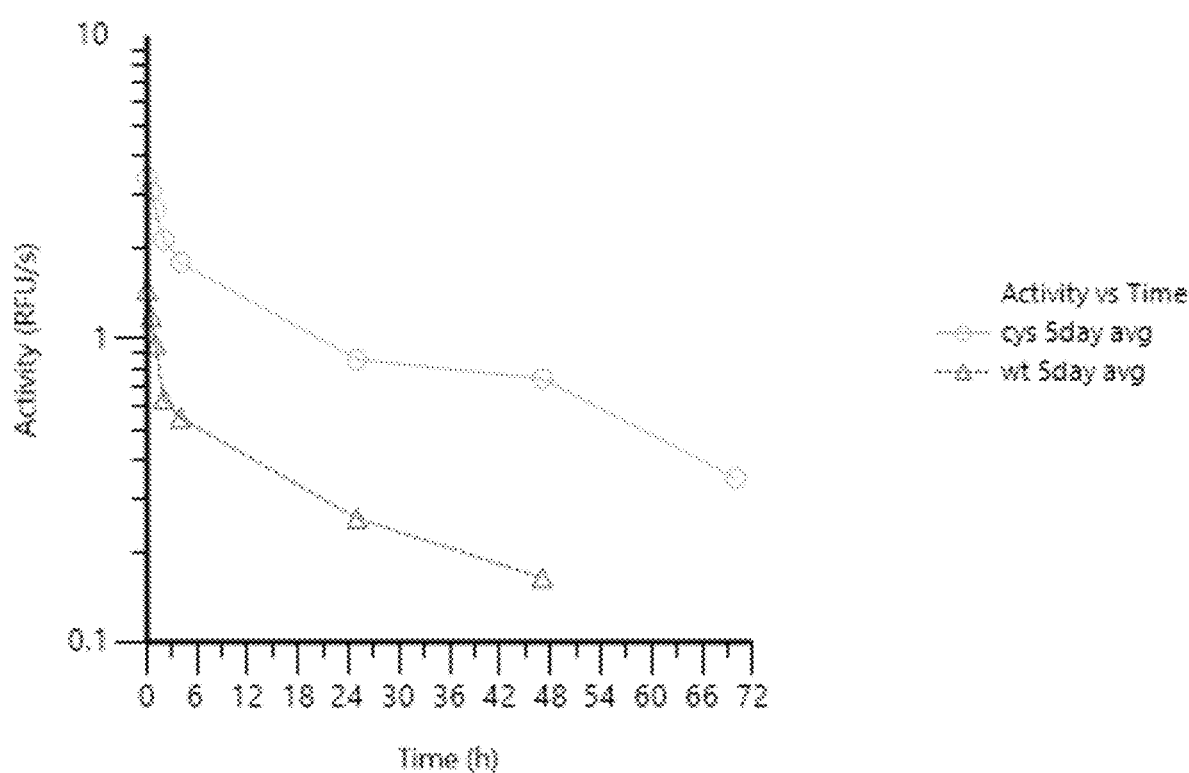
FIG. 9 shows WinNonlin analysis of enzymatic activity of palmitoyl protein thioesterase 1 (PPT-1) wildtype vs Construct PPT-1 mutant over time.

Construct PPT-1 was expressed transiently in HEK 293T cells and the conditioned media was harvested five days post-transfection. The same was done for wildtype PPT1. Enzyme activity assays were performed on both sets of conditioned media over a course of 48 or 72 hours. The amount of enzymatic activity retained over time was determined in order to compare the cysteine double mutant with WT. (FIG. 9).

Half-life was estimated in two ways representing the alpha and beta phases, as activity appears to be a biphasic elimination (see log plot adjacent to the PK table below). The alpha half-life was estimated during the early terminal or distribution phase, the beta half-life was estimated during the terminal elimination phase. For ATB200 total GAA protein analyses, the alpha phase is often reported as it is more meaningful for demonstrating effect of AT2221 on binding and stabilization of ATB200 while in blood, during distribution into tissues.

Pharmacokinetics of Construct PPT-1, including Co and AUCs, are reported. The $AUC_{infinity}$ was derived from the same elimination rate constant used to estimate the beta half-life.

TABLE 9

| PPT-1 Pharmacokinetics (5 day average) | | | | | |
|---|---|---|---|---|---|
| Construct | $C_0$ | $AUC_{0-t}$ | $AUC_{0-\infty}$ | $t_{1/2\alpha}$ | $t_{1/2\beta}$ |
| Wildtype | 1.46 | 15.9 | 21.0 | 1.7 | 23.1 |
| Cys-mutant | 3.40 | 65.6 | 80.3 | 2.8 | 28.2 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

What is claimed is:

1. A gene therapy vector comprising a nucleic acid construct comprising: a nucleic acid encoding a stabilized form of a protein that is defective or deficient in a genetic disorder, the stabilized form comprising one or more non-native cysteine residues that form a disulfide bridge between non-native cysteines within the protein or between non-native cysteines of two monomers of the protein, wherein:
the protein comprises a stabilized α-galactosidase A (α-GAL) protein further comprising one or more pairs of non-native cysteine residues compared to the wild-type α-GAL sequence (SEQ ID NO:1), selected from the group consisting of: (i) D233C and I359C; and (ii) M51C and G360C; and
the gene therapy vector is a viral vector selected from the group consisting of an adenovirus vector, an adeno-associated virus vector, a retrovirus vector, a lentivirus vector, and a herpes virus vector.

2. The gene therapy vector of claim 1, wherein the stabilized protein has a longer half-life at pH 7.4 compared to a corresponding protein without the non-native cysteines.

3. The gene therapy vector of claim 1, wherein the stabilized-protein can replace a protein that is defective or deficient in the genetic disorder.

4. The gene therapy vector of 1, wherein the stabilized protein can reduce or slow one or more symptoms associated with the genetic disorder.

5. The gene therapy vector of 1, wherein the stabilized protein is more effective at reducing or slowing one or more symptoms of the genetic disorder, compared to a wildtype protein.

6. The gene therapy vector of claim 1, wherein the viral vector genome comprises a recombinant AAV (rAAV) genome.

7. The gene therapy vector of claim 6, wherein the rAAV genome comprises a self-complementary genome.

8. The gene therapy vector of claim 6, wherein the rAAV genome comprises a first inverted terminal repeat and a second inverted terminal repeat.

9. The gene therapy vector of claim 6, wherein the rAAV genome further comprises an SV40 intron and a poly-adenylation sequence.

10. The gene therapy vector of claim 6, wherein the construct further comprises a nucleic acid sequence encoding an α-GAL protein, wherein the nucleic acid sequence is at least 85% identical to SEQ ID Nos: 7-12.

11. The gene therapy vector of claim 1, wherein the construct further comprises a promoter sequence.

12. The gene therapy vector of claim 11, wherein the promoter is a constitutive promoter or a tissue-specific promoter.

13. The gene therapy vector of claim 1, wherein the construct further comprises one or more nucleic acid sequences selected from the group consisting of: a Kozak sequence, a cricket paralysis virus internal ribosomal entry sequence (CrPV IRES), a nucleic acid sequence encoding a linker, a nucleic acid sequence encoding a signal sequence, and a nucleic acid sequence encoding an Insulin-like Growth Factor 2 peptide.

14. A pharmaceutical composition comprising the gene therapy vector of claim 1 and a pharmaceutically acceptable excipient, carrier, or diluent.

15. The pharmaceutical composition of claim 14, wherein the excipient is selected from the group consisting of saline, maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate.

16. The gene therapy vector of claim 1, wherein the stabilized protein comprises a pair of non-native cysteine residues at D233C and I359C of SEQ ID NO:1.

17. The gene therapy vector of claim 1, wherein the stabilized protein comprises a pair of non-native cysteine residues at M51C and G360C of SEQ ID NO:1.

18. The gene therapy vector of claim 16, wherein the stabilized protein comprises the amino acid sequence of SEQ ID NO:5.

19. The gene therapy vector of claim 18, wherein the stabilized protein comprises the amino acid sequence of SEQ ID NO:4.

20. The gene therapy vector of claim 1, wherein the construct further comprises a nucleic acid sequence encoding an a-GAL protein, wherein the nucleic acid sequence comprises at least one of SEQ ID NO: 15 and SEQ ID NO: 16.

* * * * *

SEQUENCE LISTING

```
<160> NUMBER OF SEQ ID NOS: 34

<210> SEQ ID NO 1
<211> LENGTH: 429
<212> TYPE: PRT
<213> ORGANISM: Homo sapiens

<400> SEQUENCE: 1

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190
```

Arg Thr Gly Arg Ser Ile Val Tyr Ser Cys Glu Trp Pro Leu Tyr Met
            195                 200                 205

Trp Pro Phe Gln Lys Pro Asn Tyr Thr Glu Ile Arg Gln Tyr Cys Asn
        210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
        370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
                420                 425

<210> SEQ ID NO 2
<211> LENGTH: 429
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Cys Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly

```
            115                 120                 125
Leu Lys Leu Gly Ile Tyr Ala Asp Val Gly Asn Lys Thr Cys Ala Gly
        130                 135                 140

Phe Pro Gly Ser Phe Gly Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Cys Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425

<210> SEQ ID NO 3
<211> LENGTH: 429
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Gln Leu Arg Asn Pro Glu Leu His Leu Gly Cys Ala Leu Ala Leu
1               5                  10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45
```

Cys Phe Met Cys Asn Leu Asp Cys Gln Glu Pro Asp Ser Cys Ile
          50                  55                  60

Ser Glu Lys Leu Phe Met Glu Met Ala Glu Leu Met Val Ser Glu Gly
 65                  70                  75                  80

Trp Lys Asp Ala Gly Tyr Glu Tyr Leu Cys Ile Asp Asp Cys Trp Met
                 85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Cys Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425

<210> SEQ ID NO 4
<211> LENGTH: 429
<212> TYPE: PRT
<213> ORGANISM: Artificial Sequence
<220> FEATURE:

<220> NAME/KEY: source
<223> OTHER INFORMATION: /note="Description of Artificial Sequence: Synthetic polypeptide"

<400> SEQUENCE: 4

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Cys Cys Asn Leu Asp Cys Gln Glu Glu Pro Asp Ser Cys Ile
50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Cys Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
```

```
                385                 390                 395                 400
Ser Arg Leu Arg Ser His Ile Asn Pro Thr Gly Thr Val Leu Leu Gln
                        405                 410                 415

Leu Glu Asn Thr Met Gln Met Ser Leu Lys Asp Leu Leu
                420                 425
```

<210> SEQ ID NO 5
<211> LENGTH: 429
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
                20                  25                  30

Asp Asn Gly Leu Ala Arg Thr Pro Thr Met Gly Trp Leu His Trp Glu
            35                  40                  45

Arg Phe Met Cys Asn Leu Asp Cys Gln Glu Glu Pro Asp Ser Cys Ile
        50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Cys Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320
```

```
Gln Asp Pro Leu Gly Lys Gln Gly Tyr Gln Leu Arg Gln Gly Asp Asn
            325                 330                 335

Phe Glu Val Trp Glu Arg Pro Leu Ser Gly Leu Ala Trp Ala Val Ala
        340                 345                 350

Met Ile Asn Arg Gln Glu Cys Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
            405                 410                 415

Leu Glu Asn Thr Met Gln Met Ser Leu Lys Asp Leu Leu
            420                 425

<210> SEQ ID NO 6
<211> LENGTH: 429
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240
```

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Cys Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425

<210> SEQ ID NO 7
<211> LENGTH: 1290
<212> TYPE: DNA
<213> ORGANISM: Homo sapiens

<400> SEQUENCE: 7

```
atgcagctga ggaacccaga actacatctg ggctgcgcgc ttgcgcttcg cttcctggcc    60
ctcgtttcct gggacatccc tggggctaga gcactggaca tggattggc aaggacgcct    120 accatgggct ggctgcactg ggagcgcttc atgtgcaacc ttgactgcca ggaagagcca    180
gattcctgca tcagtgagaa gctcttcatg agatggcag agctcatggt ctcagaaggc    240
tggaaggatg caggttatga gtacctctgc attgatgact gttggatggc ccccaaaga    300 gattcagaag gcagacttca ggcagaccct cagcgctttc ctcatgggat cgccagcta    360 gctaattatt tcacagcaa aggactgaag ctagggattt atgcagatgt ggaaataaa    420 acctgcgcag gcttccctgg agttttgga tactacgaca ttgatgccca gacctttgct    480
gactggggag tagatctgct aaaatttgat ggttgttact gtgacagttt ggaaaatttg    540
gcagatggtt ataagcacat gtccttggcc ctgaatagga ctggcagaag cattgtgtac    600
tcctgtgagt ggcctcttta tatgtggccc tttcaaaagc ccaattatac agaaatccga    660
cagtactgca atcactggcg aaattttgct gacattgatg attcctggaa agtataaag    720 agtatcttgg actggacatc ttttaaccag agagaattg ttgatgttgc tggaccaggg    780
ggttggaatg acccagatat gttagtgatt ggcaactttg gcctcagctg gaatcagcaa    840
gtaactcaga tggccctctg gctatcatg gctgctcctt attcatgtc taatgacctc    900 cgacacatca gccctcaagc caaagctctc cttcaggata aggacgtaat tgccatcaat    960
caggacccct gggcaagca agggtaccag cttagacagg gagacaactt tgaagtgtgg    1020
gaacgacctc tctcaggctt agcctgggct gtagctatga taaccggca ggagattggt    1080
```

```
ggacctcgct cttataccat cgcagttgct tccctgggta aaggagtggc ctgtaatcct    1140
gcctgcttca tcacacagct cctccctgtg aaaaggaagc tagggttcta tgaatggact    1200
tcaaggttaa gaagtcacat aaatcccaca ggcactgttt tgcttcagct agaaaataca    1260
atgcagatgt cattaaaaga cttactttaa                                    1290

<210> SEQ ID NO 8
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
atgcagctga ggaacccaga actacatctg gctgcgcgc ttgcgcttcg cttcctggcc      60
ctcgtttcct gggacatccc tggggctaga gcactggaca atggattggc aaggacgcct    120
accatgggct ggctgcactg ggagtgcttc atgtgcaacc ttgactgcca ggaagagcca    180
gattcctgca tcagtgagaa gctcttcatg gagatggcag agctcatggt ctcagaaggc    240
tggaaggatg caggttatga gtacctctgc attgatgact gttggatggc tccccaaaga    300
gattcagaag gcagacttca ggcagaccct cagcgctttc ctcatgggat cgccagcta    360 gctaattatg ttcacagcaa aggactgaag ctagggattt atgcagatgt tggaaataaa    420
acctgcgcag gcttccctgg gagttttgga tactacgaca ttgatgccca gacctttgct    480 gactgggggag tagatctgct aaaatttgat ggttgttact gtgacagttt ggaaaatttg    540
gcagatggtt ataagcacat gtccttggcc ctgaataggga ctggcagaag cattgtgtac    600
tcctgtgagt ggcctcttta tgtggccc tttcaaaagc ccaattatac agaaatccga    660
cagtactgca atcactggcg aaattttgct gacattgatg attcctggaa agtataaag    720 agtatcttgg actggacatc ttttaaccag gagagaattg ttgatgttgc tggaccaggg    780
ggttggaatg acccagatat gttagtgatt ggcaactttg gcctcagctg gaatcagcaa    840
gtaactcaga tggccctctg gctatcatg gctgctcctt tattcatgtc taatgaccct    900
cgacacatca gccctcaagc caaagctctc cttcaggata aggacgtaat tgccatcaat    960 caggaccct tgggcaagca agggtaccag cttagacagg gagacaactt tgaagtgtgg   1020
gaacgacctc tctcaggctt agcctgggct gtagctatga taaaccggca ggagattggt   1080
tgccctcgct cttataccat cgcagttgct tccctgggta aaggagtggc ctgtaatcct   1140
gcctgcttca tcacacagct cctccctgtg aaaaggaagc tagggttcta tgaatggact   1200
tcaaggttaa gaagtcacat aaatcccaca ggcactgttt tgcttcagct agaaaataca   1260
atgcagatgt cattaaaaga cttactttaa                                   1290

<210> SEQ ID NO 9
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
atgcagctga ggaacccaga actacatctg gctgcgcgc ttgcgcttcg cttcctggcc      60
```

```
ctcgtttcct gggacatccc tggggctaga gcactggaca atggattggc aaggacgcct    120
accatgggct ggctgcactg ggagtgcttc atgtgcaacc ttgactgcca ggaagagcca    180
gattcctgca tcagtgagaa gctcttcatg gagatggcag agctcatggt ctcagaaggc    240
tggaaggatg caggttatga gtacctctgc attgatgact gttggatggc tccccaaaga    300
gattcagaag gcagacttca ggcagaccct cagcgctttc ctcatgggat cgccagcta    360 gctaattatg ttcacagcaa aggactgaag ctagggattt atgcagatgt tggaaataaa    420
acctgcgcag gcttccctgg gagttttgga tactacgaca ttgatgccca gacctttgct    480
gactggggag tagatctgct aaaatttgat ggttgttact gtgacagttt ggaaaatttg    540
gcagatggtt ataagcacat gtccttggcc ctgaatagga ctggcagaag cattgtgtac    600
tcctgtgagt ggcctctttta tatgtggccc tttcaaaagc ccaattatac agaaatccga    660
cagtactgca atcactggcg aaattttgct gacattgatg attcctggaa agtataaag    720 agtatcttgg actggacatc ttttaaccag gagagaattg ttgatgttgc tggaccaggg    780
ggttggaatg acccagatat gttagtgatt ggcaactttg gcctcagctg aatcagcaa    840 gtaactcaga tggccctctg ggctatcatg gctgctcctt tattcatgtc taatgacctc    900
cgacacatca gccctcaagc caaagctctc cttcaggata aggacgtaat tgccatcaat    960
caggacccct tgggcaagca agggtaccag cttagacagg gagacaactt gaagtgtgg    1020 gaacgacctc tctcaggctt agcctgggct gtagctatga taaaccggca ggagatttgt    1080
ggacctcgct cttataccat cgcagttgct tccctgggta aaggagtggc ctgtaatcct    1140
gcctgcttca tcacacagct cctccctgtg aaaaggaagc tagggttcta tgaatggact    1200
tcaaggttaa gaagtcacat aaatcccaca ggcactgttt tgcttcagct agaaaataca    1260
atgcagatgt cattaaaaga cttactttaa                                     1290

<210> SEQ ID NO 10
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
atgcagctga ggaacccaga actacatctg ggctgcgcgc ttgcgcttcg cttcctggcc     60
ctcgtttcct gggacatccc tggggctaga gcactggaca atggattggc aaggacgcct    120
accatgggct ggctgcactg ggagcgcttc tgctgcaacc ttgactgcca ggaagagcca    180
gattcctgca tcagtgagaa gctcttcatg gagatggcag agctcatggt ctcagaaggc    240
tggaaggatg caggttatga gtacctctgc attgatgact gttggatggc tccccaaaga    300
gattcagaag gcagacttca ggcagaccct cagcgctttc ctcatgggat cgccagcta    360 gctaattatg ttcacagcaa aggactgaag ctagggattt atgcagatgt tggaaataaa    420
acctgcgcag gcttccctgg gagttttgga tactacgaca ttgatgccca gacctttgct    480
gactggggag tagatctgct aaaatttgat ggttgttact gtgacagttt ggaaaatttg    540
gcagatggtt ataagcacat gtccttggcc ctgaatagga ctggcagaag cattgtgtac    600
tcctgtgagt ggcctctttta tatgtggccc tttcaaaagc ccaattatac agaaatccga    660
cagtactgca atcactggcg aaattttgct gacattgatg attcctggaa agtataaag    720 agtatcttgg actggacatc ttttaaccag gagagaattg ttgatgttgc tggaccaggg    780
```

| | |
|---|---|
| ggttggaatg acccagatat gttagtgatt ggcaactttg gcctcagctg aatcagcaa | 840 |
| gtaactcaga tggccctctg ggctatcatg gctgctcctt tattcatgtc taatgacctc | 900 |
| cgacacatca gccctcaagc caaagctctc cttcaggata aggacgtaat tgccatcaat | 960 |
| caggacccct tgggcaagca agggtaccag cttagacagg gagacaactt tgaagtgtgg | 1020 |
| gaacgacctc tctcaggctt agcctgggct gtagctatga taaaccggca ggagatttgt | 1080 |
| ggacctcgct cttataccat cgcagttgct tccctgggta aaggagtggc ctgtaatcct | 1140 |
| gcctgcttca tcacacagct cctccctgtg aaaaggaagc tagggttcta tgaatggact | 1200 |
| tcaaggttaa gaagtcacat aaatcccaca ggcactgttt tgcttcagct agaaaataca | 1260 |
| atgcagatgt cattaaaaga cttactttaa | 1290 |

```
<210> SEQ ID NO 11
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11
```

| | |
|---|---|
| atgcagctga ggaacccaga actacatctg ggctgcgcgc ttgcgcttcg cttcctggcc | 60 |
| ctcgtttcct gggacatccc tggggctaga gcactggaca atggattggc aaggacgcct | 120 |
| accatgggct ggctgcactg ggagcgcttc atgtgcaacc ttgactgcca ggaagagcca | 180 |
| gattcctgca tcagtgagaa gctcttcatg gagatggcag agctcatggt ctcagaaggc | 240 |
| tggaaggatg caggttatga gtacctctgc attgatgact gttggatggc tccccaaaga | 300 |
| gattcagaag gcagacttca ggcagaccct cagcgctttc ctcatgggat cgccagcta | 360 |
| gctaattatg ttcacagcaa aggactgaag ctagggattt atgcagatgt tggaaataaa | 420 |
| acctgcgcag gcttccctgg gagttttgga tactacgaca ttgatgccca gacctttgct | 480 |
| gactggggag tagatctgct aaaatttgat ggttgttact gtgacagttt ggaaaatttg | 540 |
| gcagatggtt ataagcacat gtccttggcc ctgaatagga ctggcagaag cattgtgtac | 600 |
| tcctgtgagt ggcctcttta tatgtggccc tttcaaaagc ccaattatac agaaatccga | 660 |
| cagtactgca atcactggcg aaattttgct gacatttgcg attcctggaa agtataaag | 720 |
| agtatcttgg actggacatc ttttaaccag gagagaattg ttgatgttgc tggaccaggg | 780 |
| ggttggaatg acccagatat gttagtgatt ggcaactttg gcctcagctg aatcagcaa | 840 |
| gtaactcaga tggccctctg ggctatcatg gctgctcctt tattcatgtc taatgacctc | 900 |
| cgacacatca gccctcaagc caaagctctc cttcaggata aggacgtaat tgccatcaat | 960 |
| caggacccct tgggcaagca agggtaccag cttagacagg gagacaactt tgaagtgtgg | 1020 |
| gaacgacctc tctcaggctt agcctgggct gtagctatga taaaccggca ggagtgcggt | 1080 |
| ggacctcgct cttataccat cgcagttgct tccctgggta aaggagtggc ctgtaatcct | 1140 |
| gcctgcttca tcacacagct cctccctgtg aaaaggaagc tagggttcta tgaatggact | 1200 |
| tcaaggttaa gaagtcacat aaatcccaca ggcactgttt tgcttcagct agaaaataca | 1260 |
| atgcagatgt cattaaaaga cttactttaa | 1290 |

```
<210> SEQ ID NO 12
<211> LENGTH: 1290
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

```
atgcagctga ggaacccaga actacatctg gctgcgcgc ttgcgcttcg cttcctggcc      60
ctcgtttcct gggacatccc tggggctaga gcactggaca atggattggc aaggacgcct    120
accatgggct ggctgcactg ggagcgcttc atgtgcaacc ttgactgcca ggaagagcca    180
gattcctgca tcagtgagaa gctcttcatg gagatggcag agctcatggt ctcagaaggc    240
tggaaggatg caggttatga gtacctctgc attgatgact gttggatggc tccccaaaga    300
gattcagaag gcagacttca ggcagaccct cagcgctttc ctcatgggat cgccagcta    360
gctaattatg ttcacagcaa aggactgaag ctagggattt atgcagatgt tggaaataaa    420
acctgcgcag gcttcctgg gagtttgga tactacgaca ttgatgccca gacctttgct    480
gactggggag tagatctgct aaaatttgat ggttgttact gtgacagttt ggaaaatttg    540
gcagatggtt ataagcacat gtccttggcc ctgaatagga ctggcagaag cattgtgtac    600
tcctgtgagt ggcctcttta tatgtggccc tttcaaaagc ccaattatac agaaatccga    660
cagtactgca atcactggcg aaattttgct gacattgatg attcctggaa agtataaag    720
agtatcttgg actggacatc tttttaaccag gagagaattt tgatgttgc tggaccaggg    780
ggttggaatg acccagatat gttagtgatt ggcaactttg gcctctgctg gaatcagcaa    840
gtaactcaga tggccctctg gctatcatg gctgctcctt tattcatgtc taatgacctc    900
cgacacatca gccctcaagc caaagctctc cttcaggata aggacgtaat tgccatcaat    960
caggaccct tgggcaagca agggtaccag cttagacagg gagacaactt tgaagtgtgg   1020
gaacgacctc tctcaggctt agcctgggct gtagctatga taaaccggca ggagattggt   1080
ggacctcgct cttataccat cgcagttgct tccctgggta aaggagtggc ctgtaatcct   1140
gcctgcttca tcacacagct cctccctgtg aaaaggaagc tagggttcta tgaatggact   1200
tcaaggttaa gaagtcacat aaatcccaca ggcactgttt tgcttcagct agaaaataca   1260
atgcagatgt cattaaaaga cttactttaa                                    1290
```

<210> SEQ ID NO 13
<211> LENGTH: 306
<212> TYPE: PRT
<213> ORGANISM: Homo sapiens

<400> SEQUENCE: 13

```
Met Ala Ser Pro Gly Cys Leu Trp Leu Leu Ala Val Ala Leu Leu Pro
1               5                   10                  15

Trp Thr Cys Ala Ser Arg Ala Leu Gln His Leu Asp Pro Pro Ala Pro
                20                  25                  30

Leu Pro Leu Val Ile Trp His Gly Met Gly Asp Ser Cys Cys Asn Pro
            35                  40                  45

Leu Ser Met Gly Ala Ile Lys Lys Met Val Glu Lys Lys Ile Pro Gly
        50                  55                  60

Ile Tyr Val Leu Ser Leu Glu Ile Gly Lys Thr Leu Met Glu Asp Val
65                  70                  75                  80

Glu Asn Ser Phe Phe Leu Asn Val Asn Ser Gln Val Thr Thr Val Cys
                85                  90                  95

Gln Ala Leu Ala Lys Asp Pro Lys Leu Gln Gln Gly Tyr Asn Ala Met
```

-continued

```
                100                 105                 110
Gly Phe Ser Gln Gly Gly Gln Phe Leu Arg Ala Val Ala Gln Arg Cys
            115                 120                 125

Pro Ser Pro Pro Met Ile Asn Leu Ile Ser Val Gly Gly Gln His Gln
        130                 135                 140

Gly Val Phe Gly Leu Pro Arg Cys Pro Gly Glu Ser Ser His Ile Cys
145                 150                 155                 160

Asp Phe Ile Arg Lys Thr Leu Asn Ala Gly Ala Tyr Ser Lys Val Val
                165                 170                 175

Gln Glu Arg Leu Val Gln Ala Glu Tyr Trp His Asp Pro Ile Lys Glu
            180                 185                 190

Asp Val Tyr Arg Asn His Ser Ile Phe Leu Ala Asp Ile Asn Gln Glu
        195                 200                 205

Arg Gly Ile Asn Glu Ser Tyr Lys Lys Asn Leu Met Ala Leu Lys Lys
210                 215                 220

Phe Val Met Val Lys Phe Leu Asn Asp Ser Ile Val Asp Pro Val Asp
225                 230                 235                 240

Ser Glu Trp Phe Gly Phe Tyr Arg Ser Gly Gln Ala Lys Glu Thr Ile
                245                 250                 255

Pro Leu Gln Glu Thr Ser Leu Tyr Thr Gln Asp Arg Leu Gly Leu Lys
            260                 265                 270

Glu Met Asp Asn Ala Gly Gln Leu Val Phe Leu Ala Thr Glu Gly Asp
        275                 280                 285

His Leu Gln Leu Ser Glu Glu Trp Phe Tyr Ala His Ile Ile Pro Phe
    290                 295                 300

Leu Gly
305

<210> SEQ ID NO 14
<211> LENGTH: 306
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Ala Ser Pro Gly Cys Leu Trp Leu Leu Ala Val Ala Leu Leu Pro
1               5                   10                  15

Trp Thr Cys Ala Ser Arg Ala Leu Gln His Leu Asp Pro Pro Ala Pro
            20                  25                  30

Leu Pro Leu Val Ile Trp His Gly Met Gly Asp Ser Cys Cys Asn Pro
        35                  40                  45

Leu Ser Met Gly Ala Ile Lys Lys Met Val Glu Lys Lys Ile Pro Gly
    50                  55                  60

Ile Tyr Val Leu Ser Leu Glu Ile Gly Lys Thr Leu Met Glu Asp Val
65                  70                  75                  80

Glu Asn Ser Phe Phe Leu Asn Val Asn Ser Gln Val Thr Thr Val Cys
                85                  90                  95

Gln Ala Leu Ala Lys Asp Pro Lys Leu Gln Gln Gly Tyr Asn Ala Met
            100                 105                 110

Gly Phe Ser Gln Gly Gly Gln Phe Leu Arg Ala Val Ala Gln Arg Cys
        115                 120                 125

Pro Ser Pro Pro Met Ile Asn Leu Ile Ser Val Gly Gly Gln His Gln
    130                 135                 140
```

```
Gly Val Phe Gly Leu Pro Arg Cys Pro Gly Glu Ser Ser His Ile Cys
145                 150                 155                 160

Asp Phe Ile Arg Lys Thr Leu Asn Ala Gly Cys Tyr Ser Lys Val Val
            165                 170                 175

Gln Glu Arg Leu Val Gln Cys Glu Tyr Trp His Asp Pro Ile Lys Glu
        180                 185                 190

Asp Val Tyr Arg Asn His Ser Ile Phe Leu Ala Asp Ile Asn Gln Glu
    195                 200                 205

Arg Gly Ile Asn Glu Ser Tyr Lys Lys Asn Leu Met Ala Leu Lys Lys
210                 215                 220

Phe Val Met Val Lys Phe Leu Asn Asp Ser Ile Val Asp Pro Val Asp
225                 230                 235                 240

Ser Glu Trp Phe Gly Phe Tyr Arg Ser Gly Gln Ala Lys Glu Thr Ile
                245                 250                 255

Pro Leu Gln Glu Thr Ser Leu Tyr Thr Gln Asp Arg Leu Gly Leu Lys
            260                 265                 270

Glu Met Asp Asn Ala Gly Gln Leu Val Phe Leu Ala Thr Glu Gly Asp
        275                 280                 285

His Leu Gln Leu Ser Glu Glu Trp Phe Tyr Ala His Ile Ile Pro Phe
    290                 295                 300

Leu Gly
305

<210> SEQ ID NO 15
<211> LENGTH: 2504
<212> TYPE: DNA
<213> ORGANISM: Homo sapiens

<400> SEQUENCE: 15
ttattttgat tcaccgcaga gggcggtcta cgagagcgca gagccccact cggccagcgg      60
ggtctggcgg gggaccctgtc gcgctgaaag ctccagggta gggccgacgc ccatcaggct    120
gggcatccgt tcgggatgcg caggttgcga tctgcaaccg gcggcgccac gcccaggcgg    180
gcggagcgcg gttcccggag tctcgcgccc gcggtcatgt gacacagcga agatggcgtc    240
gcccggctgc ctgtggctct tggctgtggc tctcctgcca tggacctgcg cttctcgggc    300
gctgcagcat ctggacccgc cggcgccgct gccgttggtg atctggcatg ggatgggaga    360
cagctgttgc aatcccttaa gcatgggtgc tattaaaaaa atggtggaga agaaaatacc    420
tggaatttac gtcttatctt tagagattgg gaagaccctg atggaggacg tggagaacag    480
cttcttcttg aatgtcaatt cccaagtaac aacagtgtgt caggcacttg ctaaggatcc    540
taaattgcag caaggctaca atgctatggg attctcccag ggaggccaat ttctgagggc    600
agtggctcag agatgcccct tcacctccat gatcaatctg atctcggttg ggggacaaca    660
tcaaggtgtt tttggactcc ctcgatgccc aggagagagc tctcacatct gtgacttcat    720
ccgaaaaaca ctgaatgctg ggcgtactc caaagttgtt caggaacgcc tcgtgcaagc    780
cgaatactgg catgacccca taaggagga tgtgtatcgc aaccacagca tcttcttggc    840
agatataaat caggagcggg gtatcaatga gtcctacaag aaaaacctga tggccctgaa    900
gaagtttgtg atggtgaaat cctcaatga ttccattgtg accctgtag attcggagtg    960 gtttggattt tacagaagtg gccaagccaa ggaaaccatt cccttacagg agacctccct   1020
gtacacacag gaccgcctgg ggctaaagga atggacaat gcaggacagc tagtgtttct   1080
ggctacagaa ggggaccatc ttcagttgtc tgaagaatgg ttttatgccc acatcatacc   1140
```

```
attccttgga tgaaacccgt atagttcaca atagagctca gggagcccct aactcttcca    1200
aaccacatgg gagacagttt ccttcatgcc caagcctgag ctcagatcca gcttgcaact    1260
aatccttcta tcatctaaca tgccctactt ggaaagatct aagatctgaa tcttatcctt    1320
tgccatcttc tgttaccata tggtgttgaa tgcaagttta attaccatgg agattgtttt    1380
acaaactttt gatgtggtca agttcagttt tagaaagggg agtctgttcc agatcagtgc    1440
cagaactgtg cccaggccca aaggagacaa ctaactaaag tagtgagata gattctaagg    1500
gcaaacattt ttccaagtct tgccatattt caagcaaaga ggtgcccagg cctgaggtac    1560
tcacataaat gctttgtttt gctggtgatt taaccagtgc ttggaaaaat cttgcttggc    1620
tatttctgca tcatttctta aggctgcctt cctctctcag tacgttgccc tctgtgctat    1680
catcttatca tcaattatta gacaaatccc actggcctac agtcttgctt ctgcagcacc    1740
cactttgtct cctcaggtag tgatgaatta gttgctgtca caaaggagg gaagtagcac    1800 ccaaattaag ttgcttaaga gaggaaatgt acatcttgta taacttaggg agcgaagaaa    1860
atgtaggcgc gaaagtgaaa agtgaggcag ctagttcttc ctattccatt ctcgaccaac    1920
ctgccctttc ttaatatgac tagtggtctt gatgctagag tcaacttact ctgttgctgg    1980
ctttagcaga gaataggagg aaccatatga aaaagatcag gctttctgac ttccatcccc    2040
aaaacacatt taccagcata ctccaaactg tttctgatgt gttccatgag aaaaggattg    2100
tttgctcaaa aagcttggaa aatactacac actccctttc tccttctgga gatcaaccca    2160
cattagagtg tctaaggact cctgagaatt cctgttacag taaacaaaac taacgtaatc    2220
taccatttcc tacactattt gagcatggaa atcatagtcc ccactctgtg aaaacttaac    2280 gcttttttgga agacatttct gtagcatgtc agtttggaga aatgatgagc tacgccttga    2340
tgaaagaacc gtgttggtgc tgctaagttt agccattatg gttttttcctt tctctctctt    2400 aagccttatt cttcaactaa aagatgagga ttaagagcaa gaagttgggg gggatgtgaa    2460
aataatttta tgaggttgtc taaaataaag agtagtttct tatc                    2504
```

<210> SEQ ID NO 16
<211> LENGTH: 921
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

```
atggcatcac cgggttgcct ctggttgttg gccgttgcgt tgcttccgtg gacatgtgca      60
tcaagagctc ttcaacatct ggatccccca gctcccctgc cgctcgtaat ctggcacggg     120
atgggggatt catgttgtaa cccgttgtca atgggcgcga taaaaaagat ggttgaaaag     180
aagattccag gcatctacgt tctgtccctg gaaatcggta agacactgat ggaagacgtg     240
gagaactcct tctttctcaa cgtcaatagt caggtcacta ccgtctgtca agcattggca     300
aaggacccta aacttcagca ggggtacaat gcgatggggt ttagccaggg cggacagttt     360
cttagagccg tcgcacagcg ctgtccatct cccccgatga ttaaccttat atctgtcggg     420
ggacaacacc agggtgtttt tggtcttcct cgctgtcctg gtgaaagctc ccacatctgt     480
gatttcatac gcaaaacgtt gaacgcagga tgctatagta agtcgtccaa gaacggctt      540 gttcaatgcg agtattggca tgaccccaata aaagaagacg tttataggaa tcactctatc     600
```
ttcttggccg atatcaacca agaacgcgga atcaacgaaa gctacaaaaa gaatcttatg    660
gctctcaaga aatttgttat ggtgaaattc cttaatgact ctatagtaga tcctgtcgat    720
tcagaatggt tcgggttcta caggtctggc caggcgaagg agactattcc cctccaagaa    780
acgtctctct atacacaaga cagactcgga ctgaaagaga tggataatgc gggccagttg    840
gtcttcttgg ctacggaagg cgatcatctc caactctccg aagagtggtt ctatgcccat    900
ataatcccgt tcctgggcta a                                              921

<210> SEQ ID NO 17
<211> LENGTH: 67
<212> TYPE: PRT
<213> ORGANISM: Homo sapiens

<400> SEQUENCE: 17

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 18
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Ala Tyr Arg Pro Ser Glu Thr Leu Cys Gly Gly Glu Leu Val Asp Thr
1               5                   10                  15

Leu Gln Phe Val Cys Gly Asp Arg Gly Ser Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 19
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Leu Phe Ser Arg Pro Ala
            20                  25                  30

```
Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 20
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Leu Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 21
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Thr
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 22
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Ala Tyr Arg Pro Ser Glu Thr Leu Cys Gly Gly Glu Leu Val Asp Thr
1               5                   10                  15
```

```
Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Ser Ser Cys Asp Leu Ala Leu Leu Glu Thr Tyr Cys Ala Thr Pro Ala
    50                  55                  60

Lys Ser Glu
65

<210> SEQ ID NO 23
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ile Cys Asp Leu Ala Leu Leu Glu Thr Tyr Cys Ala Thr Pro Ala
    50                  55                  60

Lys Ser Glu
65

<210> SEQ ID NO 24
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Arg Leu Leu Glu Thr Tyr Cys Ala Thr Pro Ala
    50                  55                  60

Lys Ser Glu
65

<210> SEQ ID NO 25
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ala Tyr Arg Pro Ser Glu Thr Leu Cys Gly Gly Glu Leu Val Asp Thr
```

```
                1               5                  10                  15
Leu Gln Phe Val Cys Gly Asp Arg Gly Phe Tyr Phe Ser Arg Pro Ala
                    20                  25                  30

Ser Arg Val Ser Arg Arg Ser Arg Gly Ile Val Glu Glu Cys Cys Phe
            35                  40                  45

Arg Ser Cys Asp Leu Ala Arg Leu Glu Thr Tyr Cys Ala Thr Pro Ala
    50                  55                  60

Lys Ser Glu
65

<210> SEQ ID NO 26
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Ala Tyr Arg Pro Ser Glu Thr Leu Cys Gly Gly Glu Leu Val Asp Thr
1               5                   10                  15

Leu Gln Phe Val Cys Gly Asp Arg Gly Ser Leu Phe Ser Arg Pro Ala
                    20                  25                  30

Ser Arg Val Ser Arg Arg Ser Arg Gly Ile Leu Glu Glu Cys Cys Thr
            35                  40                  45

Ser Ile Cys Asp Leu Arg Arg Leu Glu Thr Tyr Cys Ala Thr Pro Ala
    50                  55                  60

Lys Ser Glu
65

<210> SEQ ID NO 27
<211> LENGTH: 61
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Thr Leu Cys Gly Gly Glu Leu Val Asp Thr Leu Gln Phe Val Cys Gly
1               5                   10                  15

Asp Arg Gly Phe Leu Phe Ser Arg Pro Ala Ser Arg Val Ser Arg Arg
                    20                  25                  30

Ser Arg Gly Ile Val Glu Glu Cys Cys Phe Arg Ser Cys Asp Leu Ala
            35                  40                  45

Leu Leu Glu Thr Tyr Cys Ala Thr Pro Ala Arg Ser Glu
    50                  55                  60

<210> SEQ ID NO 28
<211> LENGTH: 274
<212> TYPE: RNA
<213> ORGANISM: Cricket paralysis virus

<400> SEQUENCE: 28
cggugucgaa guagaauuuc uaucucgaca cgcggccuuc caagcaguua gggaaaccga    60
cuucuuugaa gaagaaagcu gacuauguga ucuuauuaaa auuagguuaa auuucgaggu   120
uaaaaauagu uuuaauauug cuauagucuu agaggucuug uauauuuaua cuuaccacac   180
```
aagauggacc ggagcagccc uccaauaucu aguguacccu cgugcucgcu caaacauuaa    240
gugguguugu gcgaaaagaa ucucacuuca agaa    274

<210> SEQ ID NO 29
<211> LENGTH: 18
<212> TYPE: PRT
<213> ORGANISM: Homo sapiens

<400> SEQUENCE: 29

Met Lys Leu Ser Leu Val Ala Ala Met Leu Leu Leu Leu Ser Ala Ala
1               5                   10                  15

Arg Ala

<210> SEQ ID NO 30
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Met Lys Leu Ser Leu Val Ala Ala Met Leu Leu Leu Leu Ser Leu Val
1               5                   10                  15

Ala Ala Met Leu Leu Leu Leu Ser Ala Ala Arg Ala
            20                  25

<210> SEQ ID NO 31
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Met Lys Leu Ser Leu Val Ala Ala Met Leu Leu Leu Trp Val Ala
1               5                   10                  15

Leu Leu Leu Leu Ser Ala Ala Arg Ala
            20                  25

<210> SEQ ID NO 32
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Met Lys Leu Ser Leu Val Ala Ala Met Leu Leu Leu Leu Ser Leu Val
1               5                   10                  15

Ala Leu Leu Leu Leu Ser Ala Ala Arg Ala
            20                  25

<210> SEQ ID NO 33
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:

```
            Synthetic peptide"

<400> SEQUENCE: 33

Met Lys Leu Ser Leu Val Ala Ala Met Leu Leu Leu Ala Leu Val
1               5                   10                  15

Ala Leu Leu Leu Leu Ser Ala Ala Arg Ala
            20                  25

<210> SEQ ID NO 34
<211> LENGTH: 10
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34 gccrccaugg                                                              10
```